US011536729B2

(12) United States Patent
Dobson et al.

(10) Patent No.: US 11,536,729 B2
(45) Date of Patent: Dec. 27, 2022

(54) METHOD OF IDENTIFYING NOVEL PROTEIN AGGREGATION INHIBITORS BASED ON CHEMICAL KINETICS

(71) Applicant: Cambridge Enterprise Limited, Cambridge (GB)

(72) Inventors: Christopher Dobson, Cambridge (GB); Tuomas Knowles, Cambridge (GB); Michele Vendruscolo, Cambridge (GB); Johnny Habchi, Cambridge (GB); Sean Chia, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 0 days.

(21) Appl. No.: 16/068,058

(22) PCT Filed: Dec. 28, 2016

(86) PCT No.: PCT/GB2016/054083
§ 371 (c)(1),
(2) Date: Jul. 3, 2018

(87) PCT Pub. No.: WO2017/118841
PCT Pub. Date: Jul. 13, 2017

(65) Prior Publication Data
US 2018/0306813 A1 Oct. 25, 2018

(30) Foreign Application Priority Data

Jan. 6, 2016 (GB) .................................... 1600176

(51) Int. Cl.
*G01N 33/68* (2006.01)
*C07K 14/47* (2006.01)
*G01N 33/50* (2006.01)
*G01N 33/557* (2006.01)
*A61K 38/00* (2006.01)

(52) U.S. Cl.
CPC ...... *G01N 33/6896* (2013.01); *C07K 14/4711* (2013.01); *G01N 33/5058* (2013.01); *G01N 33/557* (2013.01); *A61K 38/00* (2013.01); *G01N 2500/04* (2013.01)

(58) Field of Classification Search
None
See application file for complete search history.

(56) References Cited

U.S. PATENT DOCUMENTS 6,277,826 B1    8/2001   Findeis et al.
2003/0187011 A1 10/2003  Lashuel et al.

FOREIGN PATENT DOCUMENTS

GB     2 455 102 A    6/2009

OTHER PUBLICATIONS

Arosio, P., et al., "Quantification of the Concentration of Aβ42 Propagons during the Lag Phase by an Amyloid Chain Reaction Assay" Journal of the American Chemical Society, 136, (2014), pp. 219-225.
Cohen, S. et al., "From macroscopic measurements to microscopic mechanisms of protein aggregation" Journal of Molecular Biology, 421, (2012), pp. 160-171.
Knowles, T., et al. "An Analytical Solution to the Kinetics of Breakable Filament Assembly" Science, vol. 326, (2009), pp. 1533-1537.
Abelein, A. et al., "Transient small molecule interactions kinetically modulate amyloid β peptide self-assembly", FEBS Letters, 586, (2012), pp. 3991-3995.
Alzheimer's Association, 2012 Alzheimer's disease facts and figures, Alzheimer's & Dementia 8, dated (2012), pp. 131-168.
Appleby, B., et al., "Discovering New Treatments for Alzheimer's Disease by Repurposing Approved Medications" Current Topics in Medical Chemistry, vol. 13, dated (2013), pp. 1-22.
Arosio, P., et al., "Chemical kinetics for drug discovery to combat protein aggregation diseases", Trends in Pharmacological Sciences, 35(3): 127-135 (2014).
Balch, W. et al., "Adapting Proteostasis for Disease Intervention" Science vol. 319, dated Feb. 15, 2008, pp. 916-919.
Bartolini, M., et al., "Insight Into the Kinetic of Amyloid β (1-42) Peptide Self-Aggregation: Elucidation of Inhibitors' Mechanism of Action", Chembiochem—A European Journal of Chemical Biology, 8(17): 2152-2161 (2007).
Bieschke, J. "Natural compounds may open new routes to treatment of amyloid disease" The American Society for Experimental NeuroTherapeutics Inc,. Neurotherapeutics, vol. 10, dated (2013), pp. 429-439.
Bomben, V. et al., "Bexarotene reduces network excitability in models of Alzheimer's disease and epilepsy" Neurobiology Aging, 35, (Sep. 2014), pp. 2091-2095.
Brenner, S. "The Genetics of Caenorhabditis Elegans", Medical Research Council Laboratory of Molecular Biology, (Dec. 10, 1973), pp. 71-94.
Butterfield, S. et al., "Amyloidogenic Protein-Membrane Interactions: Mechanistic Insight from Model Systems" Angew Chem. Int Edition, 49, (2010), 5628-5654.
Caltagirone, C. et al., "The potential protective effect of tramiprostate (homotaurine) against Alzheimer's disease: a review", Aging Clinical and Experimental Research, 24, (2012), pp. 580-587.
Campioni, S. et al., "A causative link between the structure of aberrant protein oligomers and their toxicity", Nature Chemical Biology, vol. 6, (2010), pp. 140-147.
Chen, J. et al., "Small molecular microarrays enable the discovery of compounds that blind the Alzheimer's Aβ peptide" J Am Chem Soc., (2010), pp. 17015-17022.
Chiti, F. et al., "Protein Misfolding, Functional Amyloid, and Human Disease", The Annual Review of Biochemistry, 75, (2006), pp. 333-366.
Cohen, S. et al., "A molecular chaperone breaks the catalytic cycle that generates toxic Aβ oligomer's", Nature Structural & Molecular Biology, (2015), pp. 207-213.

(Continued)

Primary Examiner — Michael L Borin
(74) Attorney, Agent, or Firm — Alston & Bird LLP

(57) ABSTRACT

The subject matter disclosed herein relates to methods of identifying pharmacophores and inhibitors against protein aggregation. The present disclosure also provides pharmacophores themselves and medical uses of agents in the treatment of diseases associated with protein aggregation.

11 Claims, 20 Drawing Sheets

(56) References Cited

OTHER PUBLICATIONS

Figure 1:
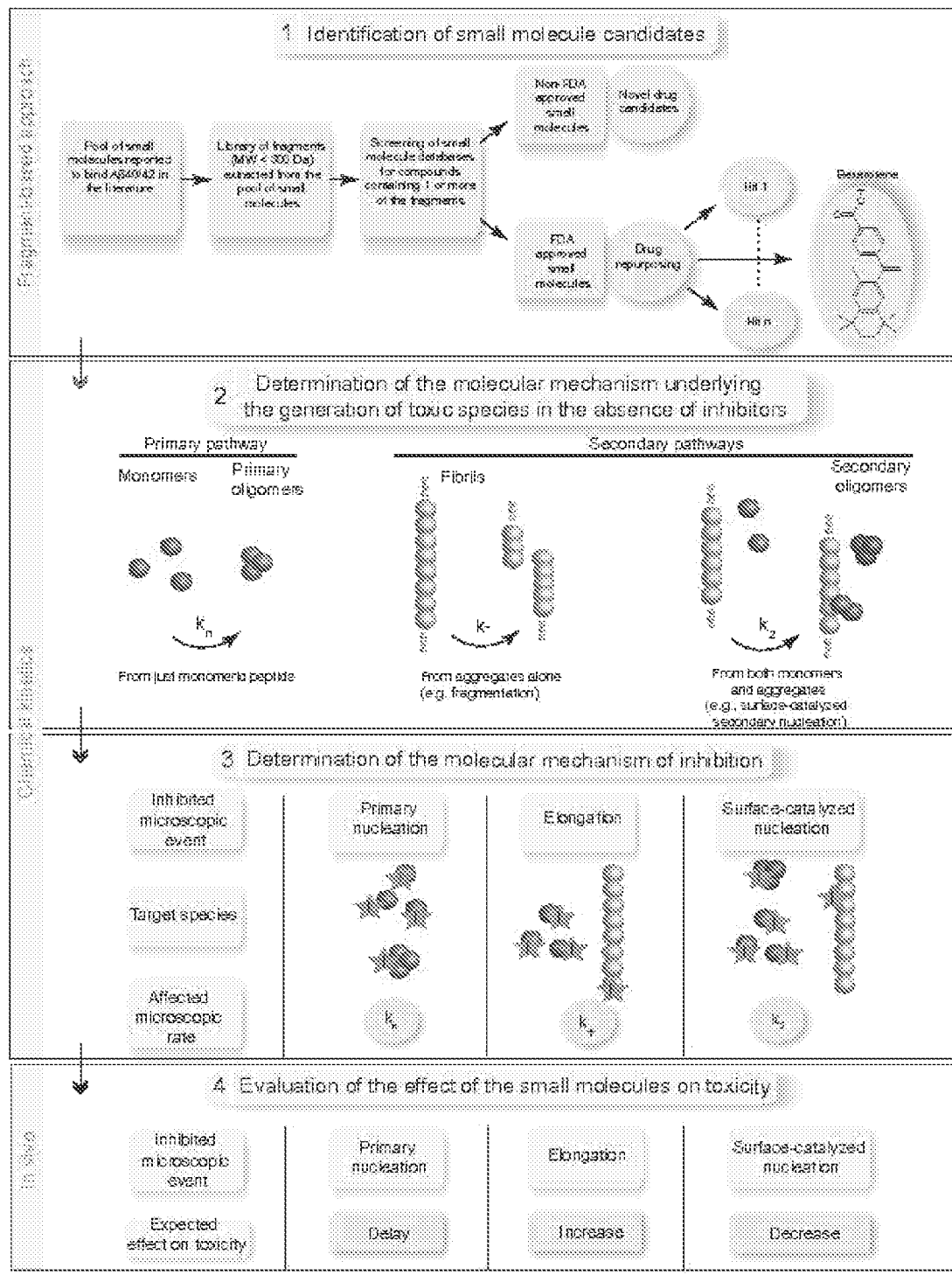

Cohen, S. et al., "Proliferation of amyloid-β42 aggregates occurs through a secondary nucleation mechanism" Proc National Academic Science, 110, (2013), pp. 9758-9763.
Corbett, A. et al., "Drug repositioning: An opportunity to develop novel treatments for Alzheimer's disease" Pharmaceuticals, 6, (2013), pp. 1304-1321.
Cramer, P. et al., "ApoE-Directed Therapeutics Rapidly Clear β-Amyloid and Reverse Deficits in AD Mouse Models" Science, (Mar. 23, 2012), 1503-1506.
Cummings, J. et al., "Alzheimer's disease drug-development pipeline: few candidates, frequent failures" Alzheimer's Research & Therapy, 6:37, (2014), pp. 1-7.
Dobson, C. et al., "Protein folding and misfolding", Nature, vol. 426, (2003), pp. 884-890.
Eisenberg, D. et al., "The amyloid state of proteins in human disease", Cell, dated Mar. 16, 2012, p. 1188-1203.
Fantini, J. et al., "Beaxtone blocks calcium-permeable Ion channels formed by neurotoxic Alzheimer's β-Amyloid peptides" ACS Chemical Neuroscience, (2014), pp. 216-224.
Fitz, N. et al., "Comment on ApoE-Directed Therapeutics Rapidly Clear β-Amyloid and Reverse Deficits in AD Mouse Models", Science, 340, (May 24, 2013), pp. 924-c.
Haass, C. et al., "Soluable protein oligomers in neurodegeneration: lessons from The Alzheimer's amyloid (β-peptide", Nature Reviews Molecular Cell Biology, vol. 8, (2008), pp. 101-112.
Habchi, J. et al., "An anticancer drug suppresses the primary nucleation reaction that initiates the production of the toxic Aβ42 aggregates linked with Alzheimer's. disease" Science Mag, (Feb. 12, 2016), pp. 1-13.
Habchi, J. et al., "Introducing Protein Intrinsic Disorder", Chemical Reviews, 114, (2014), pp. 6561-6588.
Habchi, J. et al., "Systematic development of small molecules to inhibit specific microscopic steps of Aβ42 aggregation in Alzheimer's disease", PNAS, 114, E200-E208.
Hajduk, P. et al., "Small molecules, great potential", Nature, vol. 470, (2011), pp. 42-43.
Hartl, U. et al., "Molecular chaperones in protein folding and proteostasis", Nature, vol. 475, (2011), pp. 324-332.
Hellstrand, E. et al., "Amyloid β-Protein Aggregation Produces Highly Reproducible Kinectic Data and Occurs by a Two-phase Process" ACS Chemical Neuroscience, 1, (2010), pp. 13-18.
Ito, M. et al., "Effects of Ligands on Unfolding of the Amyloid β-Peptide Central Helix; Mechanistic Insights from Molecular Dynamics Simulations" Plos One, e30510, (2012), pp. 1-13.
Knowles, T. et al., "The amyloid state and its association with protein misfolding diseases", Nature Reviews, Molecular Cell Biology, vol. 15, dated Jun. 2014, pp. 384-396.
Kroth, H. et al., "Discovery and Structure Activity Relationship of Small Molecule Inhibitors of Toxic β-Amyloid-42 Formation" Journal of Biological Chemistry, vol. 287, No. 41, (Oct. 05, 2012), pp. 34786-34800.
LaClair, K. et al., "Treatment with bexarotene, a compound that increases apolipoprotein-E, provides no cognitive benefit in mutant APP/PS1 mice" Molecular Neurodegeneration, 8, (2013), pp. 1-13.
Lansbury, P. et al., "A century-old debate on protein aggregation and neurodegeneration enters the clinic" Nature, vol. 443, (2006), pp. 774-779.
Mannini, B. et al., "Toxicity of Protein Oligomers is Rationalized by a function combining size and surface Hydrophobicity", ACS Chemical Biology, 9, (2014), pp. 2309-2317.
Martins, P. et al., "True and Apparent Inhibition of Amyloid Fibril Formation", Prion 7:2, dated Mar.-Apr. 2013, pp. 136-139.
McColl, G. et al., "Utility of an improved model of amyloid-beta (Aβ1-42) toxicity in Caenorhabditis elegans for drug screening for Alzheimer's disease" Molecular Neurodegeneration, (2012), pp. 1-9.
Meisl, G., et al., "Differences in nucleation behavior underlie the contrasting aggregation kinetics of the Aβ40 and Aβ42 peptides", Proceedings of the National Academy of Sciences, 111(26): 9384-9389 (2014).
Necula, M et al., "Small Molecule Inhibitors of Aggregation Indicate that Amyloid β Oligomerization and Fibrillization Pathways Are Independent and Distinct" The Journal of Biological Chemistry, vol. 282, No. 14, (Apr. 06, 2007), pp. 10311-10324.
Nie, Q. et al., "Small molecule inhibitors of amyloid β peptide aggregation as a potential therapeutic strategy for Alzheimer's disease" Acta Pharmacologica Sinica, 32, (2011), pp. 545-551.
Olzscha, H. et al., "Amyloid-like Aggregates Sequester Numerous Metastable Proteins with Essential Cellular Functions", Cell, (2011), pp. 67-78.
International Search Report and Written Opinion for International Application No. PCT/GB2016/054083 dated Apr. 24, 2017.
Porat, Y. et al., "Inhibition of Amyloid Fibril Formation by Polyphenols: Structural Similarity and Aromatic Interactions as a Common Inhibition Mechanism" Chem Biol Drug Des, 67, (2006), pp. 27-37.
Price, A. et al., Comment on "ApoE-Directed Therapeutics Rapidly Clear βAmyloid and Reverse Deficits in AD Mouse Models", Science, (2013), pp. 924-d.
Rees, D. et al., "Fragment-Based Lead Discovery", Nature Reviews, vol. 3, (2004), pp. 660-672.
Roychaudhuri, R. et al., "Amyloid β-Protein Assembly and Alzheimer Disease" The Journal of Biological Chemistry, vol. 284, No. 8, (Feb. 20, 2009), pp. 4749-4753.
Selkoe, D. "Folding proteins in fatal ways", Nature, vol. 426, (2003), pp. 900-904.
Selkoe, D. "Resolving controversies on the path to Alzheimer's therapeutics", Nature Medicine, (2011), pp. 1060-1065.
Shankar, G. et al., "Amyloid β-Protein dimers isolated directly from Alzheimer brains impair synaptic plasticity and memory" Nat Med, 14, (2008), pp. 837-842.
Sinha, A. et al., "Lysine-specific molecular tweezers are broad-spectrum inhibitors of assembly and toxicity of amyloid proteins" J Am Chem Soc., 133, (Oct. 26, 2011), pp. 16958-16969.
Sipe, J. et al., "Nomenclature 2014: Amyloid fibril proteins and clinical classification of the amyloidosis" The Journal of Protein Folding Disorders, (2014), pp. 1-5.
Sperling, R. et al., "Toward defining the preclinical stages of Alzheimer's disease: Recommendations from the National Institute on Aging-Alzheimer's Association workgroups on diagnostic guidelines for Alzheimer's disease" Alzheimer's Dementia, (May 2011), pp. 280-292.
Tesseur, I. et al., "Comment on ApoE-Directed Therapeutics Rapidly Clear β-Amyloid and Reverse Deficits in AD Mouse Models", Science, 340, (May 24, 2013), pp. 924-e.
Vazquez, J.A., "Modeling of chemical inhibition from amyloid protein aggregation kinetics", BMC Pharmacology and Toxicology, 15(1): 9 (2014).
Veeraraghavalu, K. et al., "Comment on ApoE-Directed Therapeutics Rapidly Clear β-Amyloid and Reverse Deficits in AD Mouse Models", Science, (2013), pp. 924-f.
Walsh, D. et al., "A facile method for expression and purification Alzheimer's disease-associated amyloid β-peptide" The FEBS Journal, (2009), pp. 1266-1281.
Walsh, D. et al., "Aβ Oligomers—a decade of discovery" Journal of Neurochemistry, 101, (2007), pp. 1172-1184.
Willander, H., et al., "BRICHOS domains efficiently delay fibrillation of amyloid β-peptide", Journal of Biological Chemistry, 287(37): 31608-31617 (2012).
Andrés, M. et al., "Structure-activity relationships (SAR) and structure-kinetic relationships (SKR) of pyrrolopiperidinone acetic acids as CRTh2 antagonists," Bioorganic & Medicinal Chemistry Letters, 24:5111-5117, (2014).
Chia, S. et al., "SAR by kinetics fordrug discovery in protein misfolding diseases," PNAS, 115(41):10245-10250, (Oct. 9, 2018).
European Application No. 16 822 508.4, EP Communication Pursuant to Article 94(3) EPC dated Apr. 14, 2022, 8 pgs.
Ferreira et al., *Molecular Docking and Structure-Based Drug Design Strategies*, Molecules 2015, vol. 20, pp. 13384-13421, published Jul. 22, 2015.
Office Action for Japanese Application No. 535172/2018, dated Nov. 24, 2020 (4 pages).

(56) References Cited

OTHER PUBLICATIONS

1st Office Action for China Application No. 201680083229.3 dated Feb. 19, 2021 (14 pages).
J. Russo, *Molecular Basis of Breast Cancer*, Springer, Oct. 2013 (20 pages).

METHOD OF IDENTIFYING NOVEL PROTEIN AGGREGATION INHIBITORS BASED ON CHEMICAL KINETICS

CROSS-REFERENCE TO RELATED APPLICATIONS

This application is a U.S. National Stage entry of International Application No. PCT/GB2016/054083 filed Dec. 28, 2016, which claims the benefit of United Kingdom Patent Application No. 1600176.0, filed Jan. 6, 2016, each of which is herein incorporated by reference in its entirety for all purposes.

FIELD OF THE INVENTION

The present invention relates to methods based on chemical kinetics for identifying novel inhibitors of protein aggregation, particularly inhibitors that inhibit aggregation of amyloid proteins associated with human misfolding diseases. The invention also relates to a method of designing and generating a pharmacophore against protein aggregation. Also within the scope of the invention are compositions and methods for the treatment of Alzheimer's disease and for the inhibition of protein aggregation in other protein misfolding diseases.

BACKGROUND

Intracellular protein misfolding or aggregation is a feature of many late-onset neurodegenerative diseases, called proteinopathies. These include Alzheimer's disease, Parkinson's disease, tauopathies, and polyglutamine expansion diseases, such as Huntington's disease and various spinocerebellar ataxias (SCAs), like SCA3.

At present there are no effective strategies to slow or prevent the neurodegeneration resulting from these diseases in humans. Indeed, the incidence of Alzheimer's disease (AD) is increasing rapidly as the global population ages. It is estimated that 44 million people currently suffer from AD and that this number will exceed 135 million by 2050 (1).

AD is one of over 40 related disorders (2) characterized by the misfolding of a soluble protein and its subsequent conversion into amyloid fibrils (3-9). A key molecular pathway that underlies AD is the aggregation of Aβ42, the 42-residue form of the Aβ peptide, which is a fragment produced by the proteolytic cleavage of the amyloid precursor protein (APP) (3-5, 8, 9). Aβ42 is an intrinsically disordered peptide (10) that self-assembles into fibrillar aggregates observed in the brains of AD patients (5, 9). Inhibiting the self-assembly of Aβ42 has, therefore, emerged as a major potential therapeutic strategy against AD (11-20), although no small molecule designed to achieve this effect has yet shown clinical efficacy (21).

Such clinical failures are caused at least in part by the incomplete knowledge of the molecular mechanisms underlying the generation of toxic species and of the processes by which small molecules are able to interfere with the aggregation pathway of Aβ42. In addition, it is increasingly evident that prefibrillar oligomeric species, rather than mature amyloid fibrils and plaques, represent the main pathogenic agents in AD and other neurodegenerative conditions (3, 22-27). Accordingly, effective therapeutic strategies are unlikely to consist of a non-specific suppression of Aβ42 fibril formation, but rather to involve the targeting of specific species in a controlled intervention at precise microscopic steps during the complex aggregation process of Aβ42 (28).

A therapeutic strategy of this type can now be proposed by exploiting recent major advances in our understanding of the molecular processes underlying amyloid formation. These advances are the result of the innovative application of chemical kinetics to the study of protein aggregation (29, 30). The availability of highly reproducible data obtained from kinetic measurements based on thioflavin-T (ThT) fluorescence (31) has recently allowed us to define the Aβ42 aggregation mechanism in terms of its underlying molecular events (30). It was thus observed that once a small but critical concentration of Aβ42 aggregates was generated through primary nucleation of monomers, surface-catalyzed secondary nucleation becomes the dominant process, whereby the surfaces of the fibrils once formed serve as catalytic sites for the generation of toxic oligomeric species (30). These oligomers can then grow and convert into additional fibrils, thus promoting further the formation of additional toxic species in a highly effective catalytic cycle (30).

These results can now be taken further as they offer the possibility of investigating the mechanism of inhibition of the Aβ42 aggregation process by therapeutic molecules (28, 29, 32). Approaches using chemical kinetics, which do not require prior knowledge of the elusive structures of the toxic species and are not limited by the need of very tight binding of small molecules to the aggregation-prone proteins, provide highly sensitive methods for the quantitative detection of the effects of potential therapeutic molecules on the aggregation process. By adopting this strategy, it has been possible to show that bexarotene, which is an FDA approved anti-cancer drug, targets selectively the primary nucleation step in the self-assembly of Aβ, delays the formation of toxic species in neuroblastoma cells, and completely suppresses Aβ aggregation and its pathological effects in a *C. elegans* model of Aβ-mediated toxicity.

There is however a need not only to identify the specific microscopic steps (i.e. primary and secondary nucleation, elongation and fragmentation) that give rise to the overall aggregation process at which an already known or predicted inhibitor of protein aggregation acts, but to identify new inhibitors of protein aggregation and moreover, new inhibitors that can be rationally identified or selected to specifically target the key microscopic stages that affect formation of soluble toxic oligomers, namely primary and/or secondary nucleation. The present invention is aimed at providing methods that address this need.

Drug discovery approaches based on kinetics, such as the one described here, are fundamentally different from traditional approaches based on the atomic structure of target proteins, such as enzymes or receptors. For "stable" (e.g. non-transient) states, such structure based drug discovery is appropriate. For example, crystallography may be used to determine structurally how a ligand interacts with a target, and new structures are then derived based on this interaction. However, such structure based drug discovery is not appropriate for targets which only exist transiently, such as those which may exist during protein aggregation. In accordance with the invention, new inhibitors of protein aggregation are therefore determined based on function, i.e. by kinetics.

These kinetic approaches are essential to target kinetic phenomena, such as protein aggregation.

SUMMARY OF THE INVENTION

In a first aspect of the invention there is provided a method of producing a pharmacophore against aggregation of an aggregation prone protein, the method comprising (a) providing at least one inhibitor of the protein aggregation;
(b) generating a inhibitor scaffold from the at least one inhibitor;
(c) introducing at least one chemical substitution into at least one component of the inhibitor scaffold and analysing the effect of the at least one chemical substitution of the aggregation kinetics of said aggregation-prone protein, wherein analysing the effect on aggregation kinetics comprises producing a kinetic profile of said protein in the absence and presence of a compound with at least one chemical substitution, and identifying a substitution as a positive result if said substitution causes a shift in the kinetic profile; and
(d) producing a pharmacophore against aggregation of a aggregation-prone protein by aligning the positive results from the kinetic assay.

The invention also provides a method for identifying an inhibitor of protein aggregation, wherein said protein is an aggregation-prone protein, the method comprising
identifying at least one compound that binds to the same binding partner and/or a highly related binding partner as a known or predicted inhibitor, wherein said at least one compound binds to the same binding site or pocket as the known or predicted inhibitor;
analysing the effect of the at least one compound on the aggregation kinetics of the aggregation-prone protein; and
selecting the at least one compound as an inhibitor if said compound affects the aggregation kinetics of the aggregation-prone protein.

In one embodiment, the method further comprises identifying a known or predicted inhibitor and identifying and characterising a binding partner of said inhibitor.

Preferably, protein aggregation can be divided into multiple, preferably three, microscopic stages that are primary nucleation, secondary nucleation and elongation, and wherein said inhibitor inhibits at least one of these stages. More preferably, said inhibitor inhibits at least primary and/or secondary nucleation.

In one embodiment, analysing the effect of the at least one compound on the aggregation kinetics of said aggregation-prone protein comprises producing a kinetic profile of said protein in the absence and presence of the compound or compounds wherein said compound or compounds is/are identified as an inhibitor(s) if it causes a shift in the kinetic profile. Preferably, the kinetic profile is a sigmoidal curve, wherein said curve comprises at least a lag phase, a growth phase and a plateau originating from primary nucleation, secondary nucleation and elongation processes and wherein the at least one compound alters at least one of these processes. More preferably, rate parameters are obtained from the kinetic profile by fitting the curves using the following equation:

$$\frac{M(t)}{M(\infty)} = 1 - \alpha \left( \frac{B_+ + C_+}{B_+ + C_+ e^{kt}} \frac{B_- + C_+ e^{kt}}{B_- + C_+} \right)^{\frac{k_\infty^2}{kk_\infty}} e^{-k_\infty t}$$

where the kinetic parameters $B_\pm$, $C_\pm$, $\kappa$, $\kappa_\infty$ and $\tilde{\kappa}_\infty$ are functions of the two combinations of the microscopic rate constants $k_+ k_2$ and $k_n k_2$, where $k_n$, $k_+$ and $k_2$ are the primary nucleation, elongation and secondary nucleation rate constants, respectively.

In another embodiment, the known or predicted inhibitor is itself identified by analysing the effect of the inhibitor on the aggregation kinetics of the aggregation-prone protein, wherein said inhibitor is identified as such if it causes a shift in the kinetic profile.

In a further aspect of the present invention, there is provided a protein aggregation inhibitor obtained or obtainable by the above method.

In another aspect of the present invention, there is provided a method of producing a pharmacophore against aggregation of an aggregation-prone protein, the method comprising:
identifying at least one inhibitor of protein aggregation using the method defined above; and
generating a inhibitor scaffold from the at least one inhibitor and producing a pharmacophore using the method defined above.

The inhibitor scaffold may be generated from the at least one inhibitor in addition from the known or predicted inhibitor described in the method above.

In a further aspect of the present invention, there is provided a pharmacophore obtained or obtainable by the methods described herein.

In another aspect of the present invention, there is provided a pharmacophore that inhibits aggregation of Aβ42, the pharmacophore comprising at least nine features, wherein said features are two hydrogen bond acceptors and one negatively charged feature at the terminal end which represents the carboxylic acid group and one aromatic feature attached to five hydrophobic features.

The pharmacophore may have a horizontal distance of 9.22 Å from the terminal hydrophobic group to the other polar terminus.

In a further aspect of the present invention, there is provided a method for treatment of Alzheimer's disease, the method comprising administering to a patient in need thereof a retinoid receptor modulator, wherein the modulator is selected from the group consisting of a retinoid A receptor (RAR) agonist, selected from Adapalene, CD 1530, TTNPB and Ch55, a retinoid A receptor (RAR) antagonist selected from BMS195614, LE135, MM11253 and BMS493, a retinoid X receptor agonist that is SS11237 and a retinoid X receptor antagonist that is UVI3003.

In another aspect of the present invention, there is provided a retinoid receptor modulator for use in the treatment of Alzheimer's disease, wherein the modulator is selected from the group consisting of a retinoid A receptor (RAR) agonist, selected from Adapalene, CD 1530, TTNPB and Ch55, a retinoid A receptor (RAR) antagonist selected from BMS195614, LE135, MM11253 and BMS493, a retinoid X receptor agonist that is SS11237 and a retinoid X receptor antagonist that is UVI3003.

In a further aspect of the present invention, there is provided the use of a retinoid receptor modulator in the manufacture of a medicament for use in the treatment of a Alzheimer's disease, wherein the modulator is selected from the group consisting of a retinoid A receptor (RAR) agonist, selected from Adapalene, CD 1530, TTNPB and Ch55, a retinoid A receptor (RAR) antagonist selected from BMS195614, LE135, MM11253 and BMS493, a retinoid X receptor agonist that is SS11237 and a retinoid X receptor antagonist that is UVI3003.

In a yet further aspect of the present invention, there is provided a method for the inhibition of aggregation of an aggregation-prone protein, wherein the aggregation-prone protein is Aβ42, the method comprising administering, preferably, to a patient in need thereof a protein aggregation inhibiting amount, of a retinoid receptor modulator, wherein the modulator is selected from the group consisting of a retinoid A receptor (RAR) agonist, selected from Tamibarotene, Adapalene, CD 1530, TTNPB and Ch55, a retinoid A receptor (RAR) antagonist selected from BMS195614, LE135, MM11253 and BMS493, a retinoid X receptor agonist selected from SS11237 and Bexarotene and a retinoid X receptor antagonist that is UVI3003.

In a final aspect of the present invention there is provided the use of a retinoid receptor modulator to inhibit the aggregation of an aggregation-prone protein, wherein said aggregation-prone protein is Aβ42, and wherein the modulator is selected from the group consisting of a retinoid A receptor (RAR) agonist, selected from Tamibarotene, Adapalene, CD 1530, TTNPB and Ch55, a retinoid A receptor (RAR) antagonist selected from BMS195614, LE135, MM11253 and BMS493, a retinoid X receptor agonist selected from SS11237 and Bexarotene and a retinoid X receptor antagonist that is UVI3003.

In one embodiment of either the method or use described above, protein aggregation can be divided into multiple microscopic stages, and preferably at least three microscopic stages that are primary nucleation, secondary nucleation and elongation, and wherein said retinoid receptor modulator inhibits at least one of these stages.

Preferably, said retinoid receptor modulator inhibits primary and/or secondary nucleation. More preferably, the modulator inhibits all microscopic stages, and wherein the modulator is selected from MM11253, BMS493, Adapalene, CD 1530 and LE135.

In one embodiment of all above aspects, the aggregation-prone protein is a amyloid protein. Preferably, the amyloid protein is selected from Aβ42, α-synuclein, tau, huntingtin, atrophin-1, ataxin (1, 2, 3, 6, 7, 8 12, 17), amylin, prion protein, (pro)calcitonin, atrial natriuretic factor, apolipoprotein AI, apolipoprotein AII, apolipoprotein AIV, serum amyloid, medin, (apo) serum AA, prolactin, transthyretin, lysozyme, β-2 microglobulin, fibrinogen α chain, gelsolin, keratopthelin, β-amyloid, cystatin, ABriPP immunoglobulin light chain AL, immunoglobulin heavy chain, S-IBM, islet amyloid polypeptide, insulin, lactadherin, kerato-epithelium, lactoferrin, tbn, leukocyte chemotactic factor-2, AbriPP, ADanPP, lung surfactant protein, galectin 7, corneodesmosin, lactadherin, kerato-epitelium, odontogenic ameloblast-associated protein, semenogelin 1 and enfurvitide. Preferably the amyloid protein is selected from Aβ42, α-synuclein, tau and huntingtin. More preferably, the amyloid protein is Aβ42.

The invention is further described in the following non-limiting figures.

FIGURES

FIG. 1: Schematic illustration of the drug discovery strategy described in this work. The strategy consists of 4 steps: (1) A fragment-based approach that allows the identification of small molecules that interact with the aggregation-prone system, here Aβ42, including FDA approved molecules for drug repurposing; (2) An in vitro kinetic analysis that identifies the specific molecular steps in the Aβ42 aggregation mechanism responsible for the generation of toxic species; (3) A further kinetic analysis to determine the mechanism of inhibition associated with the molecules identified in (1); and (4) An evaluation of the effects of these molecules on the formation of toxic species in vivo. In particular, the inhibition of primary nucleation is predicted only to delay the aggregation without affecting the total number of oligomers generated by the aggregation process, while inhibiting elongation or secondary nucleation is predicted either to increase or to decrease the number of toxic oligomers, respectively.

Figure 2:
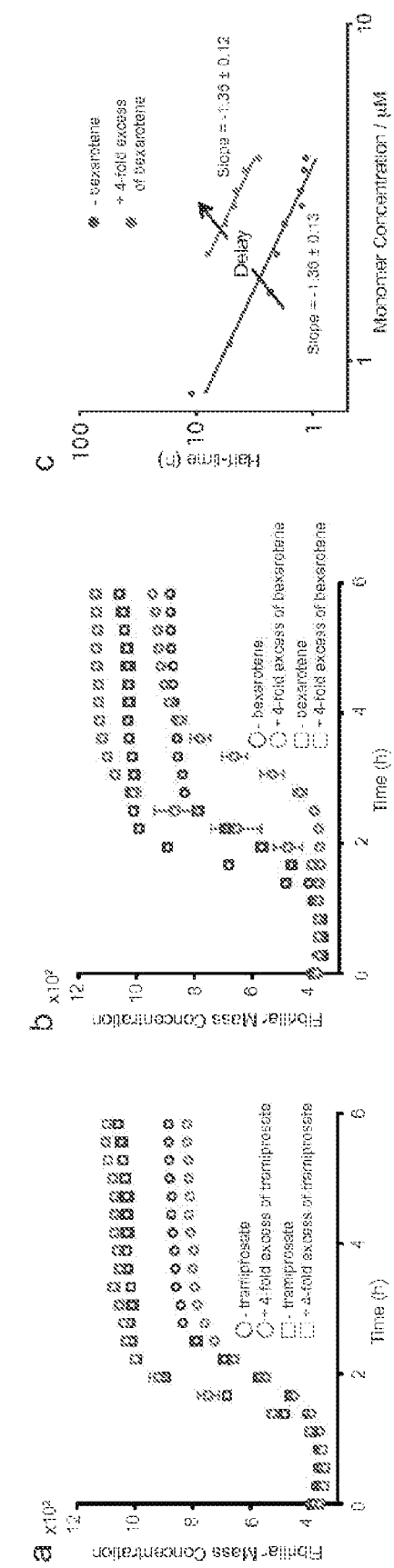

FIG. 2: Bexarotene, but not tramiprosate, delays the formation of Aβ42 fibril formation. (a) Kinetic profiles of Aβ42 aggregation under quiescent conditions at a concentration of 3 μM (open circles) and 4 μM (open squares) in the absence or in the presence of a 4-fold excess of tramiprosate. (b) Kinetic profiles of Aβ42 aggregation under quiescent conditions at a concentration of 3 μM (open circles) and 4 μM (open squares) in the absence or in the presence of a 4-fold excess of bexarotene. (c) Average half-time of the aggregation reaction as a function of the initial monomer concentration in the absence or in the presence of 4-fold excess of bexarotene.

Figure 3:
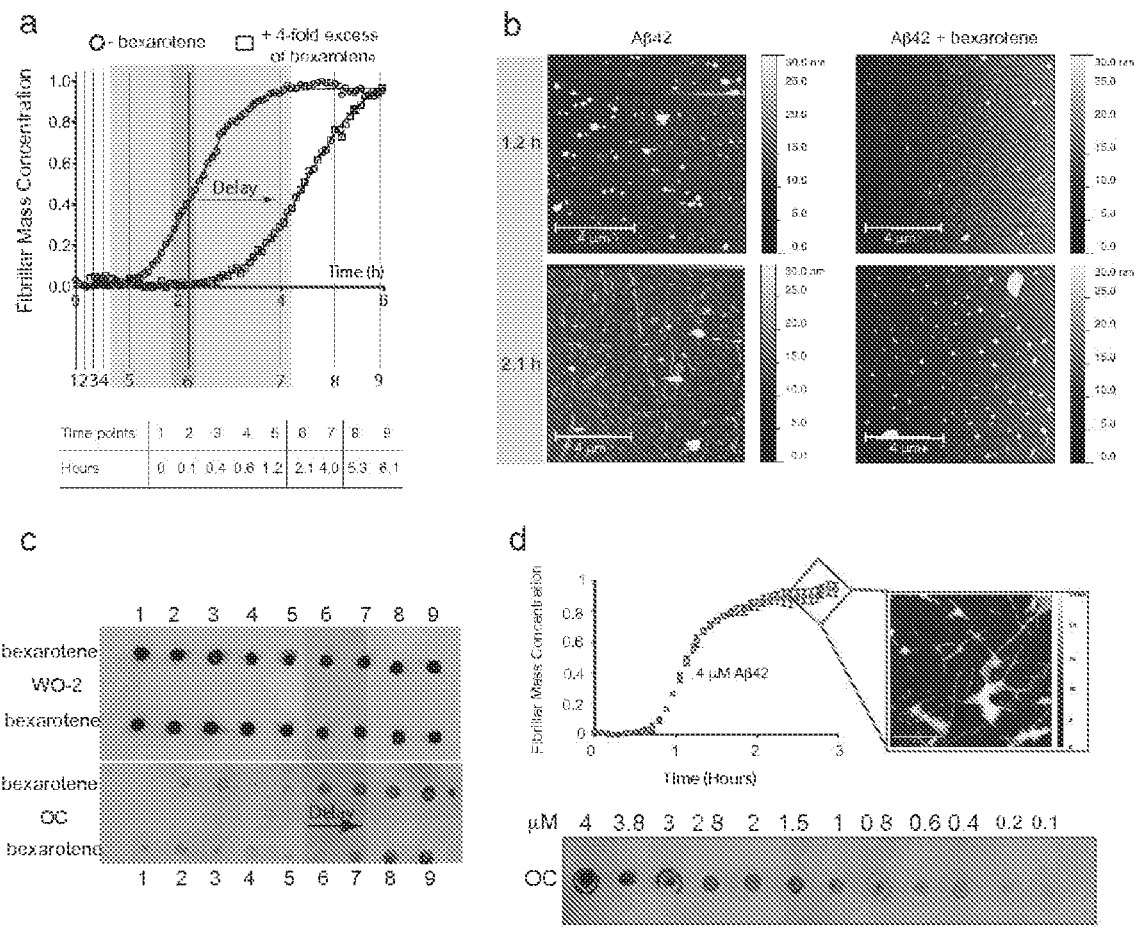

FIG. 3: Bexarotene delays Aβ42 fibril formation in a label-free environment. (a) Kinetic profiles of the aggregation of 2 μM Aβ42 under quiescent conditions in the absence and in the presence of a 4-fold excess of bexarotene; the table below the graph shows the equivalent of the different time points in hours (represented in black solid lines in the graph) at which aliquots of Aβ42 were removed from a solution of 2 μM peptide undergoing aggregation. (b) AFM images of Aβ42 species in the absence and in the presence of a 4-fold excess of bexarotene. Images were acquired with tapping mode in air on aliquots of the Aβ42 solutions that were removed from the aggregation reaction at 1.2 and 2.1 h time points. Note that fibrillar structures can be observed after 2.1 h only in the absence of bexarotene. (c) Time course of the formation of 2 μM Aβ42 fibrils as assessed by antibody binding. The quantity of Aβ42 peptide that was detected by the sequence-specific W0-2 antibody (upper panel) remained unchanged during the complete time course of the reaction on the total quantity of Aβ42 (in solution or as aggregates). The fibril-specific OC antibody (lower panel), however, probes only fibrillar structures that can be seen to have formed earlier in the absence of bexarotene than in its presence. The extent of the observed delay (highlighted in red) is in complete accord with the aggregation profiles shown in (a). (d) Calibration of the dependence of Aβ42 fibril mass concentration to the dot-blot intensity of the fibril-specific OC antibody. (Top) Kinetic profile of 4 μM Aβ42 by means of ThT fluorescence. AFM image of typical mature Aβ42 fibrils acquired with tapping mode in air, formed at pH 8. (Bottom) Dot-blot intensities obtained from binding of fibril-specific OC antibody to a serial dilution of Aβ42 fibrils that were collected after 3 hours incubation of a fresh 4 μM Aβ42 monomer. Fibril concentrations were in the range of 4 μM to 0.1 μM.

Figure 4:
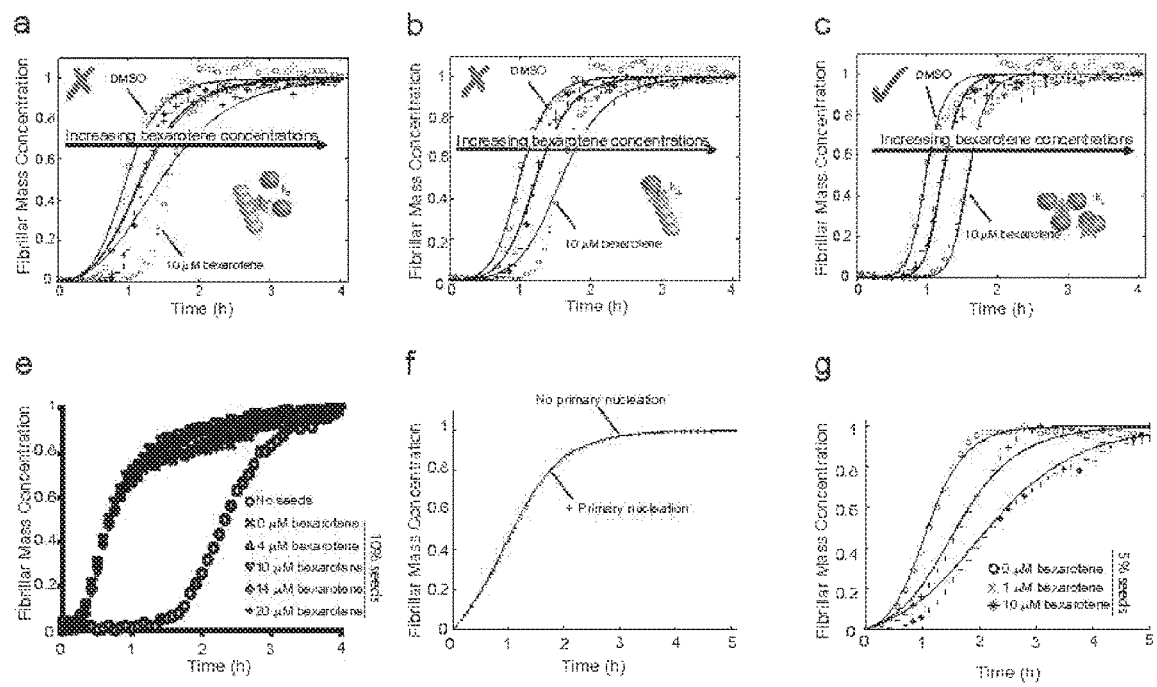

FIG. 4: Bexarotene targets selectively the primary nucleation of Aβ42. (a-c) Kinetic profiles of the aggregation reaction of 5 μM Aβ42 in the absence or in the presence of a 1:1 or 5:1 concentration ratio of bexarotene to Aβ42 (represented by different colors). The solid lines show predictions for the resulting reaction profiles when either secondary nucleation (a), fibril elongation (b), or primary nucleation (c) are inhibited by bexarotene. Only the prediction for the case where primary nucleation alone is inhibited fits closely the experimental data for bexarotene. (d) Evolution of the apparent reaction rate constants with increasing concentration ratios of bexarotene (kn is the rate of primary nucleation, k+ of elongation and k2 of secondary nucleation, K represents in each case either knk+ or k2k+). Note the significant decrease in primary pathways, knk+, when compared to secondary pathways, k2k+, as the concentration of bexarotene is increased. (e) Kinetic profiles of 2 μM Aβ42 without and with the addition of 10% of pre-formed seed fibrils in the absence or in the presence of a 2, 5, 7 and 10-fold excess of bexarotene (represented by different symbols). Note the rapid increase in the slope of the aggregation reaction in the presence of pre-formed seed fibrils compared to that of the reaction without the addition of preformed fibrils. (f) Simulations showing identical curves for the aggregation profile of a 2 µM Aβ42 sample in the presence of 5% of pre-formed fibril seeds where primary nucleation events either contributes or is negligible. (g) Effect of 0.5- and 5-fold excess of bexarotene on the aggregation kinetics of a 2 µM Aβ42 sample in the presence of 5% of pre-formed fibril seeds. (h) Effect of 0.5- and 5-fold excess of bexarotene on the rates of surface-catalyzed secondary nucleation (K2) as obtained from the aggregation kinetics in (g).

Figure 5:
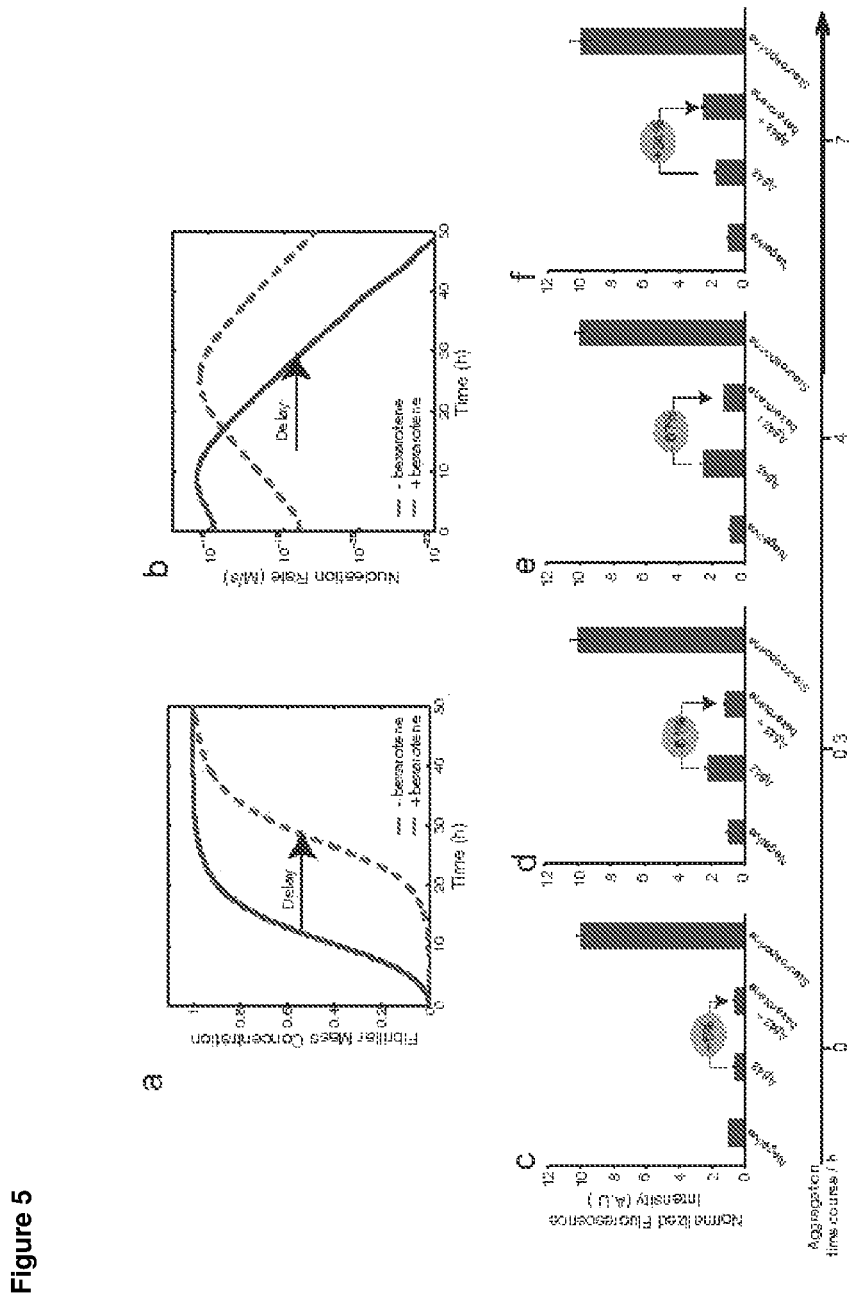

FIG. 5: Bexarotene delays the formation of Aβ42 toxic species in neuroblastoma cells. Numerical simulations of the reaction profiles (a) and nucleation rates (b) for a solution of 0.5 µM Aβ42 in the absence and presence of a 20-fold excess of bexarotene. Solid lines correspond to a control aggregation reaction in the absence of bexarotene, with reaction rate constants k2=1.106 1/M/s, k+=3.106 1/M/s and kn=1.104 1/M/s. Dotted lines show the behaviour in the presence of bexarotene, where the nucleation rate constant, kn, has been decreased to 1.102 1/M/s. A delay in the evolution of the total nucleation rate (i.e. of both primary and secondary nucleation) is observed. (c-f) Levels of activated caspase-3 as an indicator of the cytotoxic effects of Aβ42 species on a human neuroblastoma cell line (SH-SY5Y); the fluorescence values have been normalised (see Methods). Aliquots of 0.5 µM Aβ42, in the absence and in the presence of 10 µM bexarotene, were removed from the aggregation reaction at 0 h (c), 0.3 h (d), 4 h (e) and 7 h (f). Percentage differences between the fluorescence values of Aβ42 in the absence or in the presence of bexarotene (circles). These results show that detectable quantities of toxic Aβ42 species are formed in the presence of bexarotene only after 7 h incubation at 37° C., in agreement with a bexarotene-delay of the formation of Aβ42 toxic species.

Figure 6:
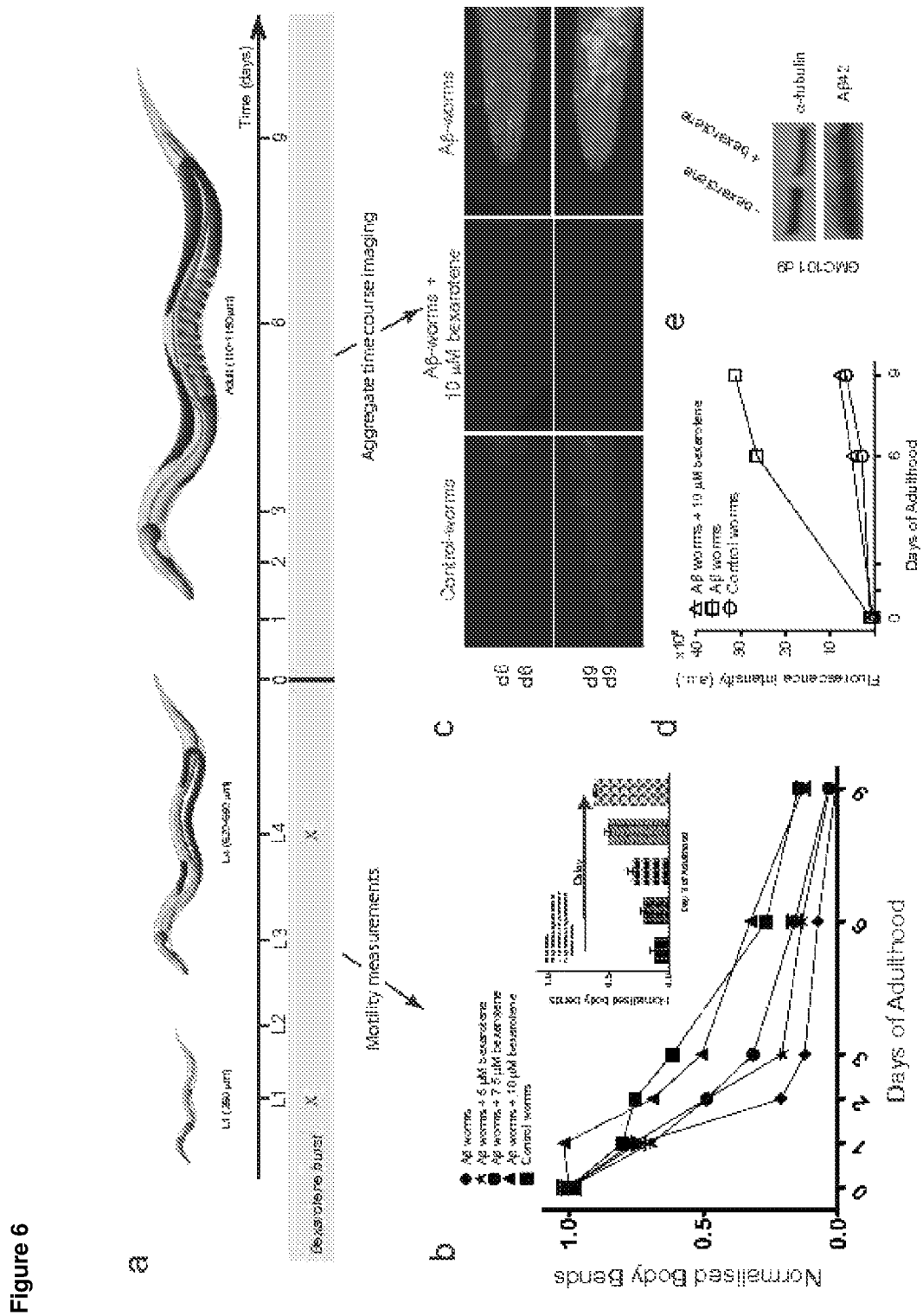

FIG. 6: Bexarotene restores the motility of *C. elegans* models of Aβ-mediated toxicity by preventing Aβ aggregation. (a) Experimental procedure for the measurement of the effects of bexarotene on the frequency of body bends and on the quantity of aggregates in *C. elegans* GMC101 (i.e. Aβ-worm) and CL2122 (i.e. control-worm) models. Note that bexarotene was given to the worms at larval stages L1 and L4. (b) Measurements of the effect of increasing concentrations of bexarotene ranging from 5 to 10 µM on the frequency of body bends in the Aβ-worm model. Normalized values with respect to day 0 are shown. The experimental data are shown for a single experiment but are representative in each case of three independent experiments. Complete recovery of the motility of the Aβ worm model can be observed at 10 µM bexarotene; the inset shows the dose-dependence of the effects of bexarotene on Aβ-worms at day 3 of adulthood. (c) In vivo imaging of aggregates stained using the amyloid-specific dye NIAD-4 in the absence and in the presence of 10 µM bexarotene; images from days 6 and 9 only are shown for clarity. (d) Time course of the reaction of amyloid aggregates formed in the Aβ-worm model in the absence and in the presence of 1 µM bexarotene. Quantification of fluorescence intensity was performed using ImageJ software (see Methods). In all panels, error bars represent the SEM. (e) Insoluble fraction of the protein extracts from *C. elegans* in the presence and in the absence of bexarotene with immuno-detection of Aβ and α-tubulin (see Methods).

Figure 7:
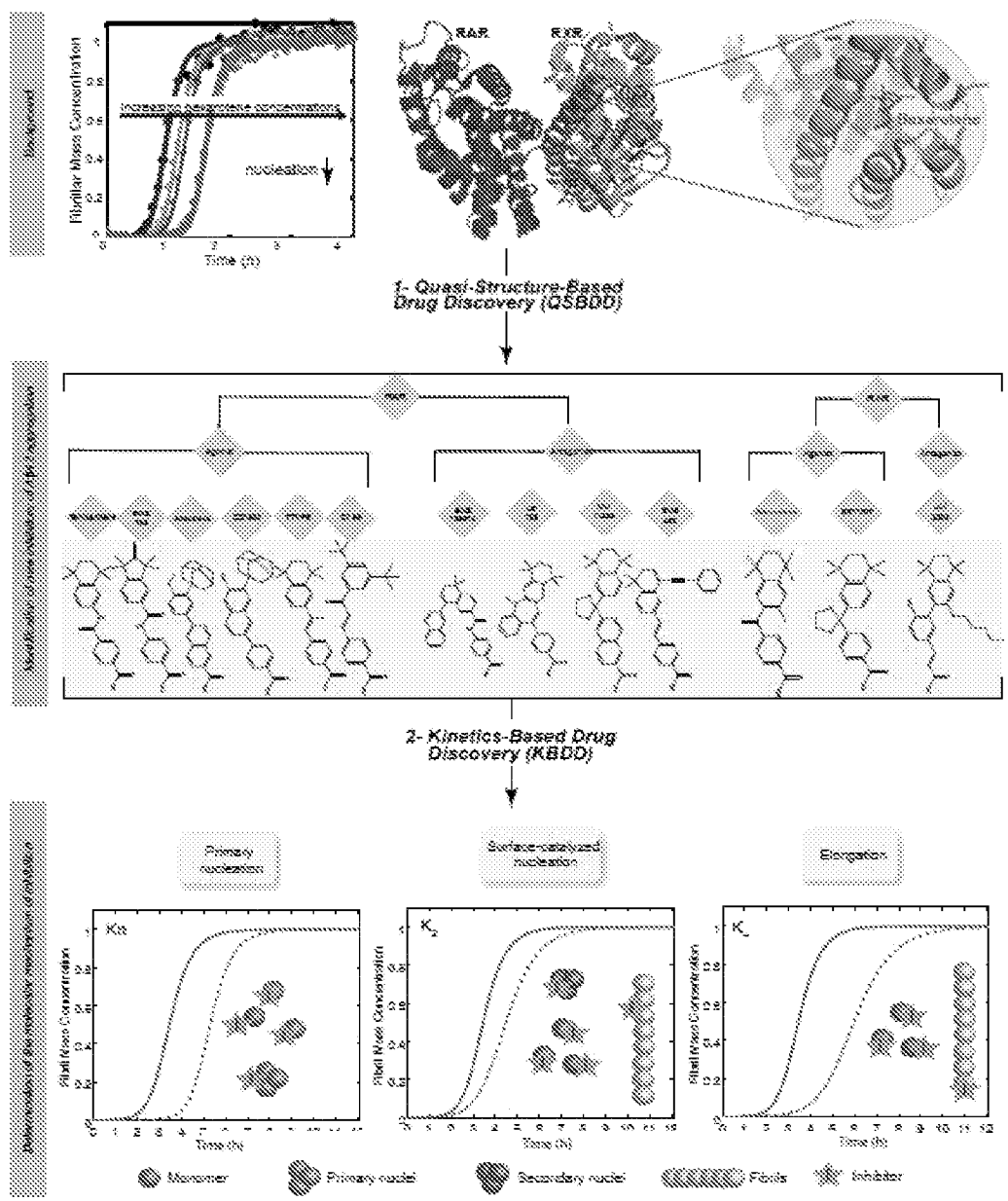

FIG. 7: Schematic illustration of the drug discovery strategy employed in Example II. The strategy consists of 2 main steps. (1) A quasi-structure-based drug discovery strategy (QSBDD) that consists in identifying potential molecules based on the structure of the initial receptor (i.e. RXR) of a pre-identified hit (i.e. bexarotene) that was shown to preferentially inhibit primary nucleation of Aβ42 aggregation. The rationale behind this strategy is that the instability and the transient nature of Aβ42 oligomers make their characterization and accordingly the structure-based drug development very challenging. Subsequently, all the agonists and antagonists of the RXR (i.e. the initial receptor of bexarotene) have been considered in this study based on the assumption that structural similarities occur between the binding pockets of RXR and Aβ42 oligomers. The structures of all molecules are shown. The strategy was also extended to include agonists and antagonists of RAR given the high structural similarities with RXR. In total, 13 molecules have been tested including bexarotene. The panel on the top left shows the kinetics of 5 µM Aβ42 aggregation (black) in the presence of increasing amounts of bexarotene (i.e. from 1- to 5-fold excess). The structure (PDB: 1XDK) of RAR is shown as a dimer with the RXR receptor. The RXR subunit is superimposed onto that of RXR with bexarotene in the binding pocket (PDB: 4K6I). A zoom into the binding pocket is also shown. (2) The second step consists of a kinetics-based drug discovery strategy (KBDD). This step assesses the effect of the small molecules at the microscopic level. Indeed, a molecule can bind to monomer, primary nuclei, secondary nuclei, fibrils or a combination of many species and accordingly affects different microscopic steps that can be characterized quantitatively using theoretical fitting of the aggregation kinetics. The solid lines correspond to the aggregation kinetics of Aβ42 without inhibitor. The dotted lines correspond to the kinetics of Aβ42 in the presence of inhibitor whereby this latter affects a single microscopic step.

Figure 8:
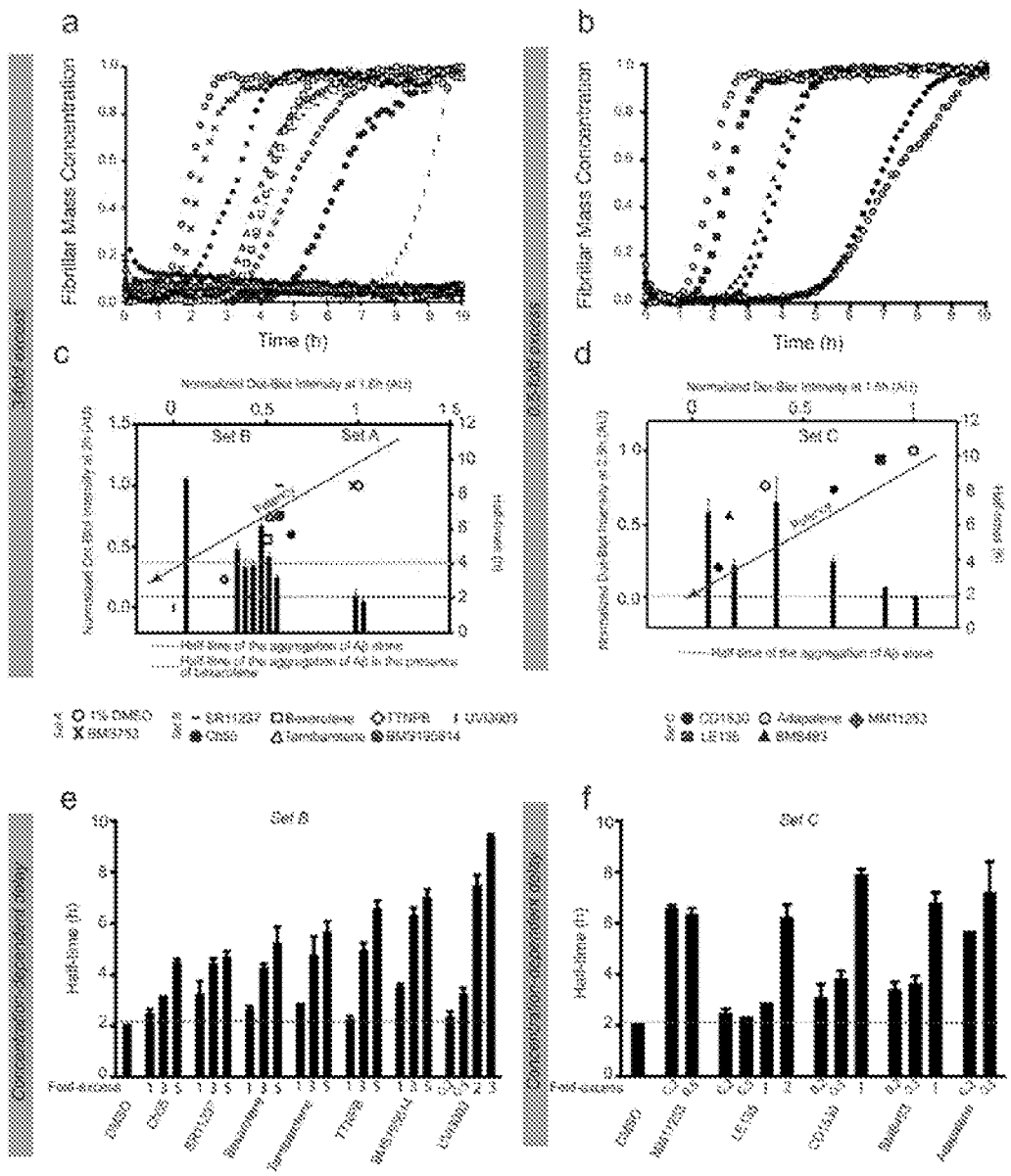

FIG. 8: RAR and RXR ligands affect Aβ42 aggregation to different extents. (a) Kinetic profiles of the aggregation of a 2 µM solution of Aβ42 in the absence and the presence of 3-fold excess of RAR and RXR ligands shown by different symbols. Note that Aβ42 did not aggregate within 10 hours in the presence of 5 out of the 13 molecules, shown as flat lines. (b) Kinetic profiles of 2 µM Aβ42 aggregation in the absence and the presence of sub-stoichoimetric quantities of the 5 molecules that are shown as flat lines in (a). (c) A plot showing, as histograms, the half-times of the aggregation reactions of Aβ42 from (a) and, as open circles, the correlation between the normalized dot-blot intensities with respect to that in the presence of 1% DSMO at 1.6 h and 2 h of the aggregation reaction. The molecules were separated into 2 Sets according to their potency that was evaluated based on the extent of the delay they induce in Aβ42 aggregation. Set A (highlighted in light blue) contains the molecule showing an effect that is similar to that of 1% DMSO (the half-time of Aβ42 aggregation in the presence of 1% DSMO is highlighted with a dotted black line). Set B (highlighted in light green) contains the molecules showing an effect similar or greater than that of bexarotene (the half-time of Aβµ2 aggregation in the presence of bexarotene is highlighted with a dotted red line). (d) A plot showing, as histograms, the half-times of the aggregation reactions of Aβ42 from (b) and, as open circles, the correlation between the normalized dot-blot intensities with respect to that in the presence of 1% DSMO at 1.5 h and 2.5 h of the aggregation reactions. The molecules were classified as Set C (highlighted in light orange). (e) A plot showing a dose-dependent effect of Set B molecules on the half-times of the aggregation reaction of Aβ42. (f) A plot showing a dose-dependent effect of Set C molecules on the half-times of the aggregation reactions.

Figure 9:
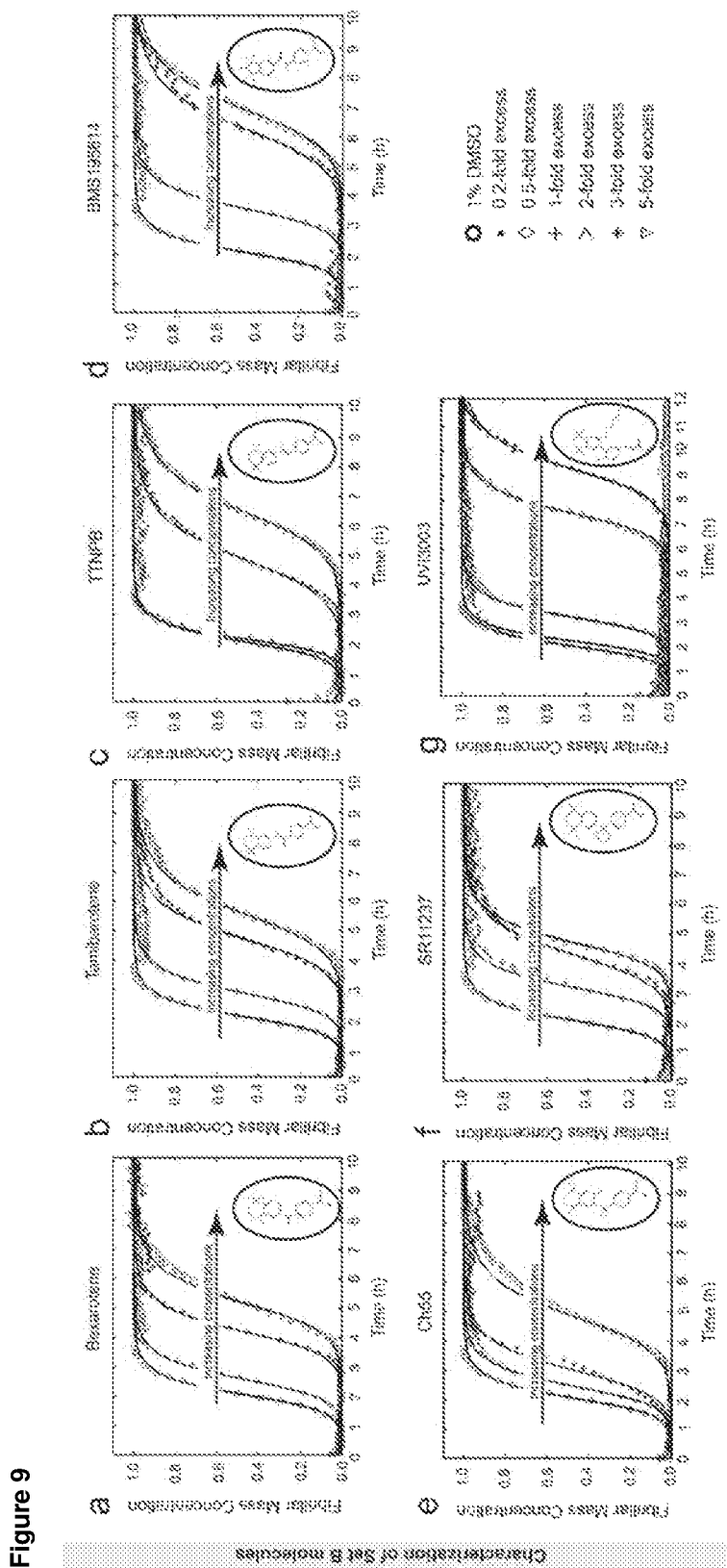

FIG. 9: Effect of Set B molecules on Aβ42 aggregation under quiescent conditions. (a-e) Kinetic profiles of the aggregation of a 2 µM solution of Aβ42 in the absence and the presence of either 1% DMSO (○) or 0.2-(•), 0.5-(◇), 1-(+), 2-(>), 3-(*), and 5-fold excess (▽) of bexarotene (a), tamibarotene (b), TTNPB (c), BMS195614 (d), Ch55 (e), SR11237 (f) and UVI3003 (g). The solid lines represent the integrated rate law for A! 42 aggregation fitted to the experimental data. All Set B molecules, the structures of which are shown in open circles, have induced significant delay in Aβ42 aggregation similarly to the results obtained with the dot-blot.

Figure 10:
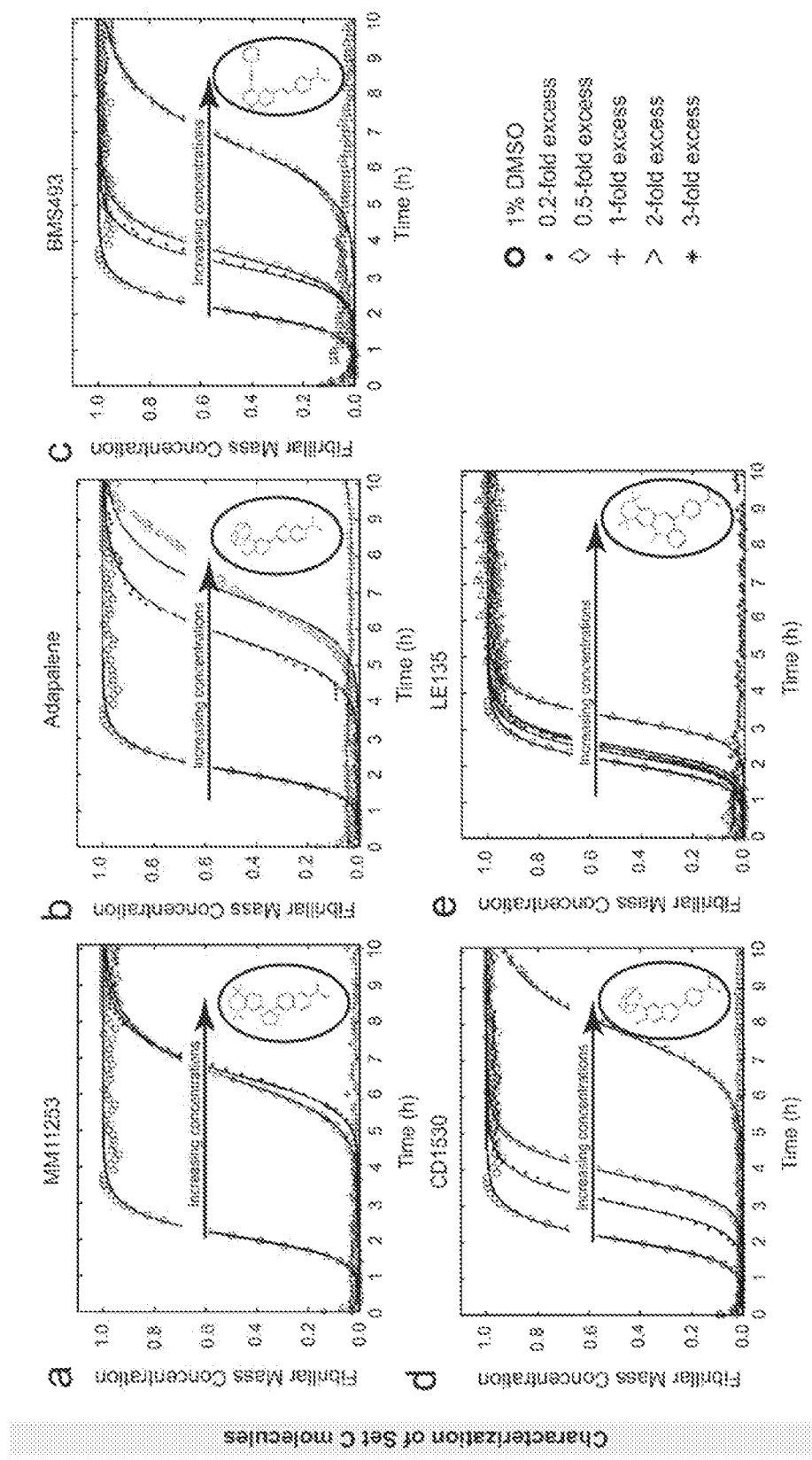

FIG. 10: Effect of Set C molecules on Aβ42 aggregation under quiescent conditions. (a-e) Kinetic profiles of the aggregation of a 2 µM solution of Aβ42 aggregation in the absence and the presence of either 1% DMSO (black) or 0.2-(red), 0.5-(cyan), 1-(blue), 2-(yellow), and 3-(green) of MM11253 (a), Adapalene (b), BMS493 (c), CD1530 (d) and LE135 (e). The solid lines represent the integrated rate law for A! 42 aggregation fitted to the experimental data. All Set C molecules, the structures of which are shown in open circles, have induced significant delay in Aβ42 aggregation at sub-stoichiometric quantities similarly to the results obtained with the dot-blot.

Figure 11:
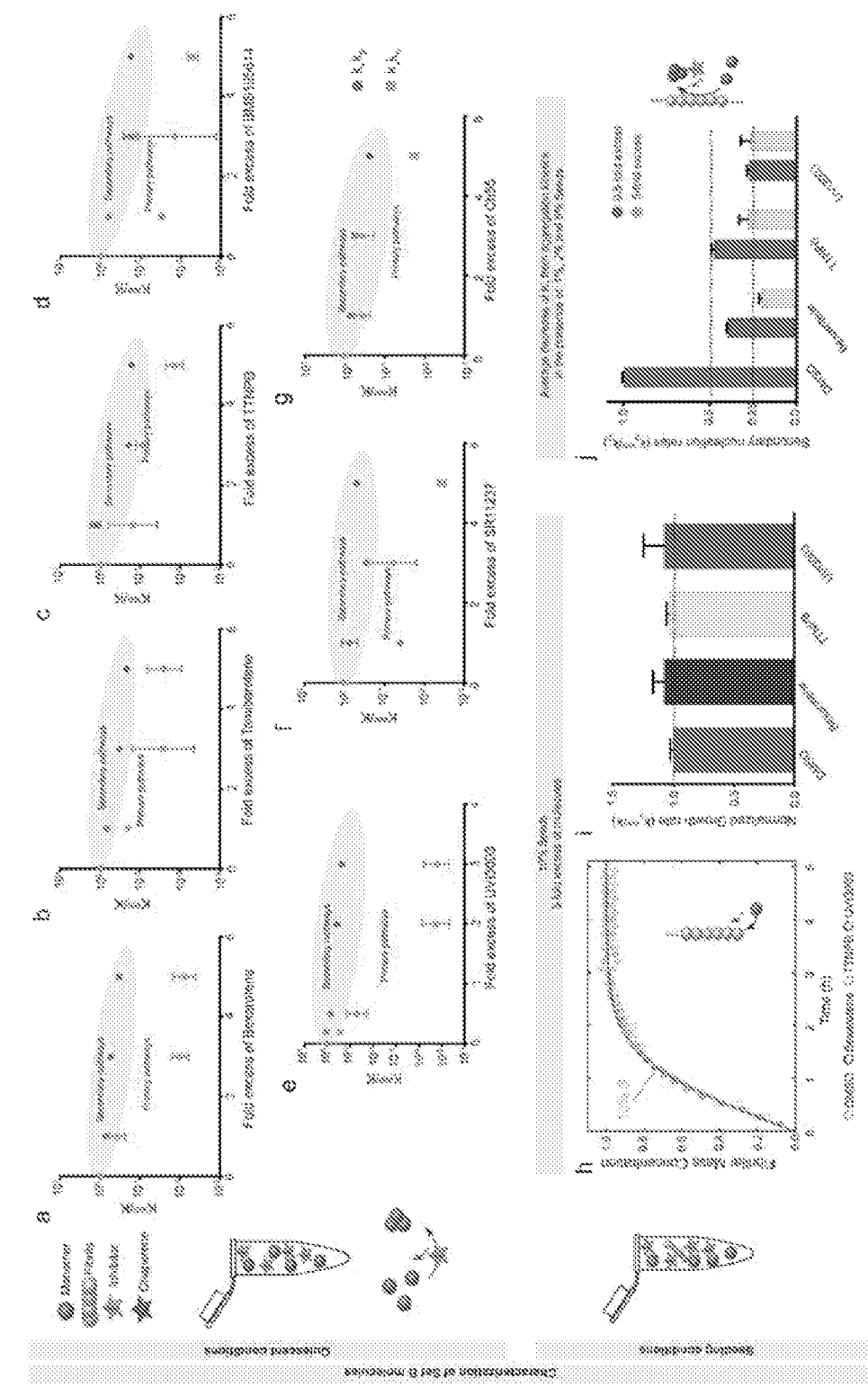

FIG. 11: Characterization of the effect of Set B molecules on Aβ42 aggregation. (a-g) Evolution of the apparent reaction rate constants, as obtained from the fitted aggregation reactions in FIG. 10, with increasing concentration of molecules (kn is the rate of primary nucleation, k+ of elongation and k2 of secondary nucleation, K represents in each case either knk+(primary pathways) or k2k+ (secondary pathways)). Note the slight decrease in secondary pathways, k2k+, when compared to the decrease in primary pathways, knk+, as the concentration of molecules is increased. (h-j) Effect of Set B molecules on Aβ42 aggregation under seeding conditions where primary pathways are negligible. (h) Kinetic profiles of the aggregation of a 2 µM solution of Aβ42 in the presence of 10% of pre-formed seeds in the absence or in the presence of 5-fold excess of bexarotene, TTNPB and UVI3003. Under these conditions, elongation of the fibrils is the dominant mechanism. (i) Normalized growth rate derived from the fitted curves in (h) in the presence of 10% of pre-formed seed fibrils. These results show that Set B molecules do not affect the elongation rates. (j) Effect of 0.5- and 5-fold excess of bexarotene, TTNPB and UVI3003 on the rates of surface-catalyzed secondary nucleation (k2). The rates were obtained from the aggregation kinetics of a 2 µM Aβ42 solution in the presence of 1%, 2% and 5% of pre-formed seeds (FIG. 13), where primary nucleation is negligible and surface-catalyzed secondary nucleation contributes to roughly 35%, 60% and 80%, respectively, of the total amount of fibrils formed. The quantitative parameters were obtained from the fitted curves in FIG. 13. The observed effect could only be due to decreasing the rates of surface-catalyzed secondary nucleation since elongation is not affected.

Figure 12:
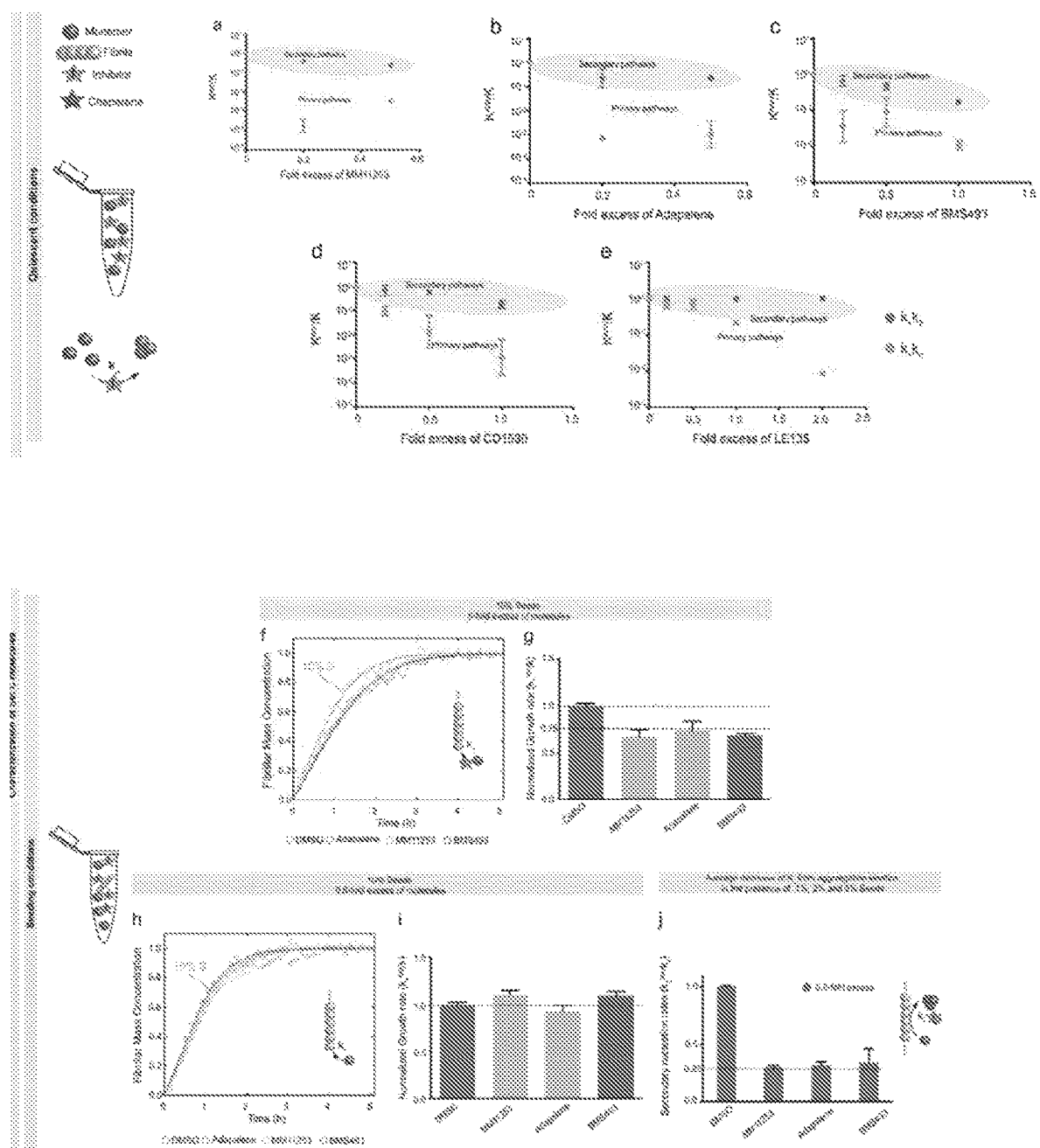

FIG. 12: Characterization of the effect of Set C molecules on Aβ42 aggregation. (a-e) Evolution of the apparent reaction rate constants, as obtained from the fitted aggregation reactions in FIG. 10, with increasing concentration of molecules (kn is the rate of primary nucleation, k+ of elongation and k2 of secondary nucleation, K represents in each case either knk+(primary pathways) or k2k+ (secondary pathways)). Note the slight decrease in secondary pathways, k2k+, when compared to the decrease in primary pathways, knk+, as the concentration of molecules is increased. (f-j) Effect of Set C molecules on Aβ42 aggregation under seeding conditions where primary pathways are negligible. (f) Kinetic profiles of the aggregation of a 2 µM solution of Aβ42 in the presence of 10% of pre-formed seeds in the absence or in the presence of 5-fold excess of MM11253, Adapalene and BMS493. Under these conditions, elongation of the fibrils is the dominant mechanism. (g) Normalized growth rate derived from the fitted curves in (f) in the presence of 10% of pre-formed seed fibrils. These results show that Set C molecules affect at 5-fold excess the elongation rates of Aβ42 aggregation. (h) Kinetic profiles of the aggregation of a 2 µM solution of Aβ42 in the presence of 10% of pre-formed seeds in the absence or in the presence of 0.5-fold excess of MM11253, Adapalene and BMS493. Under these conditions, elongation of the fibrils is the dominant mechanism. (i) Normalized growth rate derived from the fitted curves in (h) in the presence of 10% of pre-formed seed fibrils. These results show that Set C molecules at 0.5-fold excess do not affect the elongation rates of Aβ42 aggregation. (j) Effect of 0.5-fold excess of MM11253, Adapalene and BMS493 on the rates of surface-catalyzed secondary nucleation (k2). The rates were obtained from the aggregation kinetics of a 2 µM Aβ42 solution in the presence of 1%, 2% and 5% of pre-formed seeds (FIG. 15), where primary nucleation is negligible and surface-catalyzed secondary nucleation contributes to roughly 35%, 60% and 80%, respectively, of the total amounts of fibrils formed, respectively. The quantitative parameters were obtained from the fitted curves in FIG. 15. The observed effect could only be due to decreasing the rates of surface-catalyzed secondary nucleation since elongation is not affected at 0.5-fold excess.

Figure 13:
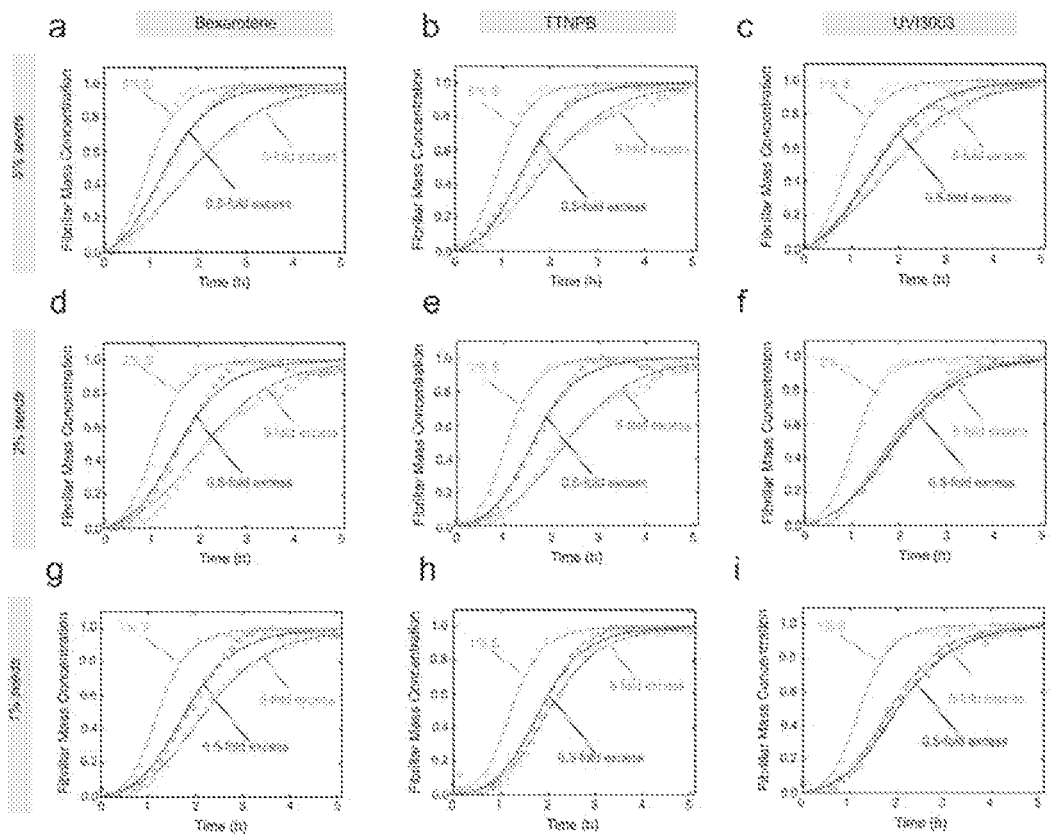

FIG. 13: Analysis of the effect of Set B molecules on Aβ42 aggregation kinetics in the presence of 1%, 2% and 5% of pre-formed seed fibrils. (a-c) Kinetic profiles of the aggregation of a 2 µM Aβ42 solution in the presence of increasing concentrations of pre-formed fibril seeds in the presence of either 1% DMSO, or 0.5- and 5-fold excess of bexarotene (a,d,g), TTNPB (b,e,h) and UVI3003 (c,f,i). Note the concentration-dependent effect of the Set B molecules on the aggregation kinetics.

Figure 14:
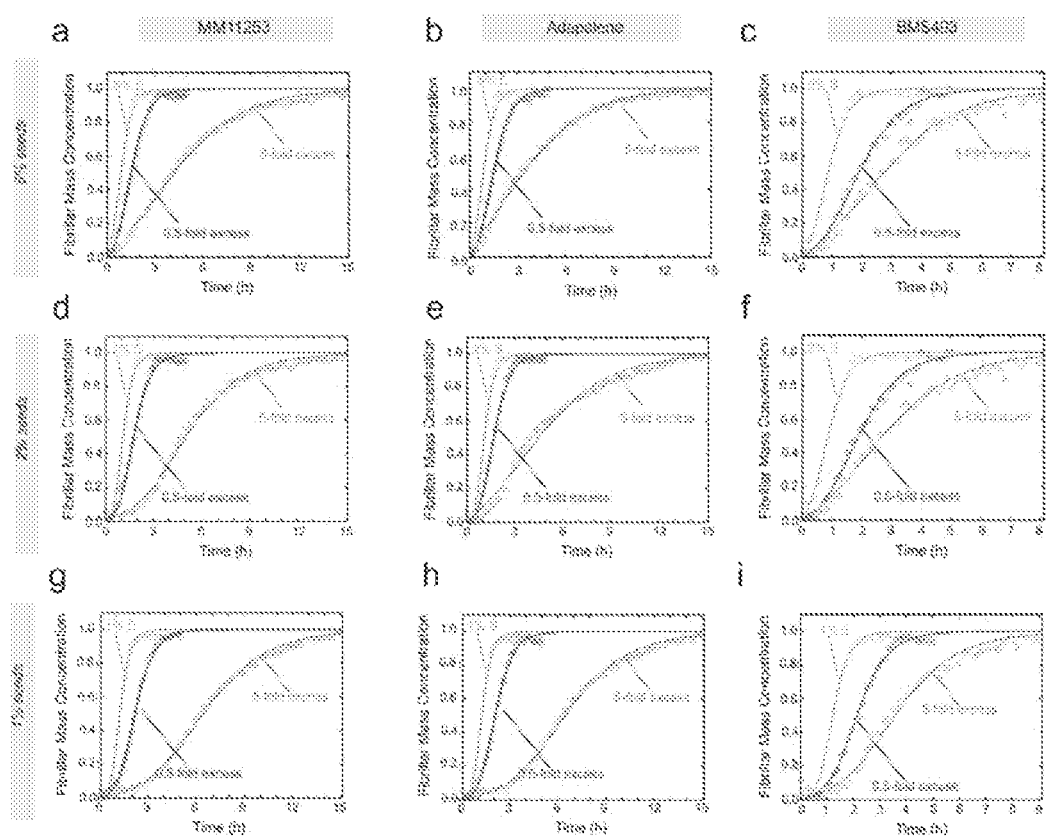

FIG. 14: Analysis of the effect of Set C molecules on Aβ42 aggregation kinetics in the presence of 1%, 2% and 5% of pre-formed seed fibrils. (a-c) Kinetic profiles of the aggregation of a 2 µM Aβ42 solution in the presence of increasing concentrations of pre-formed fibril seeds in the presence of either 1% DMSO, or 0.5- and 5-fold excess of MM11253 (a,d,g), Adapalene (b,e,h) and BMS493 (c,f,i). Note the concentration-dependent effect of the Set C molecules on the aggregation kinetics.

Figure 15:
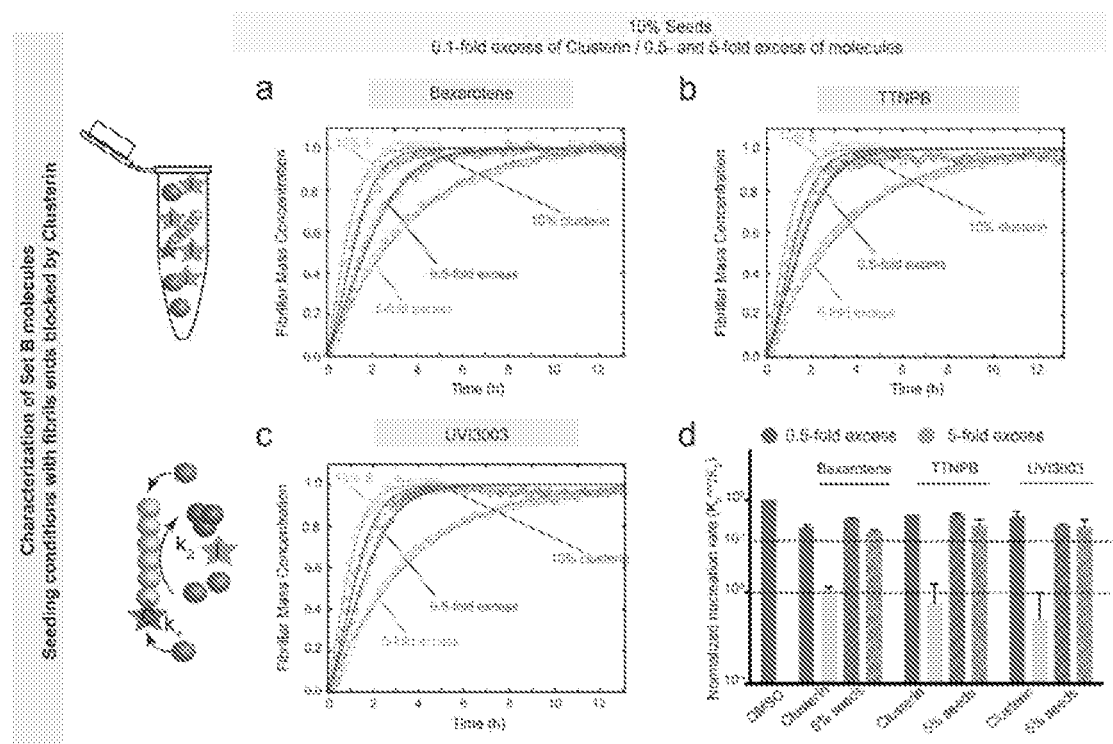

FIG. 15: Analysis of the effect of Set B molecules on the aggregation kinetics of Aβ42 in the presence of clusterin. (a-c) Kinetic reaction profiles of the aggregation of 2 µM Aβ42 solutions in the presence of 10% pre-formed seed fibrils, 10% clusterin and 0.5- and 5-fold excess of bexarotene (a), TTNPB (b) and UVI3003 (c). The rationale behind these experiments is to assess the effect of Set B molecules on surface-catalyzed secondary nucleation by blocking Aβ42 pre-formed fibril ends with clusterin. In the absence of clusterin, the dominant mechanim in the presence of 10% of pre-formed fibril seeds is elongation. The presence of 10% clusterin decreases the elongation rates by 60% and hence surface-catalyzed secondary nucleation is restored to 40%. Note the dose-dependent effect of Set B molecules on the aggregation kinetics when clusterin is added in agreement with an effect on surface-catalyzed secondary nucleation. (d) The apparent surface-catalyzed secondary nucleation reaction rates calculated from the fitted curves in (a-c) and compared to that in the presence of 5% of pre-formed fibril seeds.

Figure 16:
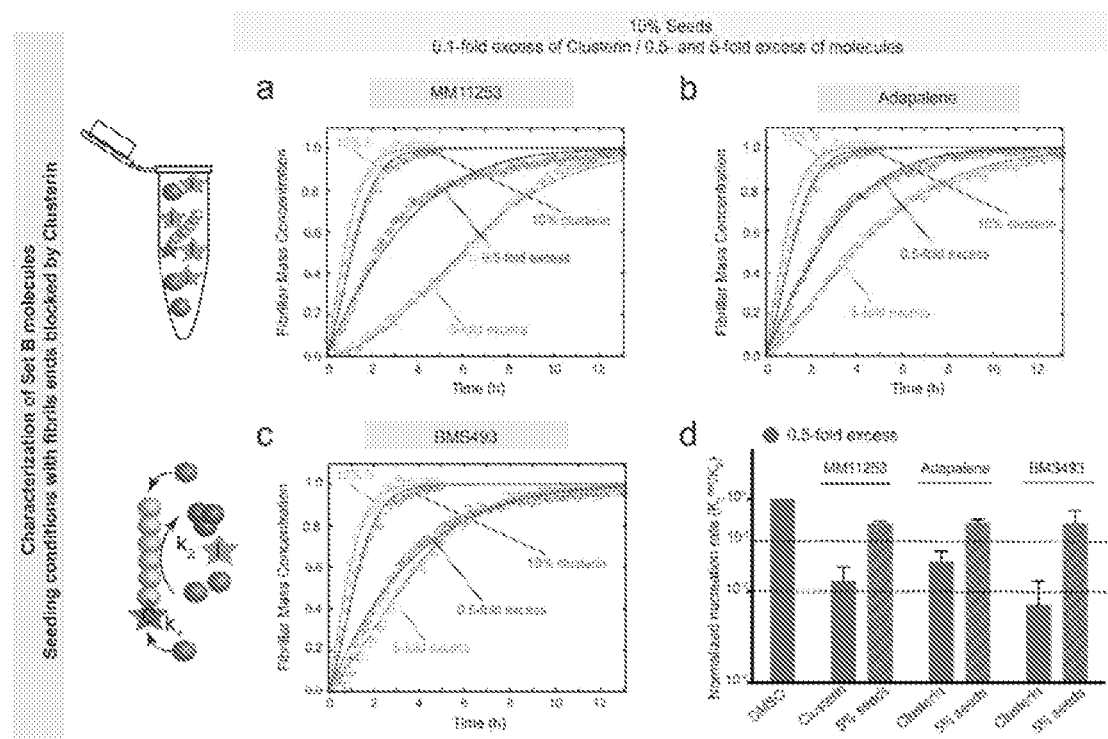

FIG. 16: Analysis of the effect of Set C molecules on the aggregation kinetics of Aβ42 in the presence of clusterin. (a-c) Kinetic reaction profiles of the aggregation of 2 μM Aβ42 solutions in the presence of 10% pre-formed seed fibrils, 10% clusterin and 0.5- and 5-fold excess of MM11253 (a), Adapalene (b) and BMS493 (c). The rationale behind these experiments is to assess the effect of Set C molecules on surface-catalyzed secondary nucleation by blocking Aβ42 pre-formed fibril ends with clusterin. In the absence of clusterin, the dominant mechanism in the presence of 10% of pre-formed fibril seeds is elongation. The presence of 10% clusterin decreases the elongation rates by 60% and hence surface-catalyzed secondary nucleation is restored to 40%. Note the dose-dependent effect of Set C molecules on the aggregation kinetics when clusterin is added in agreement with an effect on surface-catalyzed secondary nucleation. (d) The apparent surface-catalyzed secondary nucleation reaction rates calculated from the fitted curves in (a-c) and compared to that in the presence of 5% of pre-formed fibril seeds.

Figure 17A:
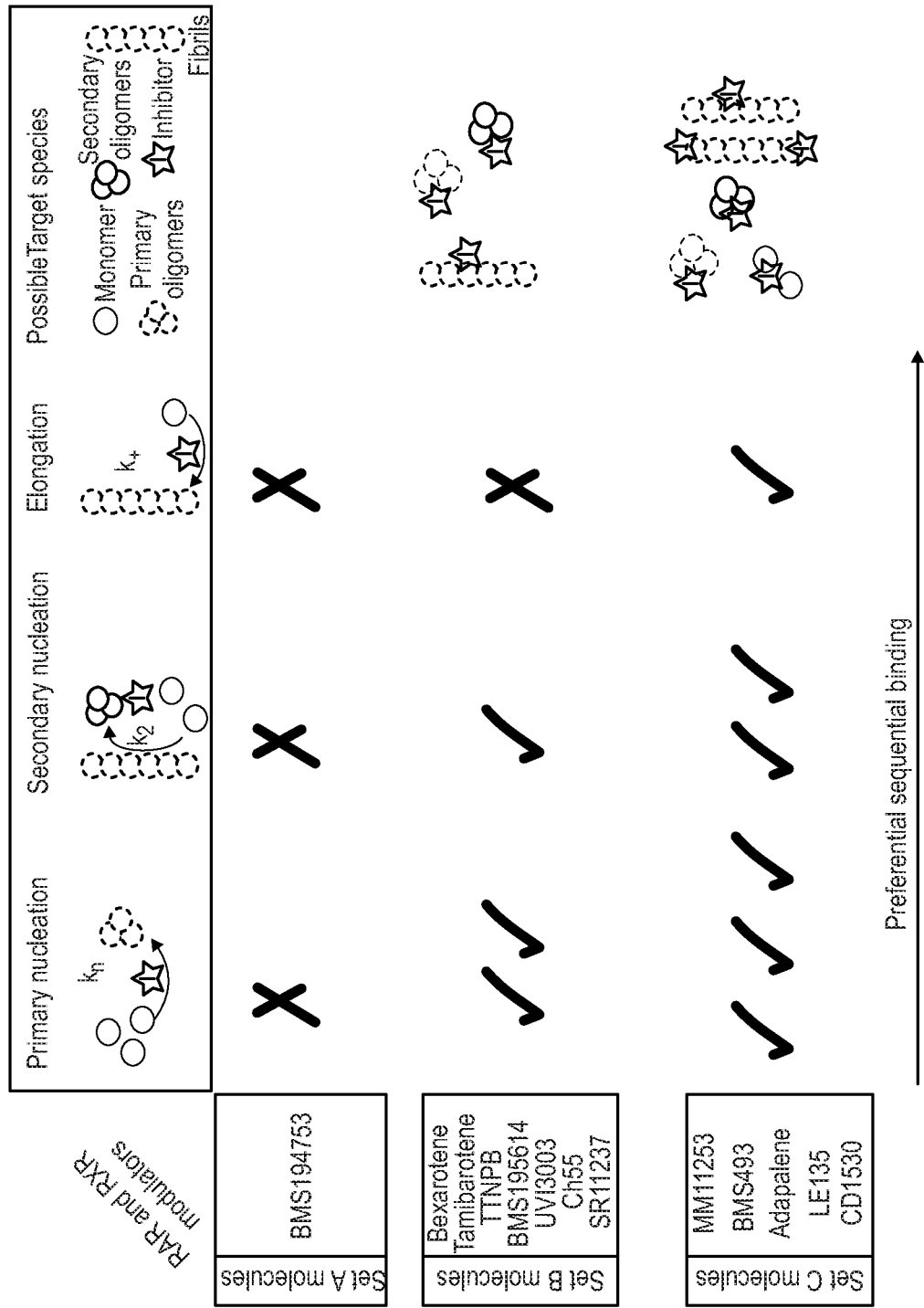
Figure 17B:
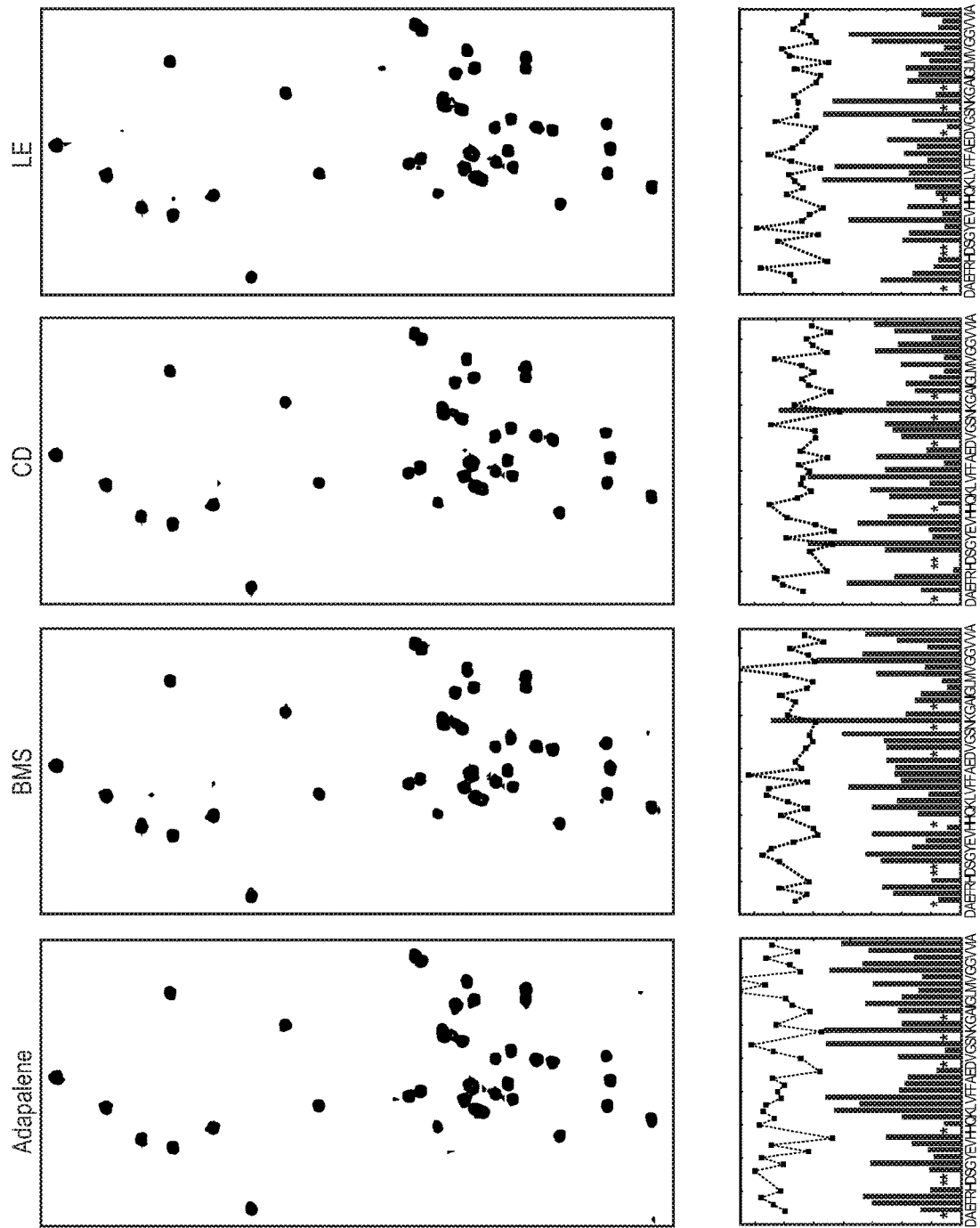
Figure 17C:
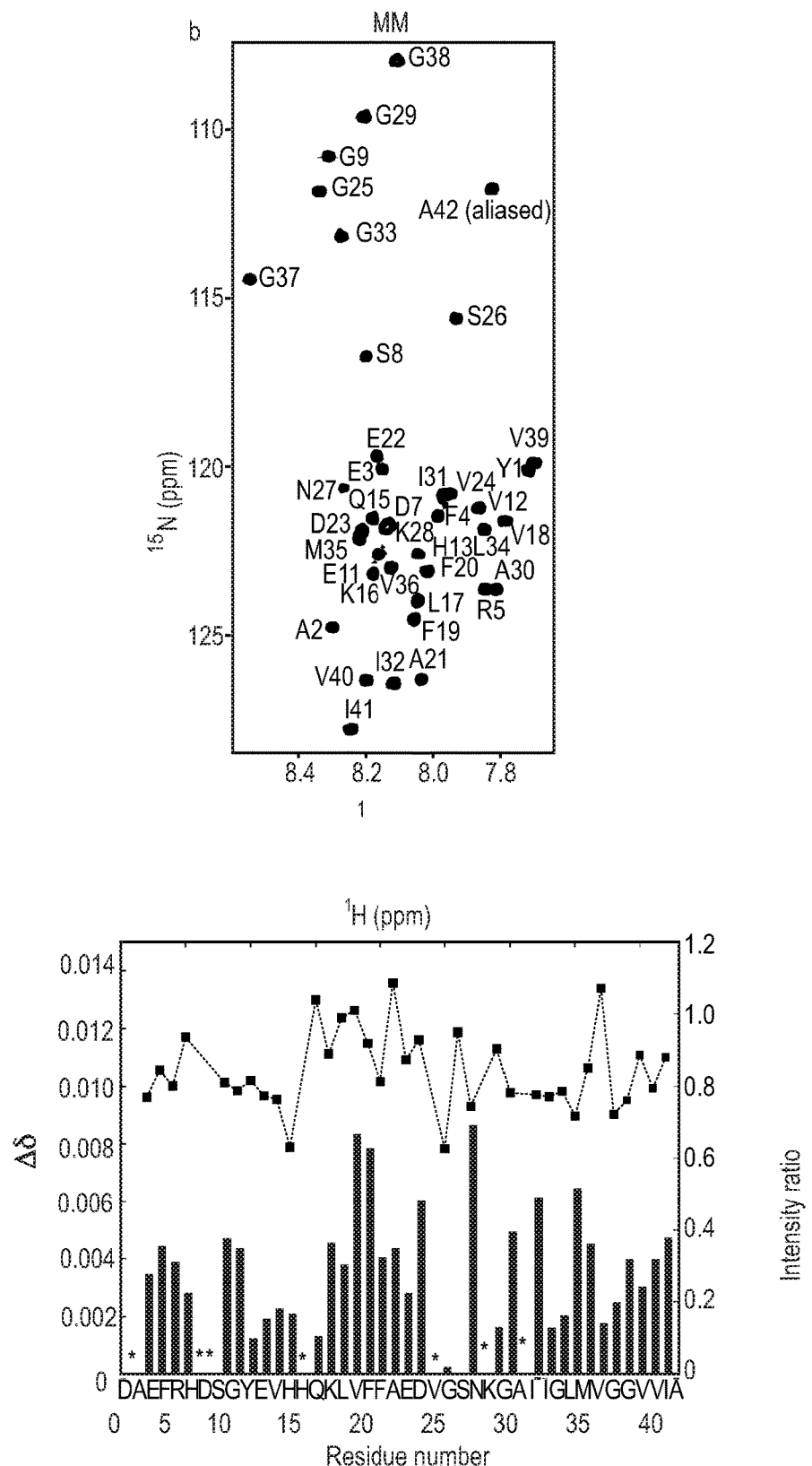

FIG. 17: Identification of the target species by the small molecules. (a) A table summarizing the effect of all molecules on the microscopic steps of Aβ42 aggregation and the target species, (b, c, top) Superimposition of the 1H-15N HSQC spectra of 25 μM monomeric $^{15}$N-Aβ42 in the presence of either 1% DMSO (black) or 1-fold excess of all Set C molecules and UVI (i.e. Set B). The spectra were obtained at a 1H frequency of 700 MHz and 278 K. (b, c, bottom) Chemical shifts (bar graph) and normalized intensity (dotted line) of 25 μM monomeric 1H-15N-Aβ42, as derived from the spectra (b, c), are similar to those observed for Aβ42 in the presence of 1% DMSO.

Figure 18:
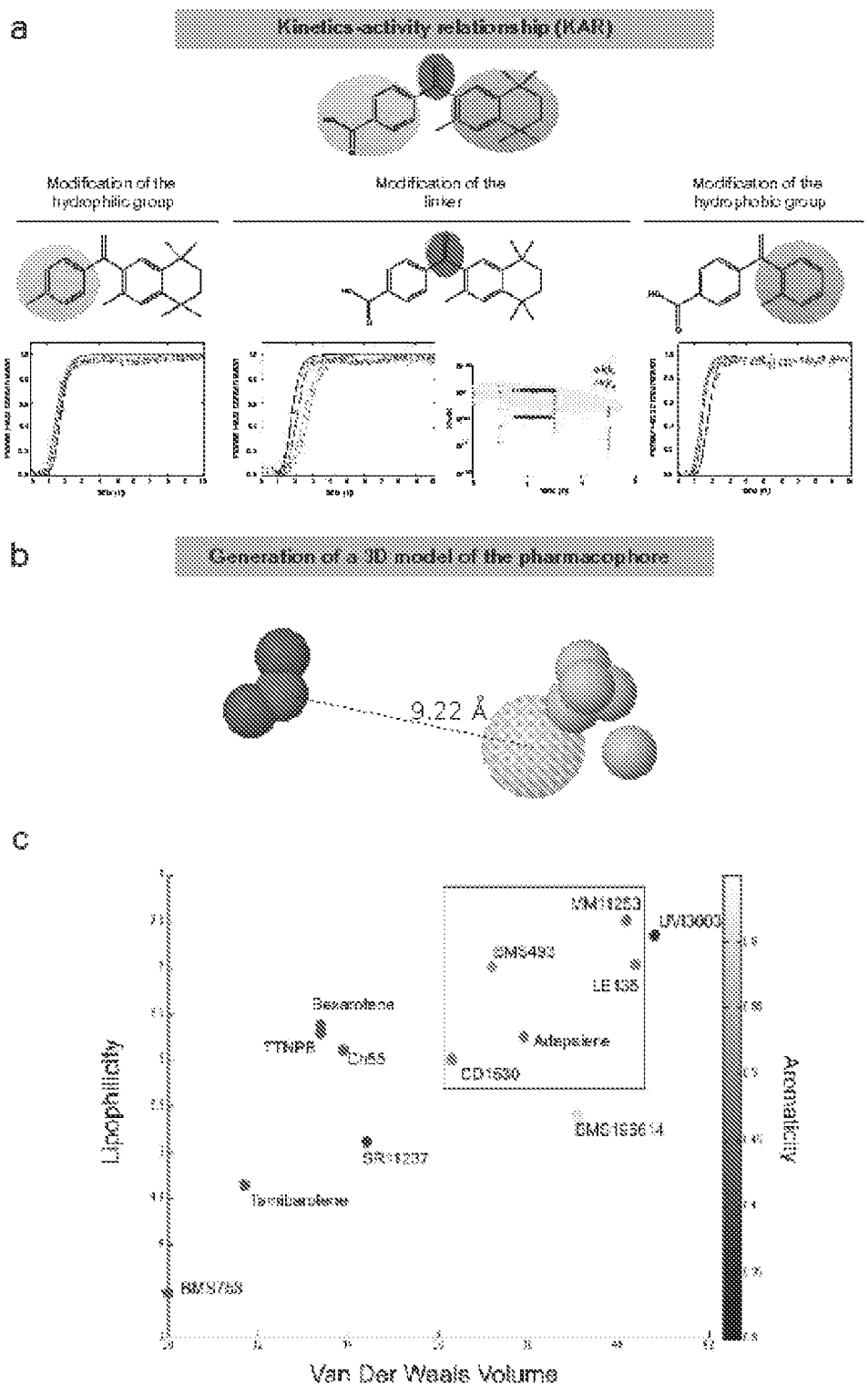

FIG. 18: Chemical analysis of the scaffolds of the small molecules. (a) Analysis of the contribution of three components of the structure of bexarotene on its effect on Aβ42 aggregation using chemical kinetics through a Structure-Kinetics Activity Relationship (S-KAR). (Top) Single substitutions were introduced into the scaffold of bexarotene in order to study the effect of the hydrophilic (left), hydrophobic (right) and linker (middle) components. (Bottom) Kinetic aggregation profiles of a 2 μM Aβ42 solution in the absence and the presence of the molecules bearing the single substitutions. (b) Generation of a pharmacophore from the alignment of all positive molecules. The pharmacophore consist of 2 main components: a hydrophobic moiety and a hydrophilic moiety separated by roughly 9.22 Å. (c) A plot showing the correlation between lipophilicity, Van Der Waals volume and aromaticity of the small molecules and their effect on the potency of the molecules.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The invention relates to a method for the identification of novel compounds that can act to inhibit aggregation of aggregation-prone proteins such as amyloid proteins. In particular, the invention relates to a method of identifying a compound that can inhibit one or more of the specific microscopic events, in particular primary and secondary nucleation, that underlie the process of protein aggregation.

As discussed in Arosio et al. (2014) (28) incorporated herein by reference, protein aggregation can be considered a multi-step process beginning with a nucleation step that generates small oligomers from a pool of monomeric proteins. Such oligomers are very reactive and metastable, and consequently will rapidly elongate into protofibrils and then fibrils by monomer addition. In most cases however, the aggregation rate is then exponentially accelerated by secondary nucleation processes, such as fibril fragmentation and surface catalysed nucleation, which form new reactive nuclei and result in a high level of apparent cooperativity in the nucleation process.

These microscopic processes and the effects of a target inhibitor on such processes can be analysed by studying the macroscopic kinetics of fibril formation. As explained by Arosio et al. (28) the microscopic kinetics of fibril formation follow a characteristic sigmoidal profile, in which a lag phase precedes a fast growth phase until a plateau is reached due to monomer depletion. Teasing out at which point in the aggregation process an inhibitor acts can be achieved by studying the kinetic profile in the absence and presence of the target inhibitor since inhibition of the different phases results in a different macroscopic aggregation profile. For example, a decrease in the primary nucleation rate generally increases the lag-time preceding the growth phase, as shown in FIG. 7. This information can be used to determine the efficacy of an inhibitor to inhibit protein aggregation and ultimately its potential therapeutic benefit in terms of disease prevention. While it is generally accepted that the more toxic species is the soluble oligomers, different inhibitors can have different effects on these oligomers. For example, inhibition of primary nucleation is predicted to only delay formation of the toxic soluble oligomers rather than decrease or suppress total oligomer load, whereas inhibition of secondary nucleation is predicted to decrease oligomer load. In contrast, inhibition of elongation is predicted to increase the total number of soluble, toxic oligomers. It is therefore clear that an inhibitor that can target at least primary nucleation and/or secondary nucleation is likely to be the most promising drug candidate.

While such information is useful, as mentioned above, to perhaps assess the potential therapeutic utility of an already identified inhibitor or to enable the rational selection of an inhibitor that can target a specific microscopic step of aggregation, such information alone does not allow the identification of new inhibitors and in particular inhibitors that specifically affect primary and/or secondary nucleation. The identification of new inhibitors that target these specific microscopic stages is made more challenging since primary and secondary nuclei are unstable, poorly abundant and only occur transiently during the aggregation process. These features preclude their structural characterisation using conventional biophysical approaches. The inventors have however developed a strategy which allows, (optionally) starting from an existing pre-identified hit, the identification of new inhibitors that can inhibit aggregation of an aggregation-prone protein.

Accordingly, in one aspect, there is provided a method for identifying an inhibitor of protein aggregation, wherein said protein is an aggregation-prone protein, the method comprising identifying a compound that binds to the same binding partner and/or a highly related binding partner as an already known or predicted inhibitor of said protein aggregation; wherein said at least one compound binds to the same binding site or pocket as the known or predicted inhibitor:

analysing the effect of the at least one further compound on the aggregation kinetics of the aggregation-prone protein; and selecting or identifying the at least one compound as an inhibitor if said compound affects the aggregation kinetics of the protein.

Preferably, the method comprises firstly identifying a known or predicted inhibitor of said protein aggregation and identifying and characterising a binding partner of the inhibitor.

In one embodiment, the inhibitors (known or predicted inhibitor and the at least one further compound) act as ligands, for example, but not limited to substrates, enzyme inhibitors, activators and neurotransmitters.

In one embodiment, protein aggregation can be divided into multiple microscopic steps and preferably at least three microscopic steps that are primary nucleation, secondary nucleation and elongation. Preferably, the known or predicted inhibitor inhibits at least one of these stages. Preferably the inhibitor to be identified also inhibits at least one of these steps. In a further embodiment at least primary and/or secondary nucleation are inhibited. In a further preferred embodiment, all steps of aggregation that is primary nucleation, secondary nucleation and elongation are inhibited.

By "primary nucleation" is meant the generation of an oligomer from monomeric subunits.

By "secondary nucleation" is meant fibril fragmentation and/or surface catalysed nucleation that forms a catalytic site for the generation of further toxic oligomer species.

By "elongation" is meant the addition of monomer units to oligomers to generate protofibrils and fibrils.

By "binding site or pocket" is meant a region on a protein or fragment thereof to which a ligand can form a chemical bond (i.e. by non-covalent bonding). Normally such sites are hydrophobic pockets in a protein that involve side chain atoms, or they can involve acceptors/donors of hydrogen bonds that can interact with polar parts of the ligand. Techniques for identifying a binding site are numerous in the technical field and would be well-known to the skilled person. The gold standard in this case is to use X-ray crystallography to determine the structure of the complex between the target protein and the drug. In this case, determining the binding site is not straightforward, again due to the same reason stated above, which is the instability and the transient nature of the bound structures that precludes their structural characterization and hence determining the exact binding site. This again supports the power of this technique; no such knowledge is required to identify further inhibitors, as explained below.

In a further embodiment of the above-described method, an initial inhibitor (the known or predicted inhibitor) can be identified using the following method. Starting from a small pool of about 10-100 known (or predicted) inhibitors that are reported in the literature to bind the aggregation-prone protein, a library of target fragments is generated. Preferably the molecular weight (MW) of such fragments is below 300 Da. These fragments are further screened to identify fragments with a low binding affinity to the aggregation-prone protein. Preferably, the $K_D$ of selected fragments from 100 micromolar to 10 millimolar range. In one embodiment, the selected fragments are screened against chemically related compounds in a known database. Preferably, the database is selected from ChEMBL (https://www.ebi.ac.uk/chembl/), PubChem (https://pubchem.ncbi.nlm.nih.gov/), ZINC (http://zinc.docking.org/) and/or DrugBank (http://www.drugbank.ca/). Alternatively, the database could be provided by a third party, such as a pharmaceutical partner or a contract research organisation. Optionally, the identified compounds are further screened for compounds that are FDA-approved, or alternatively, have completed a successful phase I trial. In either case a library of known (or predicted) inhibitors, FDA-approved or otherwise, is produced. In a further step, the effect of at least one known (or predicted) inhibitor from the inhibitor library is analysed to determine the microscopic stage of aggregation targeted by the inhibitor. Accordingly, in a further embodiment, the method comprises analysing the effect of the known (or predicted) inhibitor on the aggregation kinetics of the aggregation-prone protein, as described below. In a further embodiment, the method comprises selecting a known or predicted inhibitor that inhibits primary and/or secondary nucleation.

Once a small molecule has been identified, besides the above approach (also called Quasi-Structure-Based Drug Discovery' (QBSDD)—see Example II) that is proposed here, a virtual screening of databases, such as the one described above, could be performed using the scaffold of the inhibitor.

In one embodiment, a highly-related binding partner has a similar structure and/or a similar or identical biological function and/or interacts with the same ligand to the binding partner. For example, the retinoid receptors RAR and RXR both bind to retinoid. In one embodiment, a similar structure may mean that the binding partners share at least one conserved structural domain or motif. Alternatively, the binding partners may share a high nucleotide or amino acid sequence identity, preferably at least at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity or similarity to each other.

As explained in Arosio et al. (28) the kinetic analysis is first applied to elucidate the aggregation mechanism of the aggregation-prone protein under consideration in the absence of any compounds. The analysis is then repeated in the presence of the at least one compound to identify the effect of the compound on the kinetic profile.

Accordingly, in a preferred embodiment, analysing the effect of the at least one compound of the aggregation kinetics of said aggregation-prone protein comprises producing a kinetic profile of said protein in the absence and presence of the compound. The compound is then identified as an inhibitor if it causes a shift or change in the relative rate of the kinetic profile. As discussed above, preferably, the kinetic profile is a sigmoidal curve, wherein said curve comprises at least a lag phase preceding a growth phase and which is followed by a plateau representing primary nucleation, secondary nucleation and elongation respectively, and wherein the at least one compound alters at least one of these phases. In one embodiment, the inhibitor increases the length of the lag phase, decreases the steepness of the growth phase and/or delays the onset of the plateau.

In one embodiment of the described method the kinetic profile is produced using the following equation:

The time evolution of the total fibril mass concentration, M(t), is described by the following integrated rate law $$\frac{M(t)}{M(\infty)} = 1 - \alpha \left( \frac{B_+ + C_+}{B_+ + C_+ e^{kt}} \frac{B_- + C_+ e^{kt}}{B_- + C_+} \right)^{\frac{k_\infty^2}{kk_\infty}} e^{-k_\infty t} \quad (1)$$

where the kinetic parameters $B_\pm$, $C_\pm$, $\kappa$, $\kappa_\infty$ and $\tilde{\kappa}_\infty$ are functions of the two combinations of the microscopic rate constants $k_+ k_2$ and $k_n k_2$, where $k_n$, $k_+$ and $k_2$ are the primary nucleation, elongation and secondary nucleation rate constants, respectively.

A molecule can interfere with the aggregation process by inhibiting one or more of the individual microscopic reactions. We can identify the microscopic events that are inhibited by the chemical compound by applying the above equation to describe the macroscopic aggregation profiles after performing highly reproducible experiments, and comparing the set of microscopic rate constants $k_+ k_2$ and $k_n k_2$ required to describe the time evolution of the fibril formation in the absence and presence of the small molecule.

In the methods described above, an "aggregation-prone protein" can be considered to be any amyloid protein. By "amyloid protein" it is meant a protein that is deposited as an insoluble fibril, mainly in the extracellular spaces of organs and tissues as a result of sequential changes in protein folding that result from a condition known as amyloidosis. An amyloid fibril protein occurs in tissue deposits as rigid, non-branching fibrils, approximately 10 nm in diameter that bind Congo red and exhibit green, yellow or orange birefringence when the stained deposits are viewed by polarisation microscopy.

When isolated from tissues and analysed by X-ray diffraction, the fibrils exhibit a characteristic β diffraction pattern (54). "Amyloid protein" is also a standard term of art and the proteins that are classified as amyloid can be found in the ISA Amyloid Fibril Protein Nomenclature List, which is incorporated herein by reference.

In a preferred embodiment, the amyloid protein is selected from Aβ42, α-synuclein, tau, huntingtin, atrophin-1, ataxin (1, 2, 3, 6, 7, 8 12, 17), amylin, prion protein, (pro)calcitonin, atrial natriuretic factor, apoliprotein AI, apoliprotein AII, apoliprotein AIV, serum amyloid, medin, (apo) serum AA, prolactin, transthyretin, lysozyme, β-2 microglobulin, fibrinogen α chain, gelsolin, keratopthelin, β-amyloid, cystatin, ABriPP immunoglobulin light chain AL, immunoglobulin heavy chain, S-IBM, islet amyloid polypeptide, insulin, lactadherin, kerato-epithelium, lactoferrin, tbn, leukocyte chemotactic factor-2, AbriPP, ADanPP, lung surfactant protein, galectin 7, corneodesmosin, lactadherin, kerato-epitelium, odontogenic ameloblast-associated protein, semenogelin 1 and enfurvitide. Preferably the amyloid protein is selected from Aβ42, α-synuclein, tau and huntingtin. More preferably, the amyloid protein is Aβ42.

In another aspect of the invention, there is provided a protein aggregation inhibitor obtained or obtainable by the above method.

In a further aspect of the invention there is provided a method of producing a pharmacophore against aggregation of a aggregation-prone protein, the method comprising
providing at least one inhibitor of protein aggregation;
generating an inhibitor scaffold from the at least one inhibitor;
introducing at least one chemical substitution into at least one component of the inhibitor scaffold, and optionally the inhibitor, and analysing the effect of the at least one chemical substitution of the aggregation kinetics of said aggregation-prone protein, wherein analysing the effect on aggregation kinetics comprises producing a kinetic profile (as described herein) of said protein in the absence and presence of an inhibitor scaffold or inhibitor having at least one of said chemical substitutions, and identifying a substitution as a positive result if said substitution causes a shift in the kinetic profile (a "shift" is as described herein); and
producing a pharmacophore against aggregation of a aggregation-prone protein by aligning the positive results from the kinetic assay.

The inhibitor in the first step of the method may be identified by the methods described herein. The second step of the method may in addition use a known or predicted inhibitor (as described above for the methods of identifying an inhibitor of protein aggregation) in generating the inhibitor scaffold.

The term "pharmacophore" is defined as the ensemble of steric and electronic features that is necessary to ensure the optimal supramolecular interactions with a specific biological target and to trigger (or block) its biological response. In the present context, the inventors have developed a method of producing a pharmacophore against an aggregation-prone protein (i.e. inhibits aggregation of the aggregation-prone protein). In one embodiment, the aggregation-prone protein is an amyloid protein, preferably Aβ42. Once generated, the pharmacophore produced by the above-described method has numerous uses. For example, the pharmacophore can be used to screen a chemically diverse library of compounds to identify compounds that share similar physiochemical features that fit with the pharmacophore and are therefore potential inhibitors of protein aggregation. There is therefore also provided a method of screening a library of compounds using the pharmacophore identified by the above-described method to identify at least one further inhibitor of protein aggregation, wherein the protein is an aggregation-prone protein.

A pharmacophore can be identified using various medicinal chemical computational software codes. The inventors have, in this case, firstly generated 3D conformations of each compound (i.e. inhibitor) using CORINA (55) (incorporated herein by reference). CORINA (Coordinates) is an automatic 2D-to-3D conversion software which generates three-dimensional coordinates for the atoms of a molecule purely from its constitution of a molecule (as expressed through a connection table or linear code). By combining mono-centric fragments with standard bond lengths and angles, together with appropriate dihedral angles (determined through statistical analysis of conformational preferences in small molecule crystal structures), CORINA is able to derive robust and reliable results, even for complexes with large rings or metals. Accordingly, in one embodiment, an inhibitor scaffold can be derived by generating a 3D conformation of the inhibitor using programs known in the art, for example, CORINA.

These conformations were subsequently used as input for the PharmaGist software (56) (incorporated herein by reference). PharmaGist elucidates 3D pharmacophores from a set of drug-like molecules that are known to bind to a target receptor. It performs this via an indirect method, where the structure of the receptor is unknown, and the only available information is a set of ligands that have been observed to interact with the receptor. One of the most challenging aspects for these indirect methods is deriving the specific conformation of the ligand, especially when it is interacting with the receptor. PharmaGist addresses this through multiple flexible alignments of the ligands, where the flexibility is treated explicitly and in a deterministic manner in the alignment process. This allows a fast and reliable detection of pharmacophores, with the ability to detect outlier molecules, as well as to find common pharmacophores within subset of molecules. The algorithm employed by PharmaGist involved using one ligand as a pivot to align the rest of the ligands. Pairwise alignments were calculated through superimposition of features, and all the alignments were combined into multiple alignments. Significant subsets of pivot features that were matched by as many pairwise alignments as possible were identified. In this case, the features of the pharmacophore generated were matched by all the ligands that were used as inputs.

For the particular scaffold of the RAR/RXR modulators, it could be noted that modifications to the linker component allowed the compound to retain its inhibitory activity, though to a different extent. For example, a slight increase in the linker length with an alkene position change (TTNPB from bexarotene) resulted in an increase in inhibitory activity, while changing the alkene substituent to an amide linkage did not result in significant activity change. On top of that, it was observed that extension strategies involving adding more hydrophobic groups to the hydrophobic region of the compound were also useful to enhance its inhibitory activities. A swap in the position of the linker of tamibarotene, with a greatly extended hydrophobic region, resulted in a substantial increase in primary nucleation inhibitory activity of compound BMS195614.

The same effect could also be observed following a minor alkyl substituent change in the linker of TTNPB with a far more extended hydrophobic region which gave compound BMS493. Accordingly, a chemical substitution can encompass any type of substitution known to the skilled person, wherein such substitution is introduced into any region of the inhibitor scaffold. Indeed, a chemical substitution in any given inhibitor scaffold can be any substitution that retains the inhibitory activity of the compound and that can be made from steric observations, charge interactions and so on. Such suitable substitutions can be easily determined by the skilled person.

An aggregation-prone protein is defined above.

In a further embodiment, there is provided a pharmacophore obtained or obtainable by the above-described method.

In another aspect of the invention, there is provided a pharmacophore that inhibits aggregation of Aβ42, wherein the pharmacophore comprises nine features: two hydrogen bond acceptors and one negatively charged feature at the terminal end which represents the carboxylic acid group, one aromatic feature attached to five hydrophobic features. A horizontal distance of 9.22 Å is also estimated from the terminal hydrophobic group to the other polar terminus, as shown in FIG. 18b.

In a further aspect of the invention there is provided a method for screening a library of compounds to identify an inhibitor of protein aggregation, wherein the protein is an aggregation-prone protein, the method comprising screening said library and identifying compounds with at least a high lipophilicity (Ghose-Crippen Octanol-Water coefficient) and high bulkiness (Van Der Waals Volume), wherein said lipophilicity is between 4 and 8 and more preferably between 4.6 and 7.4 and even more preferably between 4.648 and 7.351, and wherein said bulkiness is between 30 and 41, more preferably between 31.7 and 40.81, In a further embodiment, the method further comprises additionally screening for compounds with a high aromaticity ratio, wherein preferably said ration is between 0.3 and 0.7, more preferably between 0.35 and 0.61, and even more preferably between 0.353 and 0.606. Preferably, the inhibitor is an inhibitor of Aβ42 aggregation. Even more preferably, the compounds are RAR/RXR modulators.

In one embodiment, protein aggregation can be divided into at least three microscopic stages that are primary nucleation, secondary nucleation and elongation, and wherein said inhibitor inhibits at least primary and secondary nucleation. In this embodiment, such inhibitors can be used to inhibit primary nucleation, secondary nucleation and elongation.

In a further aspect of the invention, there is provided a method for treatment of Alzheimer's disease, the method comprising administering to a patient in need thereof a retinoid receptor modulator, wherein the modulator is selected from the group consisting of a retinoid A receptor (RAR) agonist, selected from Adapalene, CD 1530, TTNPB and Ch55, a retinoid A receptor (RAR) antagonist selected from BMS195614, LE135, MM11253 and BMS493, a retinoid X receptor agonist that is SS11237 and a retinoid X receptor antagonist that is UVI3003.

In another aspect of the invention, there is provided a retinoid receptor modulator for use in the treatment of Alzheimer's disease, wherein the modulator is selected from the group consisting of a retinoid A receptor (RAR) agonist, selected from Adapalene, CD 1530, TTNPB and Ch55, a retinoid A receptor (RAR) antagonist selected from BMS195614, LE135, MM11253 and BMS493, a retinoid X receptor agonist that is SS11237 and a retinoid X receptor antagonist that is UVI3003.

In a yet further aspect of the invention, there is provided the use of a retinoid receptor modulator in the manufacture of a medicament for use in the treatment of a Alzheimer's disease, wherein the modulator is selected from the group consisting of a retinoid A receptor (RAR) agonist, selected from Adapalene, CD 1530, TTNPB and Ch55, a retinoid A receptor (RAR) antagonist selected from BMS195614, LE135, MM11253 and BMS493, a retinoid X receptor agonist that is SS11237 and a retinoid X receptor antagonist that is UVI3003.

In one embodiment, the structure of the retinoid receptor modulator is as follows:

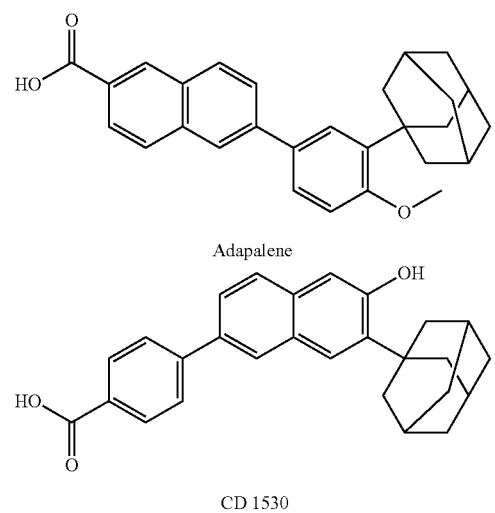

Adapalene

CD 1530

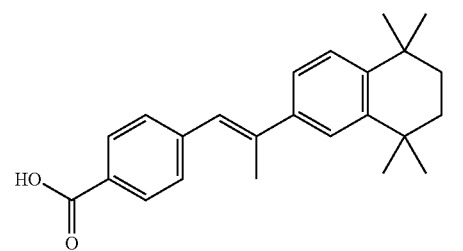

TTNPB

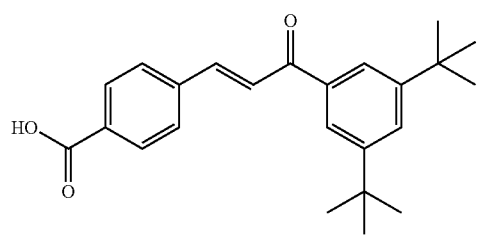

Ch55

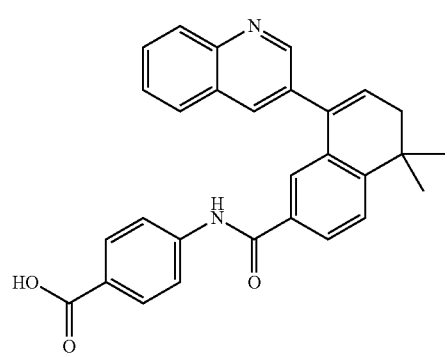

BMS195614

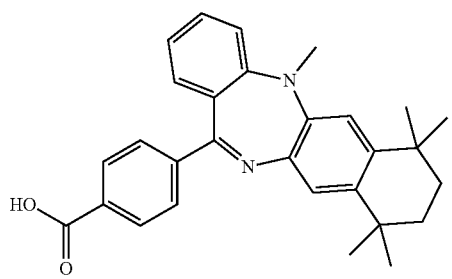

LE135

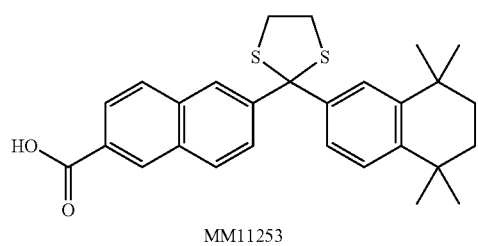

MM11253

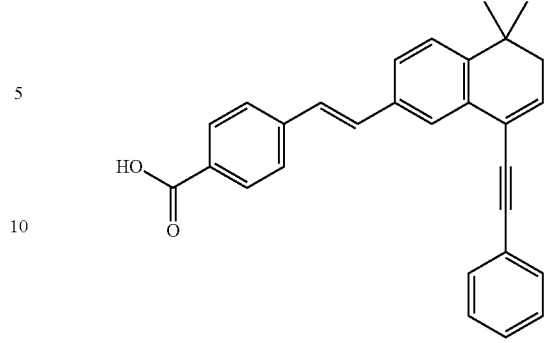

BMS493

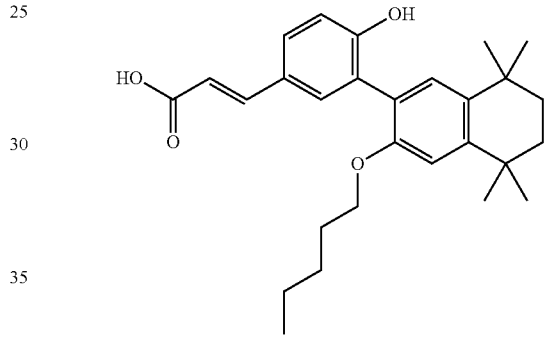

SR11237

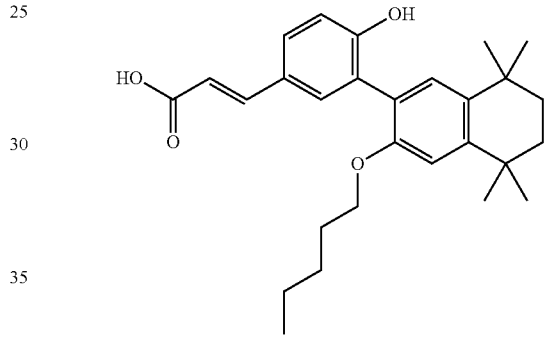

UVI3003

'Treatment' refers to the management of a patient through medical or surgical means. The treatment improves or alleviates at least one symptom of Alzheimer's disease and is not required to provide a cure. The treatment can further encompass any known treatment for Alzheimer's disease including donepezil, rivastigmine, galantamine and memantine.

In another aspect, the invention relates to pharmaceutical composition comprising a therapeutically active amount of a retinoid receptor modulator and a pharmaceutically acceptable carrier. In one embodiment, the modulator is selected from the group consisting of a retinoid A receptor (RAR) agonist, selected from Adapalene, CD 1530, TTNPB and Ch55, a retinoid A receptor (RAR) antagonist selected from BMS195614, LE135, MM11253 and BMS493, a retinoid X receptor agonist that is SS11237 and a retinoid X receptor antagonist that is UVI3003. In a further aspect, the modulator inhibits at least one stage of protein aggregation, preferably primary and secondary nucleation (as defined above) and more preferably primary nucleation, secondary nucleation and elongation.

Pharmaceutically acceptable carriers and/or diluents may also include any and all solvents, dispersion media, coatings, antibacterials and/or antifungals, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated.

In a further aspect of the invention there is provided a method for the inhibition of aggregation of an aggregation-prone protein, wherein the aggregation-prone protein is Aβ42, the method comprising administering, preferably to a patient in need thereof a protein aggregation inhibiting amount of a retinoid receptor modulator, wherein the modulator is selected from the group consisting of a retinoid A receptor (RAR) agonist, selected from Tamibarotene, Adapalene, CD 1530, TTNPB and Ch55, a retinoid A receptor (RAR) antagonist selected from BMS195614, LE135, MM11253 and BMS493, a retinoid X receptor agonist selected from SS11237 and Bexarotene and a retinoid X receptor antagonist that is UVI3003. In an alternative embodiment, the modulator added to, for example, a cell culture containing an aggregation-prone protein, to inhibit protein aggregation in vitro.

In another aspect, there is provided the use of a retinoid receptor modulator to inhibit the aggregation of an aggregation-prone protein, wherein said aggregation-prone protein is Aβ42, and wherein the modulator is selected from the group consisting of a retinoid A receptor (RAR) agonist, selected from Tamibarotene, Adapalene, CD 1530, TTNPB and Ch55, a retinoid A receptor (RAR) antagonist selected from BMS195614, LE135, MM11253 and BMS493, a retinoid X receptor agonist selected from SS11237 and Bexarotene and a retinoid X receptor antagonist that is UVI3003.

For completeness, the structure of Tamibarotene and Bexarotene is as follows:

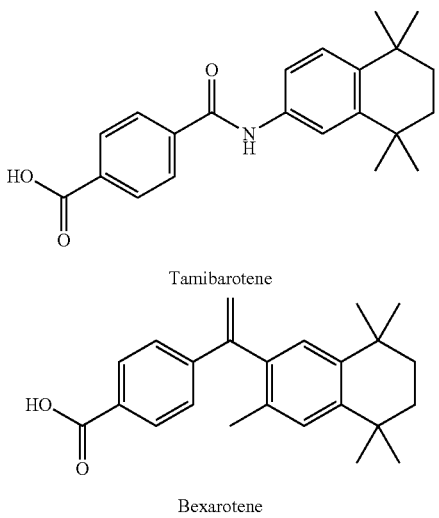

Tamibarotene

Bexarotene

In one embodiment of the above-described method or use, protein aggregation can be divided into at least three microscopic steps that are primary nucleation, secondary nucleation and elongation, and the retinoid receptor modulator inhibits at least one of these steps. In a preferred embodiment, the retinoid receptor modulator inhibits primary and/or secondary nucleation. In a further preferred embodiment, the modulator inhibits all microscopic stages, and the modulator is selected from MM11253, BMS493, Adapalene, CD 1530 and LE135.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The foregoing application, and all documents and sequence accession numbers cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The invention is further described in the following non-limiting examples.

EXAMPLES

Example I

In this example we describe a drug discovery strategy to identify new drugs that target the aggregation of Aβ42. This strategy consists of four main steps (FIG. 1). First, a fragment-based approach is applied in order to identify small molecules that could interfere with Aβ aggregation (FIG. 1, step 1). Fragment-based drug design approaches are based on the screening of a limited number of small molecules to identify fragments with low binding affinities typically with $K_D$ values in the high micromolar to millimolar range (33, 34). When combined together, some of these fragments result in molecules containing multiple favorable interactions that bind more tightly than the initial fragments to the target of interest. To implement this strategy we generated a set of 164 fragments derived from 88 compounds reported in the literature to interact with Aβ42. These fragments were then screened for chemically related compounds in four small-molecule databases (ChEMBL, PubChem, ZINC and DrugBank), resulting in the identification of 16,850 molecules. This fragment-based library contains 386 FDA-approved drugs, which have the potential to be effective candidates for pre-clinical lead development. Indeed, such an approach offers exciting opportunities to repurpose existing licensed therapeutic compounds for use in AD with the benefit of providing a more rapid route to the clinic than through novel drug discovery approaches (35, 36).

To test this strategy, we selected two compounds from this library with different chemical scaffolds, bexarotene and tramiprosate (FIG. 1, step 1). Tramiprosate, which has been unsuccessful in phase 3 AD clinical trials (identifier: NCT0088673), was reported in preclinical development to bind soluble Aβ species, to maintain them in a nonfibrillar form, to decrease Aβ-induced neurotoxicity and to reduce amyloid plaques and cerebral levels of Aβ in mice (37). By contrast, bexarotene is still in phase 2 clinical trials (identifier: NCT01782742). This small molecule is a retinoid X receptor (RXR) agonist approved by the FDA for the treatment of cutaneous T-cell lymphoma and has shown an ability to restore cognitive function to some degree in AD (38-44). Although this activity has been reported to be associated with an enhancement of apolipoprotein-E levels, and thus of Aβ42 clearance, conflicting reports have been published and the detailed mechanism of action remains uncertain (38-44). Indeed, this molecule has also been reported to compete with cholesterol for binding to Aβ42, thus inhibiting its cholesterol-induced oligomerization (45).

The next step in our general strategy is to apply chemical kinetics in order to elucidate the mechanism of aggregation of the protein of interest (FIG. 1, Steps 2). In the specific case of Aβ42, as mentioned in the Introduction, we have recently provided a comprehensive description of the mechanism (32). The kinetic analysis is then repeated in the presence of selected compounds to identify the microscopic events that are specifically inhibited and hence to define the species with which the compound interacts (FIG. 1, step 3). Indeed, a potential drug candidate could bind to monomers, oligomers, or fibril surface or ends, and therefore different microscopic steps could be affected. While sequestration of monomers could result in a decrease in the rates of all microscopic events (i.e. $k_N$ for primary nucleation, $k_2$ for secondary nucleation and k+ for elongation), sequestering oligomers is expected to affect $k_N$ and $k_2$. On the other hand, targeting fibrils could decrease either $k_+$ or $k_2$ depending on whether inhibitors bind to fibril ends or surfaces, respectively (28).

Finally, we evaluate the observed effect of the molecules on the formation of toxic species in vivo (FIG. 1, step 4). The inhibition of specific microscopic steps in Aβ42 aggregation is expected to have different effects on the generation of toxic oligomers (28). More specifically, inhibiting primary nucleation will strongly delay the aggregation reaction and should not affect the total load of toxic oligomers generated during the reaction. However, an increase or a decrease in the number of toxic oligomers is anticipated to be the result of the suppression of either elongation or secondary nucleation, respectively (28). These two latter processes represent interchangeable pathways as inhibiting elongation is expected to redirect the aggregation reaction towards secondary nucleation, which will consequently increase the number of toxic oligomers, and vice versa (28).

Bexarotene, but not Tramiprosate, Delays Aβ42 Fibril Formation

To investigate the effects of the two small molecules selected for this study on the individual microscopic steps underlying the aggregation process of Aβ42, we carried out the global analysis of the aggregation profiles acquired at different concentrations of both Aβ42 and each of the two compounds in turn (FIG. 2). We monitored Aβ42 fibril formation in vitro in the absence and the presence of tramiprosate and of bexarotene using a highly reproducible ThT based protocol described previously (31). Unlike earlier reports (37), we observed no effects of tramiprosate on Aβ42 aggregation even when present in 20-fold excess (FIG. 2a).

By contrast, we observed a progressive delay in Aβ42 aggregation with increasing concentrations of bexarotene (FIG. 2b,c). The scaling of the half-times in such reaction profiles as a function of the total protein concentration follows a power law whose exponent contains important information about the microscopic events underlying the macroscopic aggregation behaviour (32). In the presence of bexarotene, although the lag times of the aggregation reaction increase as the concentration is increased, the scaling exponent remains unaffected. This result suggests that, under these conditions, bexarotene delays the aggregation reaction by inhibiting primary nucleation but does not affect the relative contributions of primary and secondary nucleation to the overall aggregation reaction.

These experiments show that the effect of bexarotene on Aβ42 aggregation is substantial. The addition of a 4-fold excess of bexarotene to a 2 µM sample of Aβ42 increased the time to half-completion of the aggregation reaction compared to that of Aβ42 alone by a factor of two (i.e. 2.30±0.02 h for Aβ42 alone and 4.50±0.06 h for Aβ42 in the presence of bexarotene) (FIG. 3a). To probe this effect further, and to exclude any possible interference of bexarotene on ThT binding to Aβ42 fibrils and hence on the resulting fluorescence, we monitored fibril formation under conditions where ThT was not present by removing aliquots of solution at a series of different time points and measuring the extent of fibril formation using atomic force microscopy (AFM) and immunochemistry (FIG. 3b-d). Fractions were collected throughout the entire reaction in order to monitor as completely as possible the events during the three phases of Aβ42 aggregation (i.e. lag, growth and saturation). AFM images show that after 2.1 h, fibrillar structures are visible in the absence of bexarotene but not in its presence, thus providing independent evidence for a bexarotene-induced delay of fibril formation (FIG. 3b). These results were extended (FIG. 3c) by probing the quantities of Aβ42 at nine different time points during the aggregation using either sequence-sensitive W0-2 or fibril-sensitive OC primary antibodies (see Methods). W0-2 antibodies recognize the sequence spanning residues 4-10 (i.e. the N-terminus) that is not likely to be involved in the hydrophobic core of any aggregated species and thus bind to all types of Aβ species. W0-2 antibodies indicated the presence of similar quantities of Aβ42 at the different time points during its aggregation reaction (FIG. 3c, upper panel), whereas fibril-specific OC antibodies that recognize only fibrillar species (FIG. 3c, lower panel) showed, in agreement with the kinetic analysis and the AFM images, a delay of 2 h in the time required for half-completion of the aggregation process.

We probed further the quantity of Aβ42 converted into fibrils by comparing the intensities of the dots to a dot-blot assay that was performed on a range of concentrations between 4 and 0.1 µM of Aβ42 fibrils using the OC-fibril antibodies (FIG. 3d). Fibrils were collected after incubation for 3 h of a freshly prepared 4 µM solution of monomeric Aβ42 (FIG. 3d, lower panel) and then the solution was diluted to yield 12 samples with concentrations ranging from 4 µM to 0.11 µM (FIG. 3d, lower panel). Analysis of the dot-blot data indicated that the quantities of fibrils formed at the reaction half-times of the 2 µM sample Aβ42 in the absence and in the presence of bexarotene (FIG. 3c, lower panel, time points 6 and 7) were indeed closely similar to those formed during the aggregation reaction of an Aβ42 sample of 1 µM concentration, consistent with no interference from ThT on the aggregation reaction (FIG. 3d, lower panel).

Bexarotene Specifically Inhibits the Primary Nucleation of Aβ42 Aggregation

We then carried out a quantitative analysis of the effects of bexarotene by matching the aggregation profiles based on the rate laws derived from a master equation that relates the macroscopic time evolution of the quantity of fibrils to the rate constants of the different microscopic events (28, 29). In this approach, the aggregation profiles in the presence of the inhibitor are described by introducing into the rate laws suitable perturbations to each of the microscopic rate constants evaluated in the absence of the inhibitor. The modifications of the rate constants required to describe the aggregation profiles in the presence of different concentrations of inhibitor are then indicative of the specific process affected by the presence of the compound. The aggregation profiles of 5 μM Aβ42 in the presence of concentrations of bexarotene in the range of 5-25 μM show that the experimental data are extremely well described when the primary nucleation rate constant, $k_n$, is specifically decreased.

By contrast, the experimental data are not consistent with predictions made by altering the rate constants of secondary nucleation or of elongation, $k_2$ and $k_+$, respectively (FIG. 4a-c). The data therefore reveal that, under these conditions, bexarotene specifically modifies the primary nucleation pathway (i.e. $k_n k_+$) with no (or very little) detectable effect on secondary pathways in the aggregation reaction (i.e. $k_2 k_+$) (FIG. 4d).

To strengthen these conclusions further, we carried out an additional series of measurements of the aggregation kinetics of Aβ42 under conditions where the primary nucleation step was bypassed by the introduction of preformed fibrils (i.e. seeds) to the reaction mixture. In such a situation, the contribution of primary nucleation to the reaction kinetics is negligible, as the conversion of soluble peptide into mature fibrils is greatly accelerated by secondary nucleation and elongation reactions promoted by the seeds (22). In the presence of 10% fibril seeds, where elongation of the pre-formed fibril seeds is the dominant mechanism, no effect was observed on the aggregation kinetics of 2 μM Aβ42 even at a 10-fold excess of bexarotene (FIG. 4e), while the corresponding aggregation process under unseeded conditions was completely inhibited for 15 h. Furthermore, we also measured the aggregation kinetics of a 2 μM sample of Aβ42 in the presence of 5% of pre-formed fibril seeds. Under these conditions, primary nucleation is completely bypassed whereas both surface-catalyzed secondary nucleation and elongation significantly contribute to the overall kinetics (FIG. 4f). These experiments show a concentration-dependent bexarotene-induced delay that compares to a decrease in the rate of surface-catalyzed secondary nucleation (FIG. 4g, h). These findings show that, while the elongation of fibrils is essentially unaffected by bexarotene, this compound has a large and highly selective effect on the nucleation of Aβ42, with the effect being more pronounced towards primary rather than secondary nucleation.

The observation that bexarotene inhibits Aβ42 aggregation by specifically perturbing both primary and secondary nucleation could in principle result from the interaction of bexarotene with Aβ42 monomers, or with primary and secondary oligomers or indeed with both monomers and oligomers (FIG. 4f). However, binding to monomers would affect the rates of all the microscopic steps in the overall reaction under the conditions studied here (28), enabling us to conclude that bexarotene specifically interacts primarily with Aβ42 oligomers. This conclusion is further supported by NMR spectroscopy measurements, where no significant perturbations of the chemical shifts could be observed in the HSQC spectra of 25 μM $^{15}$N-labeled monomeric Aβ42 before and after the addition of a 5-fold excess of bexarotene, indicating that binding to the monomeric form of Aβ42 is likely to be negligible. Furthermore, these findings provide novel insights into the structural features of primary and secondary oligomers of Aβ42 suggesting that primary and secondary nuclei may possess similar structural features, and hence can interact with bexarotene in a similar manner, and that the same residues of Aβ42 may be involved in both, primary and secondary nucleation events.

Targeting Primary Nucleation Delays the Formation of Toxic Species of Aβ42

We next explored whether or not the delay in Aβ42 fibril formation resulting from inhibiting primary nucleation by bexarotene could be associated with a delay in the formation of neurotoxic species, as the perturbation of different microscopic steps in Aβ42 aggregation has different effects on the rate of generation of toxic oligomers (28). Thus, for example, decreasing the primary nucleation rate is expected to delay the overall aggregation reaction but not to affect the total number of toxic oligomers generated during the reaction (28). An increase or decrease in the number of toxic oligomers is, however, likely to result from the suppression of elongation or secondary nucleation, respectively (28).

To examine this issue, we performed numerical simulations of the total rate of formation of oligomers, from both primary and secondary processes in the aggregation reaction of a 0.5 μM solution of Aβ42 in the absence and presence of a 20-fold excess of bexarotene (see Methods). Since bexarotene targets preferentially primary nucleation, it is expected to delay the entire aggregation process, i.e. to delay the generation of toxic species without necessarily decreasing the amount of the toxic species. Based on our previous findings, primary nucleation is a very rapid process that is directly bypassed by secondary nucleation once a small but critical concentration of seeds has been formed (22). We have therefore used the lowest concentration of Aβ42 at which aggregation can be observed (31), and monitored its aggregation in the presence of high concentrations of bexarotene in order to inhibit as strongly as possible the primary nucleation step. The simulations show that by delaying the primary nucleation of Aβ42 in the presence of bexarotene a delay in the formation of Aβ42 oligomers occurs but without decreasing the total amount of oligomers formed over the time course of the aggregation process (FIG. 5a,b). Indeed, the formation of oligomers follows a parabolic evolution in that the number of oligomers formed during the aggregation of Aβ42 alone start to decrease at the point where the number in the presence of bexarotene started to increase.

To verify these predictions, we measured the cytotoxicity in human neuroblastoma cells (SH-SY5Y) resulting from the aggregation of 0.5 μM Aβ42 in the absence and presence of a 20-fold excess (i.e. 10 μM) of bexarotene by evaluating the levels of caspase-3, an early marker of apoptosis (see Methods). Indeed, caspase-9 is an initiator enzyme that mediates apoptotic pathways after mitochondrial damage and activates effector caspases, such as caspase-3, by cleaving their inactive pro-forms and initiating the apoptotic cascade. Staurosporine, which is a broad-spectrum kinase inhibitor known to activate the apoptosis pathway, was used as a positive control (see Methods).

Aliquots of Aβ42 solutions were removed at different time points during the lag phase of the aggregation reaction in the absence and presence of bexarotene and incubated with SH-SY5Y neuroblastoma cells. In its monomeric form (prior to incubation, FIG. 5c), Aβ42 showed no detectable toxicity irrespective of the presence of bexarotene. In the absence of bexarotene, the species formed after incubation for 0.3 h (FIG. 5d) and 4 h (FIG. 5e) exhibited a level of toxicity 65±5% higher than that in the presence of bexarotene. For the samples incubated for 7 h however, the level of toxicity generated in the presence of bexarotene increased to a value similar to that observed in its absence whereas the toxicity of Aβ alone decreased. This further supports a bexarotene-induced delay of the formation of Aβ42 toxic species in cell (FIG. 5f).

Bexarotene Rescues Aβ42-Mediated Dysfunction in C. elegans Models

We further evaluated the effects of bexarotene on the formation of toxic Aβ42 species in a C. elegans model of Aβ42 mediated dysfunction, denoted GMC101 (termed Aβ-worm model) (46), and compared the resulting effects of the addition of bexarotene to those observed in a control-worm model, CL2122, which is free of Aβ42 (see Methods). In the GMC101 model, Aβ42 is expressed in body wall muscle cells where it forms aggregates and results in severe age-progressive paralysis (46). We exposed the worms to increasing concentrations of bexarotene ranging from 5 to 10 μM and measured the frequency of body bends, which is indicative of the state of the muscle cells, and also the quantity of Aβ42 aggregates within the body of the worms (FIG. 6) (see Methods). In the absence of bexarotene, the frequency of the body bends of the Aβ-worm model decreased significantly after just 2 days compared to the situation in the control worm model where a similar decrease in the motility was observed only after 9 days (FIG. 6b). In agreement with such a difference, the levels of aggregates monitored using the fluorescence intensity of the amyloid specific dye NIAD-4 (47) differ dramatically between the two models, with essentially no aggregates being detected at the same day of the worms adulthood in the Aβ-worm model in the presence of bexarotene (FIG. 6c,d).

We then explored the effect of increasing concentrations of bexarotene added at the larval stages of the C. elegans life cycle (FIG. 6a), and observed a concentration-dependent maintenance of the motility of the Aβ-worm model. Indeed, the motility of the Aβ-worms was maintained completely upon addition of 10 μM bexarotene in two bursts at the L1 and L4 larval stages, i.e. reached the level observed in the control-worms (FIG. 4a,b). In addition, imaging studies (see Methods) showed that the addition of 10 μM bexarotene to the Aβ-worms suppressed the formation of Aβ42 fibrils for 9 days of adulthood (FIG. 6,d). The level of Aβ42 expression in the Aβ-worms in the absence and in the presence of bexarotene was found to be closely similar (FIG. 6e). This result indicates that maintaining the level of motility in the Aβ-worms could be achieved by preventing the aggregation of Aβ42 by bexarotene. In accord with this conclusion, the addition of bexarotene did not show any effects in a control-worm model. The normal motility observed for the Aβ-worms in the presence of bexarotene could be consistent with two distinct scenarios. One possibility could be a strong delay in primary nucleation, which would delay substantially the aggregation of Aβ42 and hence maintain the motility of the Aβ-worm model to values similar to that of the control-worms. Alternatively, these results could arise from a combination of effects on primary and secondary nucleation. This latter possibility is particularly relevant because although bexarotene preferentially inhibits primary nucleation, when in excess could also affect secondary nucleation. Indeed, our experiments under 5% seeds show that bexarotene is capable of acting also on surface-catalyzed secondary nucleation (FIG. 4f-h). Furthermore, we also observed that adding bexarotene only at day 2 did not show any detectable effect on the motility of the Aβ-worms, suggesting that the finding from the in vitro studies that bexarotene specifically affect nucleation events in Aβ42 aggregation is also the case in vivo.

Discussion

We have described a drug discovery strategy that aims at targeting Aβ42 aggregation with small molecules. This strategy involves the identification of compounds from an Aβ-specific fragment-based library and the subsequent application of chemical kinetics for gaining a fundamental understanding of the molecular mechanism of inhibition (FIG. 1). We have found that while tramiprosate has no effect on Aβ42 aggregation, bexarotene interferes selectively with the earliest stage of Aβ42 aggregation by reducing the rate of primary nucleation. We have also observed that this effect inhibits significantly the rate of the overall aggregation reaction not only in vitro by also in cells and in vivo, as bexarotene was found to suppress the formation of toxic species both in cells and in C. elegans. Furthermore, we have shown that a sufficient concentration of bexarotene given at the earliest stages of the C. elegans life cycle can maintain the motility of the worms expressing Aβ42 at a level comparable to those in which Aβ42 is not expressed, thus further supporting the preventive effect of this molecule (48-50).

We anticipate that the strategy that we have described in this paper will enable the identification of further compounds capable of inhibiting Aβ42 aggregation and the definition of the specific microscopic steps affected by each compound (i.e primary or secondary nucleation or elongation). These results should enable a range of compounds to be identified to control and modulate the onset of aggregation and the rate of its progression first in vitro and then in vivo. In addition, the results described in the present work indicate that bexarotene and other inhibitors of primary nucleation have the potential to be efficient means of reducing the level of aggregation, i.e. the probability that primary nuclei are formed, and proliferate, such that our natural protection mechanisms could remain effective to more advanced ages. Indeed, we draw an analogy between the strategy presented here and that of using statins, which reduce the level of cholesterol and so the risk of heart conditions, and suggest that such molecules could effectively act as heurostatins' In addition to the use of molecules such as bexarotene for preventive purposes, it is possible to speculate that targeting secondary nucleation, which is largely responsible for the production of toxic species (30), would form the basis to develop treatments to reduce the rate of progression of AD.

Conclusions

We have described in this study the development and application of a comprehensive strategy for the identification of potent anti-AD drugs. This strategy is based on understanding the molecular details of the inhibition processes, creating opportunities to identify effective therapeutic agents in a rational manner that could eventually lead to successful drugs to combat AD. Finally, given the general of the phenomenon of protein aggregation, the present strategy offers a framework for the rational design and evaluation of novel therapeutics to target other forms of neurodegenerative disorders.

Materials and Methods of Example I

Preparation of Aβ Peptides

The recombinant Aβ (M1-42) peptide (MDAEFRHDSGY EVHHQKLVFF AEDVGSNKGA IIGLMVGGVV IA (SEQ ID NO: 1)), here called Aβ42, was expressed in the *E. coli* BL21 Gold (DE3) strain (Stratagene, CA, U.S.A.) and purified as described previously with slight modifications (51). Briefly, the purification procedure involved sonication of *E. coli* cells, dissolution of inclusion bodies in 8 M urea, and ion exchange in batch mode on diethylaminoethyl cellulose resin and lyophylization. The lyophilized fractions were further purified using Superdex 75 HR 26/60 column (GE Healthcare, Buckinghamshire, U.K.) and eluates were analyzed using SDS-PAGE for the presence of the desired protein product. The fractions containing the recombinant protein were combined, frozen using liquid nitrogen, and lyophilized again.

Isotopically labeled $^{15}$N-Aβ42 was prepared by growing transformed *E. coli* BL21 Gold (DE3) strain (Stratagene, CA, U.S.A.) in 1 L flasks at 37° C. with 500 mL minimal M9 batch medium. Briefly, a 20 mL preculture grown overnight to saturation in LB medium containing 100 μg/L ampicilin was diluted 1/25 in 2YT medium supplemented with 100 μg/L ampicilin and grown at 37° C. When the OD at 600 nm reached 0.5, the cells were harvested, washed in minimal medium, and inoculated in ¼ of the initial culture volume of minimal M9 medium containing 100 μg/L ampicilin and supplemented with $^{15}$NH$_4$Cl (2 g/L) (Cambridge Isotopes Laboratories). Cells were grown at 37° C. for 2 hours before induction. IPTG was then added to a final concentration of 1 mM, and cells were grown at 37° C. overnight. Purification of $^{15}$N-Aβ42 was performed as described above. Chemicals, including bexarotene and tramiprosate, were obtained from Sigma-Aldrich and were of the highest purity available.

Preparation of Samples for Kinetic Experiments

Solutions of monomeric peptides were prepared by dissolving the lyophilized Aβ42 peptide in 6 M GuHCl. Monomeric forms were purified from potential oligomeric species and salt using a Superdex 75 10/300 GL column (GE Healthcare) at a flowrate of 0.5 mL/min, and were eluted in 20 mM sodium phosphate buffer, pH 8 supplemented with 200 μM EDTA and 0.02% NaN$_3$. The center of the peak was collected and the peptide concentration was determined from the absorbance of the integrated peak area using ε280=1400 l mol$^{-1}$ cm$^{-1}$. The obtained monomer was diluted with buffer to the desired concentration and supplemented with 20 μM Thioflavin T (ThT) from a 1 mM stock. All samples were prepared in low binding eppendorf tubes on ice using careful pipetting to avoid introduction of air bubbles. Each sample was then pipetted into multiple wells of a 96-well half-area, low-binding, clear bottom and PEG coating plate (Corning 3881), 80 μL per well.

For the seeded experiments, preformed fibrils were prepared just prior to the experiment. Kinetic experiments were set up just as above for a 4-M Aβ42 samples in 20 mM sodium phosphate buffer, pH 8 with 200 μM EDTA, 0.02% NaN$_3$ and 20 μM ThT. The ThT fluorescence was monitored for 3 hours to verify the formation of fibrils.

Samples were then collected from the wells into low-binding tubes and sonicated for 2 min in a sonicator bath at room temperature. Under the considered conditions (i.e. 4 μM Aβ42), the monomer concentration is negligible at equilibrium (31). The final concentration of fibrils, in monomer equivalents, was considered equal to the initial concentration of monomer. Fibrils were then added to freshly prepared monomer in order to reach either 5% or 10% fibrils final concentration.

In all cases, bexarotene was first solubilized in 100% DMSO to a concentration of 5 mM, and then diluted in the peptide solution to reach a final DMSO concentration of maximum 1%. We verified that the addition of 1% DMSO in the reaction mixture has no effect on Aβ42 aggregation.

Kinetic Assays

Assays were initiated by placing the 96-well plate at 37° C. under quiescent conditions in a plate reader (Fluostar Omega, Fluostar Optima or Fluostar Galaxy, BMGLabtech, Offenburg, Germany). The ThT fluorescence was measured through the bottom of the plate with a 440 nm excitation filter and a 480 nm emission filter. The ThT fluorescence was followed for three repeats of each sample.

Theoretical Analysis

The time evolution of the total fibril mass concentration, M(t), is described by the following integrated rate law (30, 32)

$$\frac{M(t)}{M(\infty)} = 1 - \alpha \left( \frac{B_+ + C_+}{B_+ + C_+ e^{kt}} \frac{B_- + C_+ e^{kt}}{B_- + C_+} \right)^{\frac{k_\infty^2}{kk_\infty}} e^{-k_\infty t} \quad (1)$$

where the kinetic parameters $B_\pm$, $C_\pm$, $\kappa$, $\kappa_\infty$ and $\tilde{\kappa}_\infty$ are functions of the two $\tilde{\kappa}_\infty$ combinations of the microscopic rate constants $k_+k_2$ and $k_nk_2$, where $k_n$, $k_+$ and $k_2$ are the primary nucleation, elongation and secondary nucleation rate constants, respectively.

Bexarotene can interfere with the aggregation process by inhibiting one or more of the individual microscopic reactions. We can identify the microscopic events that are inhibited by the chemical compound by applying the above equation to describe the macroscopic aggregation profiles shown in FIG. 4, and comparing the set of microscopic rate constants $k_+k_2$ and $k_nk_2$ required to describe the time evolution of the fibril formation in the absence and presence of bexarotene. As shown in FIG. 4, in unseeded aggregation reactions the presence of the chemical compound perturbs mainly the primary nucleation rate.

The numerical simulations reported in FIG. 5a, b show the reaction profiles in the presence and absence of beratoxene simulated according to Eq. 1

The time evolution of the nucleation rate, r(t), has been simulated according to the equation $$r(t) = k_2 M(t) m(t)^2 + k_n m(t)^2$$

Model simulations in FIG. 4f were performed by fixing the $K_+$ and $K_2$ parameters for a 2 μM Aβ42 solution seeded with 5% of pre-formed seed fibrils. The $K_n$ parameter was then decreased to very negligible values (~0). This showed insignificant perturbation to the reaction profile when the primary nucleation process does not occur.

AFM Imaging

Aβ42 samples were removed from the aggregation reaction and were directly deposited onto freshly cleaved mica surfaces and allowed to dry for 30 minutes. Samples were then washed with Milli-Q water and then dried with nitrogen. AFM images were acquired using a VEECO Dimension 3100 atomic force microscope (Brucker) and JPK Nanowizard software (Cambridge, UK). The instrument was operated in tapping mode in air using n-type silicon cantilevers with resonant frequencies between 65 and 130 kHz.

Dot Blot Assay

Blotting was performed using either Aβ42 fibril-specific antibody (OC, Millipore) or Aβ42 sequence-specific antibody (W0-2, Millipore). During the time course of the aggregation of a 2 μM Aβ42 in the absence and in the presence of 4-fold excess of bexarotene (FIG. 3), 4 μL and 2 μL Aβ42 aliquots were removed from the mixture at different time points for blotting with either OC or W0-2, respectively. Aβ42 aliquots were spotted onto a nitrocellulose membrane (0.2 μm, Whatman) and then the membranes were dried and then blocked with Blocking One (Nacalai tesque) before immuno-detection. OC and W0-2 were used according to the manufacturers instructions. Alexa Fluor® 488-conjugated secondary antibodies (Life technologies) were subsequently added and fluorescence detection was performed using Typhoon Trio Imager (GE Healthcare). DMSO-solubilized bexarotene was added to Aβ42 with a final concentration of 1% DMSO. For the calibration curve (FIG. 3d), a series of dilutions between 4 μM and 0.1 μM were performed on freshly prepared Aβ42 fibrils and 4 μL aliquots were deposited onto the same nitrocellulose membrane (0.2 μm, Whatman) as the one used for OC fibril-specific antibody. Note that oligomers-specific A11 antibody was also used to detect the evolution of the formation of Aβ42 oligomers in the absence and in the presence of bexarotene. However, under these conditions we could not detect oligomers due to their very low concentration during Aβ42 aggregation even when depositing on the membrane volumes as high as 20 μL.

NMR Experiments

For NMR analyses, $^{15}$N-Aβ42 was purified as described above except that the buffer of the gel filtration was 50 mM ammonium acetate, pH 8.5. Lyophilized powder of $^{15}$N-Aβ42 was dissolved at an approximately concentration of 1 mM in 0.2% (v/v) ammonium solution and then collected and stored in aliquots at −80° C. until use. NMR samples were prepared by dissolving the lyophilized powder in 20 mM potassium phosphate buffer (pH 7.4) at a concentration of 25 μM containing 10% (v/v) $^2$H$_2$O in the presence and absence of 5-fold excess of bexarotene in 2.5% DMSO. The pH of the mixture was checked for possible pH variations that could occur from the addition of bexarotene and was found to be unchanged. NMR spectral measurements were made on a Bruker AVANCE-500 spectrometer equipped with a cryogenic probe. The probe temperature was set to 278K. $^1$H-$^{15}$N heteronuclear single-quantum correlation (HSQC) spectra were recorded at a $^1$H observation frequency of 500 MHz with 128 ($t_1$)×1,024 ($t_2$) complex points and 32 scans per $t_1$ increment. The spectral width was 1,216 Hz for the $^{15}$N dimension and 6,010 Hz for the $^1$H dimension.

Chemical shift perturbation (CSP) and intensity changes were monitored using $^1$H-$^{15}$N HSQC spectra at increasing molar ratios of bexarotene to monomeric Aβ42. A reference sample of DMSO without compound was also titrated into Aβ42 samples. CSP and intensity ratio due to the addition of DMSO was subtracted from those observed during titrations with compound. CSP was calculated as $\Delta\delta=((\Delta\delta_N/5)^2+(\Delta\delta_H)^2)^{1/2}$. NMR spectra were processed by TopSpin 2.1 (Bruker).

Resonance assignment and intensity calculations were performed by the program Sparky (https://www.cgl.ucsf.edu/home/sparky/). The sample preparation protocol and the low NMR probe temperature (5° C.) were chosen to ensure that the Aβ42 peptide remained monomeric during the entire data acquisition. The HSQC spectra are typical of intrinsically disordered peptides with a very low dispersion of resonant frequencies.

Caspase-3 Cytotoxicity Assay

Aβ42 oligomers are known to be toxic to cells leading to apoptosis and to cellular death. Cytotoxicity assays were performed by measuring the activity of caspase-3, an earlier marker of apoptosis, in a neuroblastoma cell line when incubated with Aβ42 either in the presence and in the absence of bexarotene (52). SH-SY5Y human neuroblastoma cells were cultured under standard conditions, at 37° C. in a humidified incubator with 5% $CO_2$. Cells were seeded at a density of 25,000 per well in a white-walled, clear-bottomed 96-well plate and cultured for 24 h in MEM/F12 (1:1)/10% Fetal Bovine Serum (FBS) (Gibco). The culture medium was then replaced with pre-warmed phenol red free DMEM without FBS into which the peptide samples or NaPO4 buffer were diluted 1:1. Aβ samples at roughly 0.5 μM, either alone or in the presence of 20-fold excess of bexarotene in 1% DMSO final concentration, were removed from an ongoing aggregation reaction at different time points (0, 0.3, 4 and 7 hours) and were followed in parallel by means of ThT fluorescence. The aggregation reaction was set up as above except for the buffer from which $NaN_3$ was removed due to its toxicity. Note that at 10 μM, DMSO-solubilized bexarotene did not show any toxicity and thus was comparable to the control values. All the specified time points correspond to Aβ42 in the lag phase in order to monitor inhibition at the early stage of the aggregation. We used one separate plate for each time point with 25 replicates of Aβ either alone or in the presence of bexarotene. The cells were cultured in the presence of the peptides, buffer and media for further 24 h before the cytotoxic effect was measured.

Cell medium diluted with the same buffer that was used in these experiments was included in some wells in order to evaluate the intrinsic fluorescence of the media and bexarotene.

As a negative control, we added to the cells the cell media diluted with the buffer that was used to prepare bexarotene (phosphate buffer with 1% DMSO). For the positive control, staurosporine (1 μM) was added to the cells for 2 hours. Caspase-3/7 activity was measured using the Apo-ONE Homogeneous Caspase-3/7 assay (Promega). The fluorogenic caspase-3/7 substrate, rhodamine 110 bis-(N-CBZ-L-aspartyl-L-glutamyl-L-valyl-aspartic acid amide) was diluted 1:100 in the lysis buffer provided and added to the cell medium at a 1:1 ratio. The fluorescence was measured at excitation 480 nm/emission 520 nm in an Optima FluoStar plate reader. In each of the used plates, the toxicity was assessed according to a negative and a positive control.

For comparative purposes between different plates, we normalized the fluorescence values using a parabolic equation ($y=ax^b$), which corresponds to the evolution of the oligomers as a function of time. Negative and positive controls were set to 1 and 10, respectively. According to these calculations, the toxicity of Aβ42 in the absence and in the presence of bexarotene possesses normalized values between 1 and 10 and hence could be compared between different plates. Statistical analyses were performed using GraphPad prism 6.0. Results are expressed as mean±SEM.

Statistical analysis were performed by Student T test or One way Analysis of Variance followed by Tuckey's post hoc test.

*C. elegans* Experiments

Standard conditions were used for *Caenorhabditis elegans* propagation at 20° C. (53). Briefly, animals were synchronized by hypochlorite bleaching, hatched overnight in M9 buffer, and subsequently cultured on nematode growth medium (NGM, USP agar) plates seeded with the *E. coli* strain OP50. Saturated cultures of OP50 were grown by inoculating 50 mL of LB medium with OP50 and incubating the culture for 16 h at 37° C. NGM plates were seeded with bacteria by adding 350 µl of saturated OP50 to each plate and leaving the plates at room temperature for 2-3 days. On day 3 after synchronization, animals were placed on NGM plates containing 5-fluoro-2'deoxy-uridine (FUDR) (75 mM, unless stated otherwise) to inhibit growth of offspring.

The following strains were used: dvls100[unc-54p::A-beta-1-42::unc-54 3'-UTR+mtl-2p::GFP] (GMC101). mtl-2p::GFP produces constitutive expression of GFP in intestinal cells. unc-54p::A-beta-1-42 expresses full-length human Aβ42 peptide in bodywall muscle cells that aggregates in vivo. Shifting L4 or young adult animals from 20 C° to 25 C° causes paralysis dvls15[pPD30.38 (unc-54 vector)+ mtl-2::GFP (pCL26)] (CL2122), control strain for GMC101 (57). Phenotype apparently WT. *C. elegans* var Bristol (N2). Generation time is about 3 days. Brood size is about 350. Isolated from mushroom compost near Bristol, England. Bexarotene stock (5 mM in 100% DMSO) was used at appropriate concentration to seed 9 cm NGM plates. Plates were placed in a laminar flow hood at room temperature (22° C.) for 1 h to dry. *C. elegans* cultures were transferred onto media with compound as L1 larvae for 64-72 h at 20° C. Cultures were then transferred to freshly seeded 9 cm plates as young adults, and incubated at 23° C. or 25° C. for the whole experiment. Experiments were carried out at different bexarotene concentrations ranging from 5 to 10 µM in 1% DMSO. As controls, plates seeded only with 1% DMSO were used

*C. elegans* Motilty Assay

All populations were cultured at 20° C. and developmentally synchronized from a 4 h egg-lay. At 64-72 h post egg-lay (time zero) individuals were shifted to 23° C. or 25° C., and body movement assessed over time as indicated. At different ages, animals were washed out of the plates with M9 and spread over an un-seeded 6 cm plate, after which their movements were recorded at 30 fps using a home-made microscopic setup, at 0.75× magnification, for 30 s or 1 min. 200 animals were counted per experiment unless stated otherwise. All experiments were carried out in triplicate and the data from one representative experiment are shown. Statistical analyses were performed using the Graphpad Prism software (GraphPad Software, San Diego, Calif., USA).

Videos were elaborated using ImageJ (National Institutes of Health, Bethesda, Md., USA), and body bends were quantified using the wrMTrck plug-in (http://www.phage.dk/plugins/wrmtrck.html), developed by Jesper Søndergaard Pedersen.

Staining and Microscopy in Living *C. elegans*

Live transgenic animals were incubated with NIAD-4 over a range of concentrations and times, and it was empirically determined that incubation of living animals with 1 µM NIAD-4 (0.1% DMSO in M9 buffer) for four hours at room temperature gave robust and reproducible staining. After staining, animals were Let recover on NGM plates for about 24 hrs to allow destaining via normal metabolism. Stained animals were mounted on 2% agarose pads containing 40 mM $NaN_3$ as anaesthetic on glass microscope slides for imaging. Images were captured with a Zeiss Axio Observer.D1 fluorescence microscope (Carl Zeiss Microscopy GmbH, Jena, Germany) with a 20× objective and a 49004 ET-CY3/TRITC filter (Chroma Technology Corp, Bellows Falls, Vt., USA). Fluorescence intensity was calculated using ImageJ software (National Institutes of Health, Bethesda, Md., USA), and then normalized as the corrected total cell fluorescence (CTCF). Only the head region was considered, due to the high background signal in the guts. All experiments were carried out in triplicate and the data from one representative experiment are shown. Statistical significance was determined using t tests.

Western Blot Analysis

For comparison of the Aβ expression level in the absence and in the presence of bexarotene, ~3000 adults were collected in S-basal (10) in triplicate, then frozen in liquid-$N_2$. Samples were then extracted in RIPA buffer (50 mM Tris pH 8, 150 mMNaCl, 5 mM EDTA, 0.5% SDS, 0.5% SDO, 1% NP-40, 1 mM PMSF, Roche Complete inhibitors 1×) (Roche Holding AG, Basel, Switzerland), disrupted via sonication, and then centrifuged at 16,000 rpm for 10 min at 4° C. Pellets and supernatants were then separated. Pellets were solubilised using Urea/SDS buffer (8M Urea, 2% SDS, 50 mM Tris). Samples at the appropriate concentration were added to NuPAGE® LDS Sample Buffer (1×) and NuPAGE® Sample Reducing Agent (1×) (Life Technologies, Carlsbad, Calif., USA), and heated at 70° C. for 10 min. Material was resolved via NuPAGE® Novex® 4-12% Bis-Tris Protein Gels (Life Technologies Carlsbad, Calif., USA), then transferred to nitrocellulose membranes, using a iBlot® Dry Blotting System (Life Technologies, Carlsbad, Calif., USA), and blocked overnight at 4° C. in 5% Bovine serum albumin (BCA). Membranes were then probed at room temperature with MABN10 anti-Aβ Antibody, clone W0-2 (Millipore, Billerica, Mass., USA) diluted to 1:500. Blots were re-probed with anti-α-tubulin, clone B-5-1-2 (Sigma-Aldrich, St. Louis, Mo., USA) diluted to 1:5000, to standardize total protein loading. Alexa 488 conjugated secondary antibody was used for detection.

Example II

In the previous example, we identified an FDA-approved anti-cancer drug, bexarotene, which was found to delay substantially the aggregation of Aβ42 by preferentially inhibiting the primary nucleation step. This result could be achieved thanks to the application of a novel chemical kinetics approach in drug discovery, in which the effects of small molecules on the rates of specific microscopic steps in Aβ42 aggregation are analyzed quantitatively. Indeed, under quiescent conditions, bexarotene delayed the aggregation of Aβ42 in a concentration-dependent manner with this delay being consistent with a very selective effect on the primary nucleation step (FIG. 7, Top left). Interestingly, under mild seeding conditions, i.e. 5% of pre-formed fibril seeds, bexarotene decreased significantly the rates of secondary pathways in a concentration-dependent manner. Under these conditions, the primary nucleation step is completely by-passed whereas surface-catalyzed secondary nucleation and elongation still occur. However, the observed decrease was consistent with a specific decrease in the rates of surface-catalyzed secondary nucleation and not in the rates of elongation since under high seeding conditions, i.e. in the presence of 10% pre-formed fibril seeds where elongation is the dominant mechanism, no effect of bexarotene on the aggregation of Aβ42 could be observed.

Thus, bexarotene was found to be a potent molecule in inhibiting both, the primary and secondary nucleation steps, in Aβ42 aggregation, with this effect likely occurring by binding to primary and secondary nuclei. Indeed, no effect of bexarotene on Aβ42 monomeric species could be observed by NMR spectroscopy. Importantly, the in vitro effect of bexarotene on Aβ42 aggregation was found to be similar in cells as well as in *C. elegans* model of Aβ-mediated toxicity. Indeed, we have shown that the delay in Aβ42 fibril formation resulting from inhibiting the nucleation steps by bexarotene is associated with a delay in the formation of neurotoxic species in neuroblastoma cells and a complete suppression of Aβ42 deposition and its consequences in the Aβ-worms. These results suggested that preventing the nucleation of Aβ42 by compounds such as bexarotene could potentially reduce the risk of onset of Alzheimer's disease, and more generally that our kinetics-based drug discovery strategy provides a general framework for the rational identification of a range of candidate drugs directed against neurodegenerative disorders.

II—Identification of Small Molecules Against Aβ42 Aggregation Through a Quasi-Structure-Based Drug Discovery (QSBDD) Strategy In order to further identify small molecules against Aβ42 aggregation, we have developed a Quasi-Structure-Based Drug Discovery Strategy (QSBDD). The rationale behind this approach is that the primary and secondary nuclei, with which bexarotene interact, are unstable, poorly abundant and occur transiently during the aggregation pathway of Aβ42. Therefore, their dynamic and transient nature precludes their structural characterization using conventional biophysical approaches, which subsequently makes the application of structure-based drug discovery strategies very challenging. In order to overcome this limitation, we applied a novel strategy, termed QSBDD that is based on the assumption that primary and secondary nuclei share common structural features, which allow them to interact with bexarotene and that the same structural features are very likely shared with the structural pocket to which bexarotene initially binds to. Bexarotene is a retinoid X receptor (RXR) agonist approved by the FDA for the treatment of cutaneous T-cell lymphoma. Ligands that bind to RXR and to their partners, the retinoid A receptors (RAR), modulate the communication of the receptors with its intracellular environment, which entails essentially receptor-protein and receptor-DNA or receptor-chromatin interactions. Receptors are mediators of the information encoded in the chemical structure of their ligands, which consequently serves as a dual input-output information processor. RAR-RXR heterodimers (FIG. 7 Top, middle) are believed to mediate the physiological function of natural ligands and therefore are attractive targets for drug discovery. A major breakthrough of the past few years has been the recognition of the enormous variety of communication processes that can be collectively or separately addressed by simply modifying the ligand structure. In addition, the 3-D structure of both, retinoid A and X receptors, have been solved in the absence and presence of bexarotene (FIG. 7 Top, middle and right), and the mechanism of binding of the ligands to the RAR and RXR binding domains (LBD) are well understood and pharmaceutically exploited. Taking advantage from the available data on i) the atomic structures of the LBDs and ii) the chemistry of the available agonists and antagonists of RAR and RXR, we applied the QSBDD and we collected twelve available agonists and antagonists considering that the molecules should inhibit the aggregation of Aβ42 similarly to bexarotene. Indeed, five RAR agonists namely Tamibarotene, BMS753, Adapalene, CD 1530, TTNPB, Ch55, four RAR antagonists namely, BMS195614, LE135, MM11253, BMS493, two RXR agonists including bexarotene and SS11237, and one RXR antagonist namely UVI3003 have been tested in our ThT-based chemical kinetics assay. Thereafter, we have compared their effect on the different microscopic steps in Aβ42 aggregation to that of bexarotene (FIG. 7, bottom).

There is no previous data relating the structure of the RXR/RAR receptors to that of Aβ42. Indeed, in the rationale of the QBSDD, the small molecules bind to transient and instable structures of Aβ42, which are very difficult to characterize from a structural point of view. This was one of the main reasons that prompted the search for a novel technique to identify new inhibitors, such as the QBSDD that is described here.

Accordingly, this approach can be extended to identify inhibitors that act on other protein systems that are responsible for different misfolding diseases.

III—RXR and RAR Ligands Delay the Aggregation of Aβ42 to Different Extent

In order to investigate the effects of the selected RXR and RAR ligands on the individual microscopic steps underlying the aggregation process of Aβ42, we monitored the fibril formation of Aβ42 in vitro in the absence and the presence of the small molecules. Due to the hydrophobic nature of the small molecules, these latter were prepared in 1% DMSO final concentration. Accordingly, in order to exclude any effect of 1% DMSO on the aggregation of Aβ42, the experiments were followed in parallel in the absence and the presence of DMSO using dot-blot and ThT-based kinetics. No effect of DMSO on Aβ42 was observed. We have probed the quantities of Aβ42 at twelve different time points during the aggregation reaction using fibril-sensitive OC primary antibodies and the intensities of the dots were subsequently quantified. Fibril-specific OC antibodies, which recognize only fibrillar species, showed a similar aggregation profile of Aβ42 in the absence and the presence of 1% DMSO. These results were further confirmed using ThT-based kinetics that showed identical sigmoidal curves in the absence and the presence of 1% DMSO. Interestingly, the half-times of the aggregation reactions were found to be similar irrespective of the presence of either ThT or 1% DMSO, thus excluding any effect of ThT and 1% DMSO on the aggregation kinetics of Aβ42.

Upon the addition of 3-fold excess of the twelve small molecules to a 2 µM solution of Aβ42, we observed a differential delay in Aβ42 aggregation, with the delay being significant for all the small molecules except for BMS753 (FIG. 8a). The observed delay was in most of the cases stronger than that of bexarotene, and more interestingly, five out of the twelve molecules, namely MM11253, BMS493, Adapalene, CD1530 and LE135, inhibited completely the aggregation of Aβ42 within 10-15 hours (FIG. 8a).

In order to monitor this effect further and to exclude any possible interference of the small molecules with the ThT binding to Aβ42 fibrils and consequently to the resulting fluorescence, we have probed the quantities of Aβ42 converted into fibrils at twelve different time points during the aggregation reaction, similarly to above, using fibril-sensitive OC primary antibodies in the presence of either 1% DMSO or the small molecules. The delay that was induced by the small molecules in the dot-blot assay was found to be identical to that observed in the ThT-based kinetics assay, thus further supporting the crucial role that the chemical kinetics assay play in assessing the effect of small molecules in inhibiting protein aggregation. In agreement, the same five molecules inhibited the aggregation reaction completely within 10-15 hours, similarly to the effect observed in the ThT-based assay. For a better understanding of the mechanism of inhibition of Aβ42 aggregation by these latter molecules, we performed the same assays, dot-blot and ThT-based kinetics, under sub-stoichiometric quantities of the small molecules (FIG. 8b). Interestingly, these molecules were found to be extremely effective as the aggregation of Aβ42 was substantially delayed in the presence of sub-stoichoimetric amounts of the small molecules.

IV—Ranking of RAR and RXR Ligands According to their Efficacy in Inhibiting the Aggregation of Aβ42

The RXR and RAR ligands were found to delay Aβ42 aggregation to different extent using two non-related quantitative approaches, i.e. ThT-based and label-free dot-blot kinetic assays. Accordingly, the molecules could be classified according to their efficacy in inhibiting the aggregation reaction. The intensities of the dots from the dot-blot in were quantified and the corresponding values were normalized against those of Aβ42 in the presence of 1% DMSO. Consequently, the values of two early time points in the aggregation reaction were plotted against the half-times that were derived from the ThT-based kinetics (FIG. 8c, d). Interestingly, a linear correlation could be observed between the dot-blot intensities and the values of the half-times, thus further supporting the consistency between our assays. This correlation allowed to classify the RAR and RXR ligands into sets of molecules according to the extent of the delay they induce in the aggregation of Aβ42.

Three sets of molecules could be distinguished (FIG. 8c, d): Set A consists of one molecule, BMS753, that did not show any effect on the aggregation (FIG. 8b), Set B consists of all the molecules that showed an effect that is similar or stronger than that of bexarotene at 3-fold excess (FIG. 8b), and Set C consists of the small molecules that completely inhibited the aggregation at 3-fold excess and their effect was further analyzed at sub-stoichiometric quantities (FIG. 8d). In addition, in each of the Set B and Set C molecules, the compounds could be ranked amongst each others, with UVI3003 being the most effective molecule within Set B as it delays substantially the aggregation compared to bexarotene, whereas MM11253 and Adapalene being the most effective molecules within Set C as the aggregation of a 2 μM sample of Aβ42 was delayed by at least 3 fold at 0.5-fold excess. In addition, RAR and RXR ligands inhibited the aggregation reaction of Aβ42 in a concentration-dependent manner with Set C molecules being able to inhibit the aggregation significantly at fold excesses as low as 0.2 (FIG. 8e, f). Note that BMS753, i.e. Set A, did not show any effect on the aggregation kinetics of Aβ42 even at fold-excesses as high as 5.

Strikingly, no correlation could be observed between the initial function of the RAR and RXR agonists and antagonists in enhancing or inhibiting the activity of their corresponding receptors and their potency in inhibiting the aggregation of Aβ42. For instance, the Set B molecules consists of agonists and antagonists of both, RAR and RXR and Set C molecules consist of agonists and antagonists of RAR.

V—Comparative Analysis of the Effect of the RAR and RXR Ligands on Specific Microscopic Steps in Aβ42 Aggregation Using Chemical Kinetics We then carried out a quantitative analysis of the effects of Sets B and C molecules by matching the aggregation profiles based on the rate laws derived from a master equation that relates the macroscopic time evolution of the quantity of fibrils to the rate constants of the different microscopic events. In this approach, the aggregation profiles in the presence of the inhibitor are described by introducing into the rate laws suitable perturbations to each of the microscopic rate constants evaluated in the absence of the inhibitor. The modifications of the rate constants required to describe the aggregation profiles in the presence of different concentrations of inhibitor are then indicative of the specific process affected by the presence of the compound.

The evolution of the rate constants of primary ($k_n k_+$) versus secondary ($k_2 k_+$) pathways is therefore monitored in the presence of increasing concentrations of the small molecules.

a—Effect of Set B and Set C Molecules on the Aggregation of Aβ42 Under Quiescent Conditions The aggregation profiles of a 2 μM solution of Aβ42 in the presence of concentrations of Set B and Set C molecules in the range of 2-10 μM show that the experimental data are extremely well described when the primary pathways, $k_n k_+$, is specifically decreased at fold-excesses less than 3 for Set B and less than 0.5-1 for Set C. By contrast, at higher fold-excesses of small molecules, the experimental data are consistent with a decrease in the rate constants of both, primary, i.e. $k_n k_+$, and secondary pathways, i.e. $k_2 k_+$. These experiments revealed that set B and Set C molecules could affect both pathways in the aggregation reaction of Aβ42, with the effect being significant at high concentrations of the small molecules (FIG. 9-10, 11a-g, 12 a-e). Interestingly, this effect could be predicted already from the shape of the kinetic curves in FIG. 9-10 where the small molecules affect the observed kinetic macroscopic profiles in a characteristic way, i.e. the curves show a different slope at higher fold excesses with respect to that of Aβ42 in the absence of small molecules.

b—Effect of Set B and Set C Molecules on Aβ42 Elongation Rates

In order to unveil the effect of the small molecules on individual microscopic steps of secondary pathways, i.e. surface-catalyzed secondary nucleation versus elongation, we carried out an additional series of measurements of the aggregation kinetics of Aβ42 in the presence of small molecules in the presence of 10% preformed fibril seeds to the reaction mixture, where the primary and secondary nucleation steps are bypassed. In such a situation, the conversion of the soluble peptide into mature fibrils is greatly accelerated by elongation reactions that are promoted by the seeds In the presence of 10% fibril seeds, no effect is observed from the Set B molecules on the aggregation kinetics of a 2 μM solution of Aβ42 even at 5-fold excesses (FIG. 11h), while the corresponding aggregation process under unseeded conditions was delayed by at least 3 fold (FIG. 8e). This was confirmed quantitatively by deriving the growth rates of Aβ42 from the kinetic curves in the absence and the presence of Set B molecules (FIG. 11i). Interestingly however, Set C molecules decreased the growth rates by 25% at 5-fold excess (FIG. 12 f,g), thus explaining the increased potency of Set C molecules with respect to that of Set B molecules. Note that at 0.5-fold excess, no effect was observed from Set C molecules on the elongation of Aβ42 fibrils, thus indicating that inhibiting the elongation step requires higher concentrations of small molecules than the nucleation steps (FIG. 12h,i).

c—Effect of Sets B and C Molecules on the Surface-Catalyzed Secondary Nucleation Rates of Aβ42 Aggregation In order to obtain a complete comparative assessment on the effect of Set B and Set C molecules on the aggregation of Aβ42, we also measured the aggregation kinetics of a 2 μM sample of Aβ42 in the presence of different seed conditions, i.e. 1% to 5%, for the aim of unveiling the effect of the small molecules on the surface-catalyzed secondary nucleation step (FIG. 13-14). Indeed, primary nucleation is completely by-passed as early as . . . % of pre-formed seeds has been introduced in the solution. On the other hand, both surface-catalyzed secondary nucleation and elongation mainly contribute to the overall kinetics with the contribution of elongation becoming more significant with increasing seed concentrations. Interestingly, experiments performed in the presence of mild seed concentrations, i.e. 1-5% seeds, show a concentration-dependent inhibition of secondary pathways (i.e. $k_2k_+$) of Aβ42 aggregation in the presence of both sets of molecules, B and C. In the case of set B molecules, the decrease at 0.5- and 5-fold excesses could be attributed only to a decrease in the rate of surface-catalyzed secondary nucleation, i.e. $k_2$, since no effect could be observed on the elongation of the fibrils, i.e. $k_+$, at fold excesses as high as 5 (FIG. 11$h,i$). The rates could be derived from the kinetic curves and were found to be decreased by at least 50% and 75% in the presence of 0.5- and 5-fold excess of the Set B molecules, respectively. These findings show that while the elongation of fibrils is essentially unaffected by Set B molecules, these compounds have a large and highly selective effect on the nucleation steps in Aβ42 aggregation, with the effect being pronounced towards secondary nucleation as low concentrations of the molecules were enough to decrease the rates significantly. This observation further supports the key role of surface-catalyzed secondary nucleation as the dominant mechanism in promoting the catalytic cycle of Aβ42 aggregation. On the other hand, in the case of Set C molecules, the effect on the rates of surface-catalyzed secondary nucleation could be quantified under the conditions where elongation is not affected, i.e. in the presence of 0.5-fold excess of the small molecules. Set C molecules were found to be significantly more effective in inhibiting the surface-catalyzed secondary nucleation process in Aβ42 aggregation than Set B, with the decrease being as high as 75% at 0.5-fold excess, thus further confirming the higher potency of Set C molecules with respect to that of Set B molecules.

In order to probe further the effect of Sets B and C molecules on the surface-catalyzed secondary nucleation step in Aβ42 aggregation, we performed additional experiments where we monitored the effect of the small molecules under 10% seeds in the presence of a molecular chaperone, clusterin. The rationale behind these experiments is that under 10% seeds, the existing fibrils will elongate by addition of the monomers at the fibrils ends. However, in the presence of the molecular chaperone, clusterin, which is known to inhibit specifically the elongation step of Aβ42 fibrils, the fibril ends are blocked and hence the surface-catalyzed secondary nucleation is expected to be restored to a level that could be detected by assessing the effect of the small molecules on the rates of surface-catalyzed secondary nucleation. Indeed, 10% of clusterin with respect to Aβ42 were found to decrease the rates of fibril growth of Aβ42 by roughly 40%, which indicates that nearly half of the fibril ends are blocked by clusterin and hence 10% of pre-formed fibril seeds are expected to affect the aggregation kinetics of Aβ42 similarly to a solution containing 5% seeds. The effects of Set B and Set C molecules on the aggregation of Aβ42 were thereafter monitored in the presence of 10% of pre-formed fibril seeds and 10% of clusterin. Interestingly, these experiments showed that Set B molecules delay the aggregation in a concentration-dependent manner while no effect was observed in the corresponding reaction without clusterin (FIG. 15$a$-$c$). The observed delay is therefore consistent with a decrease in the rates of surface-catalyzed secondary nucleation. These results further support the mechanistic interchangeability between surface-catalyzed secondary nucleation and elongation pathways where inhibiting one step redirects the aggregation reaction towards the other one. The decrease in the rates that was induced by Set B molecules could be quantified and was compared to that in the presence of 5% pre-formed fibril seeds (FIG. 15$d$). Interestingly, at 0.5-fold excess of Set B molecules, the effect on the aggregation of Aβ42 under 10% seeds and in the presence of clusterin is very comparable to that observed under 5% seeds. Unexpectedly however, at 5-fold excess of the molecules, the decrease in the rates of surface-catalyzed secondary nucleation is much more pronounced when both clusterin and the small molecules contribute to the effect. This finding is of paramount importance given that under in vivo conditions, where chaperones are present, the small molecules are expected to affect the aggregation more strongly. The higher effect is likely to be the result of a higher affinity of the small molecules towards the resulting complexes between the aggregated Aβ42 species and the molecular chaperone. The same dose-dependent effect on the aggregation of Aβ42 under 10% seeds and in the presence of clusterin was also observed in the presence of Set C molecules (FIG. 16$a$-$c$). In addition, at 0.5-fold excess of Set C molecules, where the elongation step is not affected, the decrease in the rates of surface-catalyzed secondary nucleation was found, similarly to set B molecules, to be higher in the presence of clusterin as compared to that observed in the presence of 5% seeds (FIG. 16$d$). Interestingly, the decrease in the rates of surface-catalyzed secondary nucleation that was observed in the presence of Set C molecules at 0.5-fold excess is comparable to that observed for the Set B molecules at 5-fold excess, thus further confirming the higher potency of Set C molecules, i.e. at least 10 times higher, than that of Set B molecules on the surface-catalyzed secondary nucleation step of Aβ42 aggregation.

d—Identification of the Target Species with which the Small Molecules Likely Interact The observation that Set B and Set C molecules affect different microscopic steps in the aggregation of Aβ42 could in principle result from the interaction of the small molecules with different Aβ42 species along the aggregation pathway (FIG. 17$a$).

Indeed, inhibiting both primary and surface-catalyzed secondary nucleation could result from binding of the small molecules to primary and secondary nuclei and/or fibril surface. On the other hand, inhibiting the three microscopic steps by Set C molecules correspond to the situation where the small molecules bind to monomeric species of Aβ42 as the monomers are involved in the three microscopic steps. Interestingly, NMR spectroscopic measurements showed no significant perturbations of the chemical shifts and the intensity in the HSQC spectra of a 25 μM sample of $^{15}$N-labeled monomeric Aβ42 before and after the addition of all Set C molecules and of UVI3003, the most effective molecule of Set B (FIG. 17$b$, $c$). This indicates that Set C molecules likely bind to primary and secondary nuclei and/or fibril surface and fibril ends (FIG. 17$a$).

These findings suggest all together that primary and secondary nuclei of Aβ42 are likely to possess similar structural features since they are able to interact with both, Set B and Set C molecules, and hence the same residues of Aβ42 may be involved in both, primary and secondary nucleation events. Conversely, inhibiting the elongation step in Aβ42 aggregation is likely to require additional chemical features that are present only in Set C molecules. Indeed, UVI3003, the most effective molecule in Set B, showed effects on the surface-catalyzed secondary nucleation step of Aβ42 as significant as those of the Set C molecules, i.e. a decrease in $k_2$ by 75% at 0.5-fold excess, while no effect could be observed on the elongation step even at 5-fold excess. Furthermore, these experiments suggest that a selective preferential sequential binding of the small molecules is likely to occur and hence they affect the three steps serially from primary pathways to secondary pathways, with the effect on surface-catalyzed secondary nucleation being more favorable than that on the elongation step. In further support to this finding, all molecules showed higher inhibition of primary nucleation, which reflects their binding preference towards the species that are involved in this step, and that only at higher doses, the effect could be observed on the secondary pathways of Aβ42. In addition, these experiments have shown that lower concentrations of the small molecules are able to inhibit more significantly the surface-catalyzed secondary nucleation step than the primary nucleation step. These findings are of paramount importance for drug discovery as they provide crucial information for setting up appropriate clinical trials.

VI—Structure-Kinetics Activity Relationship (S-KAR)

In order to understand the relative contributions of the different chemical features within the scaffold of bexarotene to its activity, we have introduced a novel kinetics-based Structure-Activity Relationship approach that allows to decipher the role of each chemical component of the small molecule in inhibiting the aggregation process. We have termed this approach Structure-Kinetics Activity Relationship, or SKAR. Indeed, typical SAR studies consists of comparing the values of the dissociation constant ($K_D$), i.e. the binding affinity, between ligands and a protein. However, applying this procedure in the case of protein misfolding diseases is very challenging, since direct measurements of the $K_D$ values is not possible given the high heterogeneity and the instability of the binding species. Therefore, we have developed a novel SKAR approach, which connects the effects of small molecules on the kinetics of the aggregating protein to the chemical structure of the small molecules themselves. SKAR allows detecting weak binding events between the small molecules and co-existing species of the aggregated protein, with the output, unlike SAR where it consists of the $K_D$ values, corresponding to the rates of single microscopic steps in the aggregation reaction.

Three small molecules were designed bearing single chemical substitutions in the scaffold of bexarotene and their effect was assessed by quantifying the resulting change in the microscopic rates using our kinetics-based assay. The SKAR study collectively addressed three components within the scaffold of bexarotene (FIG. 18a): the hydrophylic group, the central linker, and the hydrophobic group. Interestingly, the kinetics experiments have shown that modifications introduced at the terminal parts, i.e. at the hydrophilic and hydrophobic groups, which aimed at decreasing the hydrophilic and hydrophobic nature of bexarotene, rendered the compound completely inactive, while modifying the central linker from an alkene to a carbonyl group did not abolish its activity. This latter modification decreased, however, the efficacy of the molecule with respect to bexarotene (FIG. 18a). These results are of paramount importance as they suggest that the dual hydrophobic-hydrophylic nature of bexarotene is crucial for inhibiting the aggregation of Aβ42 whereas the linker component affects the extent of the inhibition, likely by orienting the terminal parts in the pocket of the target. In further support to these results, all Set B and Set C molecules show a dual hydrophilic-hydrophobic properties that are separated by a linker. Moreover, in further agreement with the SKAR results, TTNPB, Tamibarotene, and SR11237 (i.e. three molecules from the Set B), which bear different substitutions only within the linker part with respect to bexarotene, delayed the aggregation of Aβ42 to different extent. These findings suggest that our SKAR strategy is crucial for i) understanding the role of individual chemical components of small molecules and ii) designing potent molecules against protein aggregation, and iii) more generally that this strategy could be used generally to assess the effect of small molecules on the aggregation of proteins that are involved in misfolding diseases.

VII—Generation of a Specific Pharmacophore Against Aβ42 Aggregation

Based on all these experiments, a specific pharmacophore against the aggregation of Aβ42 could be calculated from the scaffold of all positive molecules in Set B and Set C (FIG. 18b) (see Methods). Interestingly, the generated pharmacophore showed features that are fully consistent with the findings from the S-KAR study (FIG. 18b). Indeed, the linker component was not identified as a key feature, supporting the findings that the linker is not essential for inhibiting Aβ42 aggregation. On the other hand, the hydrophobic and hydrophilic groups are present as they play key role in inhibiting the aggregation process. Moreover, the aromatic ring within the hydrophilic terminal group that was present in the scaffold of bexarotene was not part of the generated pharmacophore, which is consistent with the structure of UVI3003 that does not possess the aromatic ring (FIG. 7).

VIII—Chemical Features of the Small Molecules that are Responsible for the Potency of the Small Molecules The RAR and RXR modulators were found to inhibit different microscopic steps in the aggregation of Aβ42. Indeed, unlike Set B molecules, the Set C molecules were found to inhibit the three steps with the effect on the primary and secondary nucleation steps being greater than that of the Set B molecules. Therefore, it was crucial to identify the chemical features that could explain these differences and subsequently to design molecules that are able to affect specific microscopic steps in the aggregation of Aβ42. The constitutional descriptors and molecular properties of the small molecules were calculated and two distinct parameters were assessed: the lipophilicity, which is expressed through its Ghose-Crippen octanol-water coefficient, and the bulkiness, which is expressed through the sum of atomic van der Waals volumes. Interestingly, we could already identify a linear correlation between these two parameters, with this correlation being able to account for the efficacy of all the small molecules (FIG. 18c).

Indeed, the greater the lipophylicity and the van der Waals values are, the highest the potency of the small molecule is, with very low values leading to completely abolishing the effect of the small molecule as in the case of BMS753. Strikingly, UVI3003, the most potent molecule in Set B, was found to possess similar potency as that of Set C molecules according to the obtained correlation (FIG. 18c). Indeed, the structure of UVI3003 is characterized by lipophylicity and van der Waals values similar to those of Set C molecules. Interestingly, in the chemical kinetics assay, although no effect could be observed on the elongation step in Aβ42 aggregation, UVI3003 was shown to inhibit the primary and secondary nucleation steps similarly to the molecules in Set C. This suggests that the lipophylicity and the van der Waals volume could describe the effect of small molecules on the primary and secondary nucleation steps, but not on the elongation step. In order to decipher the chemical feature of the small molecule that is responsible for inhibiting the elongation step, we have considered an additional parameter, which is the value of the relative aromaticity of the small molecules. Interestingly, we found that a high aromaticity value is essential for inhibiting the elongation of Aβ42 as seen in FIG. 18c. Indeed, all Set C molecules have aromaticity values greater than those of the Set B molecules.

These findings suggest that using these three parameters one is able to decipher the effect of small molecules on the microscopic steps of Aβ42 aggregation. Accordingly, virtual-based screening methods can now be used to screen databases for the aim of identifying additional small molecules and ultimately generate a diverse library of small molecules that inhibit specifically the aggregation of Aβ42.

Materials and Methods of Example II

Preparation of Aβ Peptides

The recombinant Aβ (M1-42) peptide (MDAEFRHDSGY EVHHQKLVFF AEDVGSNKGA IIGLMVGGVV IA (SEQ ID NO: 1)), here called Aβ42, was expressed in the *E. coli* BL21 Gold (DE3) strain (Stratagene, CA, U.S.A.) and purified as described previously with slight modifications (51). Briefly, the purification procedure involved sonication of *E. coli* cells, dissolution of inclusion bodies in 8 M urea, and ion exchange in batch mode on diethylaminoethyl cellulose resin and lyophylization. The lyophilized fractions were further purified using Superdex 75 HR 26/60 column (GE Healthcare, Buckinghamshire, U.K.) and eluates were analyzed using SDS-PAGE for the presence of the desired protein product. The fractions containing the recombinant protein were combined, frozen using liquid nitrogen, and lyophilized again.

Isotopically labeled $^{15}$N-Aβ42 was prepared by growing transformed *E. coli* BL21 Gold (DE3) strain (Stratagene, CA, U.S.A.) in 1 L flasks at 37° C. with 500 mL minimal M9 batch medium. Briefly, a 20 mL preculture grown overnight to saturation in LB medium containing 100 μg/L ampicilin was diluted 1/25 in 2YT medium supplemented with 100 μg/L ampicilin and grown at 37° C. When the OD at 600 nm reached 0.5, the cells were harvested, washed in minimal medium, and inoculated in ¼ of the initial culture volume of minimal M9 medium containing 100 μg/L ampicilin and supplemented with $^{15}$NH$_4$Cl (2 g/L) (Cambridge Isotopes Laboratories). Cells were grown at 37° C. for 2 hours before induction. IPTG was then added to a final concentration of 1 mM, and cells were grown at 37° C. overnight. Purification of $^{15}$N-Aβ42 was performed as described above.

Preparation of Samples for Kinetic Experiments

Solutions of monomeric peptides were prepared by dissolving the lyophilized Aβ42 peptide in 6 M GuHCl. Monomeric forms were purified from potential oligomeric species and salt using a Superdex 75 10/300 GL column (GE Healthcare) at a flowrate of 0.5 mL/min, and were eluted in 20 mM sodium phosphate buffer, pH 8 supplemented with 200 μM EDTA and 0.02% NaN$_3$. The center of the peak was collected and the peptide concentration was determined from the absorbance of the integrated peak area using ε280=1400 1 mol$^{-1}$ cm$^{-1}$. The obtained monomer was diluted with buffer to the desired concentration and supplemented with 20 μM Thioflavin T (ThT) from a 1 mM stock. All samples were prepared in low binding eppendorf tubes on ice using careful pipetting to avoid introduction of air bubbles. Each sample was then pipetted into multiple wells of a 96-well half-area, low-binding, clear bottom and PEG coating plate (Corning 3881), 80 μL per well.

For the seeded experiments, preformed fibrils were prepared just prior to the experiment. Kinetic experiments were set up just as above for a 4 μM Aβ42 samples in 20 mM sodium phosphate buffer, pH 8 with 200 μM EDTA, 0.02% NaN$_3$ and 20 μM ThT. The ThT fluorescence was monitored for 3 hours to verify the formation of fibrils.

Samples were then collected from the wells into low-binding tubes. Under the considered conditions (i.e. 4 μM Aβ42), the monomer concentration is negligible at equilibrium (31). The final concentration of fibrils, in monomer equivalents, was considered equal to the initial concentration of monomer. Fibrils were then added to freshly prepared monomer in order to reach either 1%, 2%, 5% or 10% fibrils final concentration.

In all cases, bexarotene was first solubilized in 100% DMSO to a concentration of 5 μM, and then diluted in the peptide solution to reach a final DMSO concentration of maximum 1%. We verified that the addition of 1% DMSO in the reaction mixture has no effect on Aβ42 aggregation.

Kinetic Assays

Assays were initiated by placing the 96-well plate at 37° C. under quiescent conditions in a plate reader (Fluostar Omega, Fluostar Optima or Fluostar Galaxy, BMGLabtech, Offenburg, Germany). The ThT fluorescence was measured through the bottom of the plate with a 440 nm excitation filter and a 480 nm emission filter. The ThT fluorescence was followed for three repeats of each sample.

Theoretical Analysis:

The time evolution of the total fibril mass concentration, M(t), is described by the following integrated rate law $$\frac{M(t)}{M(\infty)} = 1 - \alpha \left( \frac{B_+ + C_+}{B_+ + C_+ e^{kt}} \frac{B_- + C_+ e^{kt}}{B_- + C_+} \right)^{\frac{k_\infty^2}{kk_\infty}} e^{-k_\infty t}$$

where the kinetic parameters $B_\pm$, $C_\pm$, κ, $κ_\infty$ and $\widetilde{κ_\infty}$ are functions of the two combinations of the microscopic rate constants $k_+k_2$ and $k_nk_2$, where $k_n$, $k_+$ and $k_2$ are the primary nucleation, elongation and secondary nucleation rate constants, respectively. Aβ42 alone in 1% DMSO was first modeled to obtain the $k_+k_2$ and $k_nk_2$ combined microscopic rate constants.

With the introduction of different small molecules, the aggregation process can be inhibited by one or more individual microscopic reactions. Microscopic rate constants $k_+k_2$ and $k_nk_2$ were obtained in the presence of the molecules, and compared to the initial values of Aβ42 alone. This comparison allows one to understand which rate was mainly perturbed, as well as the potency of the compounds (by relative changes of their microscopic rates) with respect to each other.

Generation of a 3D Model of the Pharmacophore:

3D conformations of the positive compounds were first generated using CORINA.

These conformations (in a mol2 format) were used as input with default options, and the algorithm for PharmaGist was subsequently employed to generate the pharmacophore model. The features of the pharmacophore calculated was matched by all the molecules that were used as the inputs.

Calculation of Physico-Chemical Properties of Small Molecules:

Constitutional descriptors and molecular properties were calculated using E-Dragon 1.0 software. The lipophilicity of the molecule was expressed through its Ghose-Crippen octanol-water coefficient, its bulk was expressed through the sum of atomic van der Waals volumes, and its aromaticity was expressed through the aromaticity ratio.

REFERENCES

1. Alzheimer's Association, 2012 Alzheimer's disease facts and figures. *Alzheimer's Dementia* 8, 131-168 (2012).
2. F. Chiti, C. M. Dobson, Protein misfolding, functional amyloid, and human disease. *Annu. Rev. Biochem.* 75, 333-366 (2006).
3. C. M. Dobson, Protein folding and misfolding. *Nature* 426, 884-890 (2003).
4. D. J. Selkoe, Folding proteins in fatal ways. *Nature* 426, 900-904 (2003).
5. C. Haass, D. J. Selkoe, Soluble protein oligomers in neurodegeneration: lessons from the Alzheimer's amyloid β-peptide. *Nat. Rev. Mol. Cell Biol.* 8, 101-112 (2007).
6. W. E. Balch, R. I. Morimoto, A. Dillin, J. W. Kelly, Adapting proteostasis for disease intervention. *Science* 319, 916-919 (2008).
7. F. U. Hartl, A. Bracher, M. Hayer-Hartl, Molecular chaperones in protein folding and proteostasis. *Nature* 475, 324-332 (2011).
8. D. Eisenberg, M. Jucker, The amyloid state of proteins in human diseases. *Cell* 148, 1188-1203 (2012).
9. T. P. Knowles, M. Vendruscolo, C. M. Dobson, The amyloid state and its association with protein misfolding diseases. *Nat. Rev. Mol. Cell Biol.* 15, 384-396 (2014).
10. J. Habchi, P. Tompa, S. Longhi, V. N. Uversky, Introducing protein intrinsic disorder. *Chem. Rev.* 114, 6561-6588 (2014).
11. J. Bieschke, Natural compounds may open new routes to treatment of amyloid diseases. *Neurotherapeutics* 10, 429-439 (2013).
12. J. Chen, A. H. Armstrong, A. N. Koehler, M. H. Hecht, Small molecule microarrays enable the discovery of compounds that bind the Alzheimer's Abeta peptide and reduce its cytotoxicity. *J. Am. Chem. Soc.* 132, 17015-17022 (2010).
13. M. Ito, J. Johansson, R. Stromberg, L. Nilsson, Effects of ligands on unfolding of the amyloid beta-peptide central helix: mechanistic insights from molecular dynamics simulations. *PLoS One* 7, e30510 (2012).
14. H. Kroth et al., Discovery and structure activity relationship of small molecule inhibitors of toxic beta-amyloid-42 fibril formation. *J. Biol. Chem.* 287, 34786-34800 (2012).
15. M. Necula, R. Kayed, S. Milton, C. G. Glabe, Small molecule inhibitors of aggregation indicate that amyloid beta oligomerization and fibrillization pathways are independent and distinct. *J. Biol. Chem.* 282, 10311-10324 (2007).
16. Q. Nie, X. G. Du, M. Y. Geng, Small molecule inhibitors of amyloid beta peptide aggregation as a potential therapeutic strategy for Alzheimer's disease. *Acta Pharmacol. Sin.* 32, 545-551 (2011).
17. Y. Porat, A. Abramowitz, E. Gazit, Inhibition of amyloid fibril formation by polyphenols: structural similarity and aromatic interactions as a common inhibition mechanism. *Chem. Biol. Drug Des.* 67, 27-37 (2006).
18. S. Sinha et al., Lysine-specific molecular tweezers are broad-spectrum inhibitors of assembly and toxicity of amyloid proteins. *J. Am. Chem. Soc.* 133, 16958-16969 (2011).
19. A. Abelein, L. Lang, C. Lendel, A. Graslund, J. Danielsson, Transient small molecule interactions kinetically modulate amyloid beta peptide self-assembly. *FEBS Lett.* 586, 3991-3995 (2012).
20. P. T. Lansbury, H. A. Lashuel, A century-old debate on protein aggregation and neurodegeneration enters the clinic. *Nature* 443, 774-779 (2006).
21. J. L. Cummings, T. Morstorf, K. Zhong, Alzheimer's disease drug-development pipeline: few candidates, frequent failures. *Alzheimer's Res. Ther.* 6, 37 (2014).
22. P. Arosio, R. Cukalevski, B. Frohm, T. P. Knowles, S. Linse, Quantification of the concentration of Abeta42 propagons during the lag phase by an amyloid chain reaction assay. *J. Am. Chem. Soc.* 136, 219-225 (2014).
23. S. M. Butterfield, H. A. Lashuel, Amyloidogenic protein-membrane interactions: mechanistic insight from model systems. *Angew. Chem. Intl. Ed.* 49, 5628-5654 (2010).
24. S. Campioni et al., A causative link between the structure of aberrant protein oligomers and their toxicity. *Nat. Chem. Biol.* 6, 140-147 (2010).
25. G. M. Shankar et al., Amyloid-beta protein dimers isolated directly from Alzheimer's brains impair synaptic plasticity and memory. *Nat. Med.* 14, 837-842 (2008).
26. D. M. Walsh, D. J. Selkoe, A beta oligomers—a decade of discovery. *J. Neurochem.* 101, 1172-1184 (2007).
27. B. Mannini et al., Toxicity of protein oligomers is rationalized by a function combining size and surface hydrophobicity. *ACS Chem. Biol.*, (2014).
28. P. Arosio, M. Vendruscolo, C. M. Dobson, T. P. Knowles, Chemical kinetics for drug discovery to combat protein aggregation diseases. *Trends Pharmacol. Sci.* 35, 127-135 (2014).
29. T. P. Knowles et al., An analytical solution to the kinetics of breakable filament assembly. *Science* 326, 1533-1537 (2009).
30. S. I. Cohen et al., Proliferation of amyloid-beta42 aggregates occurs through a secondary nucleation mechanism. *Proc. Natl. Acad. Sci. USA* 110, 9758-9763 (2013).
31. E. Hellstrand, B. Boland, D. M. Walsh, S. Linse, Amyloid beta-protein aggregation produces highly reproducible kinetic data and occurs by a two-phase process. *ACS Chem. Neurosci.* 1, 13-18 (2010).
32. S. I. Cohen, M. Vendruscolo, C. M. Dobson, T. P. Knowles, From macroscopic measurements to microscopic mechanisms of protein aggregation. *J. Mol. Biol.* 421, 160-171 (2012).
33. P. J. Hajduk, W. R. Galloway, D. R. Spring, Drug discovery: A question of library design. *Nature* 470, 42-43 (2011).
34. D. C. Rees, M. Congreve, C. W. Murray, R. Carr, Fragment-based lead discovery. *Nat. Rev. Drug Disc.* 3, 660-672 (2004).
35. B. S. Appleby, J. L. Cummings, Discovering new treatments for Alzheimer's disease by repurposing approved medications. *Curr. Top. Med. Chem.* 13, 2306-2327 (2013).
36. A. Corbett, G. Williams, C. Ballard, Drug repositioning: an opportunity to develop novel treatments for Alzheimer's disease. Pharmaceuticals 6, 1304-1321 (2013).
37. C. Caltagirone et al., The potential protective effect of tramiprosate (homotaurine) against Alzheimer's disease: a review. *Aging Clin. Exp. Res.* 24, 580-587 (2012).
38. V. Bomben et al., Bexarotene reduces network excitability in models of Alzheimer's disease and epilepsy. *Neurobiol. Aging* 35, 2091-2095 (2014).
39. P. E. Cramer et al., ApoE-directed therapeutics rapidly clear beta-amyloid and reverse deficits in AD mouse models. *Science* 335, 1503-1506 (2012).

40. N. F. Fitz, A. A. Cronican, I. Lefterov, R. Koldamova, Comment on "ApoE-directed therapeutics rapidly clear beta-amyloid and reverse deficits in AD mouse models". *Science* 340, 924-c (2013).
41. A. R. Price et al., Comment on "ApoE-directed therapeutics rapidly clear beta-amyloid and reverse deficits in AD mouse models". *Science* 340, 924 (2013).
42. I. Tesseur et al., Comment on "ApoE-directed therapeutics rapidly clear beta-amyloid and reverse deficits in AD mouse models". *Science* 340, 924-e (2013).
43. K. Veeraraghavalu et al., Comment on "ApoE-directed therapeutics rapidly clear beta-amyloid and reverse deficits in AD mouse models". *Science* 340, 924-f (2013).
44. K. D. LaClair et al., Treatment with bexarotene, a compound that increases apolipoprotein-E, provides no cognitive benefit in mutant APP/PS1 mice. *Mol. Neurodegener.* 8, 18 (2013).
45. J. Fantini et al., Bexarotene blocks calcium-permeable ion channels formed by neurotoxic Alzheimer's beta-amyloid peptides. *ACS Chem. Neurosci.* 5, 216-224 (2014).
46. G. McColl et al., Utility of an improved model of amyloid-beta Abeta(1-42) toxicity in *Caenorhabditis elegans* for drug screening for Alzheimer's disease. *Mol. Neurodegener.* 7, 57 (2012).
47. H. Olzscha et al., Amyloid-like aggregates sequester numerous metastableproteins with essential cellular functions. *Cell* 144, 67-78 (2011).
48. S. I. Cohen et al., A molecular chaperone breaks the catalytic cycle that generates toxic Aβ oligomers. *Nat. Struct. Mol. Biol.* 22, 207-213 (2015).
49. R. A. Sperling et al., Toward defining the preclinical stages of Alzheimer's disease: recommendations from the National Institute on Aging-Alzheimer's. Association workgroups on diagnostic guidelines for Alzheimer's disease. Alzheimer's Dementia 7, 280-292 (2011).
50. D. J. Selkoe, Resolving controversies on the path to Alzheimer's therapeutics. *Nat. Med.* 17, 1060-1065 (2011).
51. D. M. Walsh et al., A facile method for expression and purification of the Alzheimer's disease-associated amyloid beta-peptide. *FEBS J.* 276, 1266-1281 (2009).
52. R. Roychaudhuri, M. Yang, M. M. Hoshi, D. B. Teplow, Amyloid β-protein assembly and Alzheimer disease. *J. Biol. Chem.* 284, 4749-4753 (2009).
53. S. Brenner, The genetics of *Caenorhabditis elegans*. *Genetics* 77, 71-94 (1974).
54. J. D. Sipe et al. *Nomenclature* 2014: Amyloid fibril proteins and clinical classification of the amyloidosis. *The Journal of Protein Folding disorders*, 21: 4, 221-224 (2015).
55. Sadowski, J.; Gasteiger, J.; Klebe, G. Journal of Chemical Information and Modeling 1994, 34, 1000-1008.
56. Schneidman-Duhovny, D.; Dror, O.; Inbar, Y.; Nussinov, R.; Wolfson, H. J. Nucleic Acids Research 2008, 36, 223-228.
57. Ref: Brenner, S. *The genetics of Caenorhabditis elegans*. *Genetics* 77, 71-94, (1974).

The invention claimed is:

1. A method of producing a pharmacophore against aggregation of an amyloid protein, the method comprising
(a) providing at least one inhibitor of protein aggregation of an amyloid protein with a known effect on at least one microscopic rate constant in the protein aggregation, wherein the microscopic rate constant is selected from the group consisting of primary nucleation and secondary nucleation, wherein said secondary nucleation forms a catalytic site for generation of toxic oligomer species;
(b) generating an inhibitor scaffold from the at least one inhibitor;
(c) introducing at least one chemical substitution into the inhibitor scaffold to prepare a modified inhibitor scaffold comprising the at least one chemical substitution and analysing the effect of the at least one chemical substitution on aggregation kinetics over time of said amyloid protein, wherein said analysing comprises: determining at least one microscopic rate constant of protein aggregation by measuring fibril mass concentration over time in the presence of said modified inhibitor scaffold comprising the at least one chemical substitution, wherein the microscopic rate constant is selected from the group consisting of primary nucleation and secondary nucleation;
(d) comparing the at least one microscopic rate constant of protein aggregation over time in step (c) against a corresponding microscopic rate constant of protein aggregation over time in the absence of said modified inhibitor to identify a reduction in the microscopic rate constant for primary nucleation and/or secondary nucleation, wherein reduction in the microscopic rate constant for primary nucleation delays the aggregation, and reduction in the microscopic rate constant for secondary nucleation decreases the number of toxic oligomers; and
(e) assessing from said reduction in the microscopic rate constant for primary nucleation and/or secondary nucleation, one or more steric and electronic features in common between said at least one inhibitor and said modified inhibitor scaffold to produce a pharmacophore against aggregation of an amyloid protein, wherein the pharmacophore comprises common steric and electronic features.

2. The method of claim 1, wherein the amyloid protein is selected from Aβ42, α-synuclein, tau, huntingtin, atrophin-1, ataxin (1,2,3,6,7, 8 12,17), amylin, prion protein, (pro) calcitonin, atrial natriuretic factor, apolipoprotein AI, apolipoprotein AII, apolipoprotein AIV, serum amyloid, medin, (apo) serum AA, prolactin, transthyretin, lysozyme, (β-2 microglobulin, fibrinogen α chain, gelsolin, keratopthelin, β-amyloid, cystatin, ABriPP immunoglobulin light chain AL, immunoglobulin heavy chain, S-IBM, islet amyloid polypeptide, insulin, lactadherin, kerato-epithelium, lactoferrin, tbn, leukocyte chemotactic factor-2, AbriPP, ADanPP, lung surfactant protein, galectin 7, corneodesmosin, lactadherin, kerato-epithelium, odontogenic ameloblast-associated protein, semenogelin 1 and enfurvitide.

3. The method of claim 2, wherein the protein is Aβ42.

4. The method of claim 1, wherein said introducing comprises chemically modifying said inhibitor scaffold and said determining comprises contacting said modified inhibitor scaffold with an amyloid protein.

5. The method of claim 1, wherein the protein aggregation over time is represented by a time-dependent sigmoidal curve, wherein said curve comprises at least a lag phase, a growth phase and a plateau originating from primary nucleation, secondary nucleation and elongation processes and wherein said modified inhibitor scaffold alters at least one of primary nucleation or secondary nucleation.

6. The method of claim 1, wherein microscopic rate constants are obtained from the aggregation kinetics over time by fitting the curves using the following equation:

$$\frac{M(t)}{M(\infty)} = 1 - \alpha \left( \frac{B_+ + C_+}{B_+ + C_+ e^{kt}} \frac{B_- + C_+ e^{kt}}{B_- + C_+} \right)^{\frac{k_\infty^2}{kk_\infty}} e^{-k_\infty t}$$

where the parameters $B_\pm$, $C_\pm$, $\kappa$, $\kappa_\infty$ and $\widetilde{\kappa_\infty}$ are functions of the two combinations of the microscopic rate constants $k_+ k_2$ and $k_n k_2$, where $k_n$, $k_+$ and $k_2$ are the primary nucleation, elongation and secondary nucleation rate constants, respectively.

7. The method of claim 1, wherein said modified inhibitor scaffold inhibits both primary and secondary nucleation.

8. The method of claim 1, wherein the inhibitor of (a) is itself identified by analysing the effect of the inhibitor on the aggregation kinetics of the amyloid protein.

9. The method of claim 1, wherein said modified inhibitor scaffold reduces the nucleation rate $r(t)=k_2 M(t)m(t)^2+k_n m(t)^2$.

10. The method of claim 1, wherein the modified inhibitor scaffold is effective at sub-stoichiometric concentrations compared to the aggregating protein.

11. The method of claim 1, wherein the assessing in step (e) comprises generating three-dimensional conformations of modified inhibitor scaffolds identified in step (d) that reduce the microscopic rate constant for primary and/or secondary nucleation, aligning the three-dimensional conformations of the modified inhibitor scaffolds, and producing a pharmacophore from the steric and electronic features, wherein all of the steric and electronic features of the pharmacophore are matched by those identified from the modified inhibitor scaffolds.

* * * * *